(12) United States Patent
Maliga et al.

(10) Patent No.: US 7,186,560 B2
(45) Date of Patent: Mar. 6, 2007

(54) HIGH LEVEL EXPRESSION OF IMMUNOGENIC PROTEINS IN THE PLASTIDS OF HIGHER PLANTS

(75) Inventors: Pal Maliga, East Brunswick, NJ (US); Gordon Dougan, London (GB); John Tregoning, London (GB); Peter Nixon, London (GB)

(73) Assignee: Rutgers, The State University of New Jersey, New Brunswick, NJ (US)

(*) Notice: Subject to any disclaimer, the term of this patent is extended or adjusted under 35 U.S.C. 154(b) by 0 days.

(21) Appl. No.: 10/109,812

(22) Filed: Mar. 29, 2002

(65) Prior Publication Data

US 2003/0088081 A1 May 8, 2003

Related U.S. Application Data

(63) Continuation-in-part of application No. 10/088,634, filed as application No. PCT/US00/25930 on Sep. 21, 2000.

(60) Provisional application No. 60/279,591, filed on Mar. 29, 2001, provisional application No. 60/335,699, filed on Oct. 25, 2001, provisional application No. 60/211,139, filed on Jun. 13, 2000, provisional application No. 60/155,007, filed on Sep. 21, 1999.

(51) Int. Cl.
  C12N 15/82 (2006.01)
  C12N 5/10 (2006.01)
  C12N 15/00 (2006.01)

(52) U.S. Cl. .................. 435/468; 435/320.1; 435/419

(58) Field of Classification Search ............. 435/320.1, 435/419, 468; 800/278, 288
See application file for complete search history.

(56) References Cited

U.S. PATENT DOCUMENTS

| | | | |
|---|---|---|---|
| 5,571,694 A * | 11/1996 | Makoff et al. | ............. 435/69.3 |
| 5,614,395 A | 3/1997 | Ryals et al. | |
| 5,686,079 A | 11/1997 | Curtiss, III et al. | |
| 5,877,402 A | 3/1999 | Maliga et al. | |
| 6,110,736 A | 8/2000 | Hodges et al. | |
| 6,149,919 A | 11/2000 | Domenighini et al. | |
| 6,297,054 B1 | 10/2001 | Maliga et al. | |
| 6,376,744 B1 | 4/2002 | Maliga et al. | |
| 6,388,168 B1 | 5/2002 | Maliga et al. | |
| 6,472,586 B1 | 10/2002 | Maliga et al. | |

FOREIGN PATENT DOCUMENTS

| | | |
|---|---|---|
| EP | 0 430 645 A2 | 6/1991 |
| WO | WO 01/77353 A2 | 10/2001 |

OTHER PUBLICATIONS

Svab et al., PNAS, 1993, vol. 90, pp. 913-917.*
Haq et al., Science, 1995, vol. 268, pp. 714-716.*
Gianelli et al., Infect. Immun., 1997, vol. 65, pp. 331-334.*
Khan, M.S. "Fluorescent antibiotic resistance marker for tracking plastid transformation in higher plants"; Nature Biotechnoogy, 17: 910-915 (1999).
Dale, E.C. "Gene transfer with subsequent removal of the selection gene from the host genome"; Proc. Natl. Acad. Sci. USA, 88: 10558-10562 (1991).
Srivastava, V. "Single-copy transgenic wheat generated through the resolution of complex integration patterns"; Proc. Natl. Acad. Sci. USA, 96: 11117-11121 (1999).
Le, Y. "Nuclear targeting determinants of the phage P1 Cre DNA recombinase"; Nucleic Acids Research, 27(24): 4703-4709 (1999).
Lyznik, LA. "Activity of yeast FLP recombinase in maize and rice protoplasts"; Nucleic Acids Research, 21(4): 969-975 (1993).
Lyznik, L.A. "FLP-mediated recombination of FRT sites in the maize genome"; Nucleic Acids Research, 24(19): 3784-3789 (1996).
Zoubenko, O.V. "Efficient targeting of foreign genes into the tobacco plastid genome"; Nucleic Acids Research, 22(19): 3819-3824 (1994).
Love, J. "Stringent control of transgene expression in *Arabidopsis thaliana* using the Top10 promoter system"; The Plant Journal, 21(6): 579-588 (2000).
Serino, G. "A Negative selection scheme based on the expression of cytosine deaminase in plastids"; The Plant Journal, 12(3): 697-701 (1997).
Lyznik, L.A. "Heat-inducible expression of FLP gene in maize cells"; The Plant Journal, 8(2): 177-186 (1995).
Soll, J. "Protein translocation into and across the chloroplastic envelope membranes"; Plant Molecular Biology, 38: 191-207 (1998).
Adams, D. "Cre-lox Recombination in *Escherichia coli* Cells Mechanistic Differences from the in Vitro Reaction", J. Mol. Biol., 226: 661-673 (1992).
Craig, N.L. "The Mechanism of Conservative Site-Specific Recombination"; Annu. Rev. Genet., 22: 77-105 (1988).
Lichtenstein, C. "Prospects for reverse genetics in plants using recombination"; Plant Molecular Biology, 21: v-xii (1993).
Lubben, T.H. "Chloroplast import characteristics of chimeric proteins"; Plant Molecular Biology; 12: 13-18 (1989).
Russell, S.H. "Directed excision of a transgene from the plant genome"; Mol Gen Genet, 234: 49-59 (1992).
Timko, M.P. "Structure and Expression of Nuclear Genes Encoding Polypeptides of the Photosynthetic Apparatus"; Mol Biol of the Photosynthetic Apparatus, 381-396 (1985).
Timmermans, M.C.P. "The pFF plasmids: cassettes utilising CaMV sequences for expression of foreign genes in plants"; Journal of Biotechnology, 14: 333-344 (1990).
Wasmann, C.C. "The importance of the transit peptide and the transported protein for protein import into chloroplasts"; Mol Gen Genet, 205: 446-453 (1986).

(Continued)

*Primary Examiner*—Ashwin Mehta
(74) *Attorney, Agent, or Firm*—Kathleen D. Rigaut; Dann Dorfman Herrell & Skillman

(57) ABSTRACT

A site specific recombination system and methods of use thereof are disclosed for manipulating the genome of higher plants. Compositions and methods for expressing immunogenic proteins using the site specific reombination system are also provided.

10 Claims, 30 Drawing Sheets

OTHER PUBLICATIONS

Pizza, M. "A Genetically Detoxified Derivative of Heat-labile *Escherichia coli* Enterotoxin Induces Neutralizing . . . "; J. Exp. Med., 180: 2147-2153 (1994).

Ma, S.W. "Transgenic plants expressing autoantigens fed to mice to induce oral immune tolerance"; Nature Medicine; 3(7): 793-796 (1997).

Kuroda, H. "Complementarity of the 16S rRNA penultimate stem with sequences downstream of the AUG destabilized the plastid mRNAs"; Nucleic Acids Research, 29-4: 970-975 (2001).

Kuroda, H. "Sequences Downstream of the Translation Initiation Codon Are Important Determinants of Translation Efficiency in Chloroplasts"; Plant Phys, 125: 430-436 (2001).

Ye, G. "Plastid-expressed 5-enolpyruvylshikimate-3-phosphate synthase genes provide high level glyphosate tolerance in tobacco"; The Plant Journal, 25(3): 261-270 (2001).

Staub, J.M. "High-yield production of human therapeutic protein in tobacco chloroplasts"; Nature Biotechnology, 18: 333-338 (2000).

Heifetz, P.B. "Genetic engineering of the chloroplast"; Biochimie, 82: 655-666 (2000).

Giddings, G. "Transgenic plants as factories for biopharmaceuticals"; Nature Biotechnology, 18: 1151-1155 (2000).

Douce, G. "Genetically Detoxified Mutants of Heat-Labile Toxin from *Escherichia coli* Are Able To Act as Oral Adjuvants"; Infection and Immunity, 67(9): 4400-4406 (1999).

Douce, G. "Mucosal immunogenicity of genetically detoxified derivatives of heat labile toxin from *Escherichia coli*"; Vaccine, 16(11/12): 1065-1073 (1998).

Barchfeld, G.L. "The adjuvants MF59 and LT-K63 enhance the mucosal and systemic immunogenicity of subunit influenza vaccine administered..in mice"; Vaccine, 17: 695-704 (1999).

Carrier, H. "Kanamycin resistance as a selectable marker for plastid transformation in tobacco"; Mol Gen Genet, 241: 49-56 (1993).

Corneille, S. Efficient elimination of selectable marker genes from the plastid genome by the CRE-lox site-specific recombination . . . The Plant Journal, 27(2): 171-178 (2001).

Hajdukiewicz, P. "Multiple pathways for Cre/lox-mediated recombination in plastids" The Plant Journal, 27(2): 161-170 (2001).

Daniell, H. "Marker free transgenic plants: engineering the chloroplast gene without the use of antibiotic selection" Curr. Genet., 39: 109-116 (2001).

Tacket, C. "Immunogenicity in humans of a recombinant bacterial antigen delivered in a transgenic potato" Nature Medicine, 4(5): 607-609 (1998).

Tacket, C. "A review of oral vaccination with transgenic vegetables" Microbes and Infection, 777-783 (1999).

Tregoning, J. "Expression of tetanus toxin Fragment C in tobacco chloroplasts" Nucleic Acids Research, 31(4): 1174-1179 (2003).

Bock, R. "Transgenic Plastids in Basic Research and Plant Biotechnology" J. Mol. Biol., 312: 425-438 (2001).

Magagnoli, C. "Mutations in the A Subunit Affect Yield, Stability, and Protease Sensitivity of Nontoxic Derivatives . . . " Infection and Immunity, 64(12): 5434-5438 (1996).

* cited by examiner

*Nt*-pJST10    *Nt*-pJST11

SEQUENCE LISTING

<160> NUMBER OF SEQ ID NOS: 57

<210> SEQ ID NO 1
<211> LENGTH: 130
<212> TYPE: DNA
<213> ORGANISM: tobacco

<400> SEQUENCE: 1
gagctcgctc ccccgccgtc gttcaatgag aatggataag aggctcgtgg gattgacgtg      60 aggggcagg gatggctata tttctgggag cataacttcg tataatgtat gctatacgaa     120
gttatctaga                                                            130

<210> SEQ ID NO 2
<211> LENGTH: 264
<212> TYPE: DNA
<213> ORGANISM: tobacco

<400> SEQUENCE: 2
gaattcataa cttcgtatag catacattat acgaagttat agacattagc agataaatta      60
gcaggaaata aagaaggata aggagaaaga actcaagtaa ttatccttcg ttctcttaat     120
tgaattgcaa ttaaactcgg cccaatcttt tactaaaagg attgagccga atacaacaaa     180
gattctattg catatatttt gactaagtat atacttacct agatatacaa gatttgaaat     240
acaaaatcta gcaagcttgg tacc                                            264

<210> SEQ ID NO 3
<211> LENGTH: 1051
<212> TYPE: DNA
<213> ORGANISM: Escherichia coli

<400> SEQUENCE: 3

| | | | | | |
|---|---|---|---|---|---|
| gagctccatg | gctagctcca | atttactgac | cgtacaccaa | aatttgcctg | cattaccggt | 60 |
| cgatgcaacg | agtgatgagg | ttcgcaagaa | cctgatggac | atgttcaggg | atcgccaggc | 120 |
| gttttctgag | catacctgga | aaatgcttct | gtccgtttgc | cggtcgtggg | cggcatggtg | 180 |
| caagttgaat | aaccggaaat | ggtttcccgc | agaacctgaa | gatgttcgcg | attatcttct | 240 |
| atatcttcag | gcgcgcggtc | tggcagtaaa | aactatccag | caacatttgg | gccagctaaa | 300 |
| catgcttcat | cgtcggtccg | ggctgccacg | accaagtgac | agcaatgctg | tttcactggt | 360 |
| tatgcggcgg | atccgaaaag | aaaacgttga | tgccggtgaa | cgtgcaaaac | aggctctagc | 420 |
| gttcgaacgc | actgatttcg | accaggttcg | ttcactcatg | aaaatagcg | atcgctgcca | 480 |
| ggatatacgt | aatctggcat | ttctggggat | tgcttataac | accctgttac | gtatagccga | 540 |
| aattgccagg | atcagggtta | agatatctc | acgtactgac | ggtgggagaa | tgttaatcca | 600 |
| tattggcaga | acgaaaacgc | tggttagcac | cgcaggtgta | gagaaggcac | ttagcctggg | 660 |
| ggtaactaaa | ctggtcgagc | gatggatttc | cgtctctggt | gtagctgatg | atccgaataa | 720 |
| ctacctgttt | tgccgggtca | gaaaaaatgg | tgttgccgcg | ccatctgcca | ccagccagct | 780 |
| atcaactcgc | gccctggaag | ggattttga | agcaactcat | cgattgattt | acggcgctaa | 840 |
| ggatgactct | ggtcagagat | acctggcctg | gtctggacac | agtgcccgtg | tcggagccgc | 900 |
| gcgagatatg | gcccgcgctg | gagtttcaat | accggagatc | atgcaagctg | gtggctggac | 960 |
| caatgtaaat | attgtcatga | actatatccg | taacctggat | agtgaaacag | gggcaatggt | 1020 |
| gcgcctgctc | gaggatggcg | attagtctag | a | | | 1051 |

<210> SEQ ID NO 4
<211> LENGTH: 131
<212> TYPE: DNA
<213> ORGANISM: tobacco

<400> SEQUENCE: 4

| | | | | | |
|---|---|---|---|---|---|
| gagctcgctc | ccccgccgtc | gttcaatgag | aatggataag | aggctcgtgg | gattgacgtg | 60 |
| aggggggcagg | gatggctata | tttctgggag | cataacttcg | tataatgtat | gctatacgaa | 120 |
| gttatgaatt | c | | | | | 131 |

<210> SEQ ID NO 5
<211> LENGTH: 263
<212> TYPE: DNA
<213> ORGANISM: tobacco

<400> SEQUENCE: 5

| | | | | | |
|---|---|---|---|---|---|
| tctagataac | ttcgtataat | gtatgctata | cgaagttata | gacattagca | gataaattag | 60 |
| caggaaataa | agaaggataa | ggagaaagaa | ctcaagtaat | tatccttcgt | tctcttaatt | 120 |
| gaattgcaat | taaactcggc | ccaatctttt | actaaaagga | ttgagccgaa | tacaacaaag | 180 |
| attctattgc | atatattttg | actaagtata | tacttaccta | gatatacaag | atttgaaata | 240 |
| caaaatctag | caagcttggt | acc | | | | 263 |

<210> SEQ ID NO 6
<211> LENGTH: 239
<212> TYPE: DNA

<213> ORGANISM: pea Rubisco

<400> SEQUENCE: 6

| ccggatccaa ttcaaccaca agaactaaca aagtcagaaa aatggcttct atgatatcct | 60 |
| cttccgctgt gacaacagtc agccgtgctt ctagggtgca atccgcggca gtggctccat | 120 |
| tcggcggcct gaaatccatg actggattcc cagtgaagaa ggtcaacact gacattactt | 180 |
| ccattacaag caatggtgga agagtaaagt gcatgcaggt gtggcctgcc atggctagc | 239 |

<210> SEQ ID NO 7
<211> LENGTH: 287
<212> TYPE: DNA
<213> ORGANISM: pea Rubisco

<400> SEQUENCE: 7

| ccggatccaa ttcaaccaca agaactaaca aagtcagaaa aatggcttct atgatatcct | 60 |
| cttccgctgt gacaacagtc agccgtgctt ctagggtgca atccgcggca gtggctccat | 120 |
| tcggcggcct gaaatccatg actggattcc cagtgaagaa ggtcaacact gacattactt | 180 |
| ccattacaag caatggtgga agagtaaagt gcatgcaggt gtggcctcca attggaaaga | 240 |
| agaagtttga gactctttcc tatttgccac cattgaccat ggctagc | 287 |

<210> SEQ ID NO 8
<211> LENGTH: 298
<212> TYPE: DNA
<213> ORGANISM: pea Rubisco

<400> SEQUENCE: 8

| ccggatccaa ttcaaccaca agaactaaca aagtcagaaa aatggcttct atgatatcct | 60 |
| cttccgctgt gacaacagtc agccgtgctt ctagggtgca atccgcggca gtggctccat | 120 |
| tcggcggcct gaaatccatg actggattcc cagtgaagaa ggtcaacact gacattactt | 180 |
| ccattacaag caatggtgga agagtaaagt gcatgcaggt gtggcctcca attggaaaga | 240 |
| agaagtttga gactctttcc tatttgccac cattgaccag agatcagttg gctagcgg | 298 |

<210> SEQ ID NO 9
<211> LENGTH: 508
<212> TYPE: DNA
<213> ORGANISM: Agrobacterium

<400> SEQUENCE: 9

| gaattcattt tcacgtgtgg aagatatgaa ttttttgag aaactagata agattaatga | 60 |
| atatcggtgt tttggttttt tcttgtggcc gtctttgttt atattgagat ttttcaaatc | 120 |
| agtgcgcaag acgtgacgta agtatctgag ctagttttta tttttctact aatttggtcg | 180 |
| tttatttcgg cgtgtaggac atggcaaccg ggcctgaatt tcgcgggtat tctgtttcta | 240 |
| ttccaacttt ttcttgatcc gcagccatta acgacttttg aatagatacg ctgacacgcc | 300 |
| aagcctcgct agtcaaaagt gtaccaaaca acgctttaca gcaagaacgg aatgcgcgtg | 360 |
| acgctcgcgg tgacgccatt tcgccttttc agaaatggat aaatagcctt gcttcctatt | 420 |
| atatcttccc aaattaccaa tacattacac tagcatctga atttcataac caatctcgat | 480 |
| acaccaaatc gataggatcc taccatgg | 508 |

<210> SEQ ID NO 10
<211> LENGTH: 829
<212> TYPE: DNA
<213> ORGANISM: Cauliflower mosaic virus

<400> SEQUENCE: 10

```
aagcttgcca acatggtgga gcacgacact ctcgtctact ccaagaatat caaagataca    60
gtctcagaag accaaagggc tattgagact tttcaacaaa gggtaatatc gggaaacctc   120
ctcggattcc attgcccagc tatctgtcac ttcatcaaaa ggacagtaga aaggaaggt    180
ggcacctaca aatgccatca ttgcgataaa ggaaaggcta tcgttcaaga tgcctctgcc   240
gacagtggtc ccaaagatgg acccccaccc acgaggagca tcgtggaaaa agaagacgtt   300
ccaaccacgt cttcaaagca gtggattga tgtgataaca tggtgagca cgacactctc    360
gtctactcca agaatatcaa agatacagtc tcagaagacc aaagggctat tgagactttt   420
caacaaaggg taatatcggg aaacctcctc ggattccatt gcccagctat ctgtcacttc   480
atcaaaagga cagtagaaaa ggaaggtggc acctacaaat gccatcattg cgataaagga   540
aaggctatcg ttcaagatgc ctctgccgac agtggtccca agatggaccc ccacccacg    600
aggagcatcg tggaaaaaga gacgttcca accacgtctt caaagcaagt ggattgatgt    660
gatatctcca ctgacgtaag ggatgacgca caatcccact atccttcgca agacccttcc   720
tctatataag gaagttcatt tcatttggag aggacacgct gaaatcacca gtctctctct   780
acaaatctat ctctctcgat cgcgagctc ggtacccggg gatcgatcc                829
```

<210> SEQ ID NO 11
<211> LENGTH: 86
<212> TYPE: DNA
<213> ORGANISM: tobacco

<400> SEQUENCE: 11

```
ggtaccataa cttcgtataa tgtatgctat acgaagttat agatctataa cttcgtataa    60
tgtatgctat acgaagttat aagctt                                         86
```

<210> SEQ ID NO 12
<211> LENGTH: 895
<212> TYPE: DNA
<213> ORGANISM: tobacco

<400> SEQUENCE: 12

```
gagatctggg aggaataact tatgggggtc gacataactt cgtataatgt atgctatacg    60
aagttattag aagcggtgat cgccgaagta tcgactcaac tatcagaggt agttggcgtc   120
atcgagcgcc atctcgaacc gacgttgctg ccgtacatt tgtacggctc cgcagtggat    180
ggcggcctga agccacacag tgatattgat ttgctggtta cggtgaccgt aaggcttgat   240
gaaacaacgc ggcgagcttt gatcaacgac cttttggaaa cttcggcttc ccctggagag   300
agcgagattc tccgcgctgt agaagtcacc attgttgtgc acgacgacat cattccgtgg   360
cgttatccag ctaagcgcga actgcaattt ggagaatggc agcgcaatga cattcttgca   420
ggtatcttcg agccagccac gatcgacatt gatctggcta tcttgctgac aaaagcaaga   480
gaacatagcg ttgccttggt aggtccagcg cggaggaac tctttgatcc ggttcctgaa    540
caggatctat ttgaggcgct aaatgaaacc ttaacgctat ggaactcgcc gcccgactgg   600
gctggcgatg agcgaaatgt agtgcttacg ttgtcccgca tttggtacag cgcagtaacc   660
ggcaaaatcg cgccgaagga tgtcgctgcc gactgggcaa tggagcgcct gccggcccag   720
tatcagcccg tcatacttga agctagacag gcttatcttg acaagaaga gatcgcttg    780
gcctcgcgcg cagatcagtt ggaagaattt gtccactacg tgaaaggcga gatcaccaag   840
```

```
gtagtcggca ataaataac ttcgtataat gtatgctata cgaagttata ctagt        895

<210> SEQ ID NO 13
<211> LENGTH: 1049
<212> TYPE: DNA
<213> ORGANISM: tobacco

<400> SEQUENCE: 13
gagctcgctc ccccgccgtc gttcaatgag aatggataag aggctcgtgg gattgacgtg    60 aggggcagg gatggctata tttctgggag aattaaccga tcgacgtgca agcggacatt    120
tattttaaat tcgataattt ttgcaaaaac atttcgacat atttatttat tttattatta   180 tgggataac ttcgtataat gtatgctata cgaagttatt agaagcggtg atcgccgaag    240
tatcgactca actatcagag gtagttggcg tcatcgagcg ccatctcgaa ccgacgttgc    300
tggccgtaca tttgtacggc tccgcagtgg atggcggcct gaagccacac agtgatattg   360
atttgctggt tacggtgacc gtaaggcttg atgaaacaac gcggcgagct ttgatcaacg    420
accttttgga aacttcggct tcccctggag agagcgagat tctccgcgct gtagaagtca    480
ccattgttgt gcacgacgac atcattccgt ggcgttatcc agctaagcgc gaactgcaat    540
ttggagaatg gcagcgcaat gacattcttg caggtatctt cgagccagcc acgatcgaca    600
ttgatctggc tatcttgctg acaaaagcaa gagaacatag cgttgccttg gtaggtccag    660
cggcggagga actctttgat ccggttcctg aacaggatct atttgaggcg ctaaatgaaa    720
ccttaacgct atggaactcg ccgcccgact gggctggcga tgagcgaaat gtagtgctta    780
cgttgtcccg catttggtac agcgcagtaa ccggcaaaat cgcgccgaag gatgtcgctg    840
ccgactgggc aatggagcgc ctgccggccc agtatcagcc cgtcatactt gaagctagac    900
aggcttatct tggacaagaa gaagatcgct tggcctcgcg cgcagatcag ttggaagaat    960
ttgtccacta cgtgaaaggc gagatcacca aggtagtcgg caaataaata acttcgtata   1020
atgtatgcta tacgaagtta ttagctagc                                     1049

<210> SEQ ID NO 14
<211> LENGTH: 31
<212> TYPE: DNA
<213> ORGANISM: Artificial Sequence
<220> FEATURE:
<223> OTHER INFORMATION: Primer

<400> SEQUENCE: 14
ggggagctcg ctcccccgcc gtcgttcaat g                                   31

<210> SEQ ID NO 15
<211> LENGTH: 61
<212> TYPE: DNA
<213> ORGANISM: Artificial Sequence
<220> FEATURE:
<223> OTHER INFORMATION: Primer

<400> SEQUENCE: 15
gggaattcat aacttcgtat agcatacatt atacgaagtt atgctcccag aaatatagcc    60
a                                                                    61

<210> SEQ ID NO 16
<211> LENGTH: 37
<212> TYPE: DNA
<213> ORGANISM: Artificial Sequence
<220> FEATURE:
<223> OTHER INFORMATION: Primer
```

```
<400> SEQUENCE: 16
aattcgaagc gcttggatac agttgtaggg agggatc                                    37

<210> SEQ ID NO 17
<211> LENGTH: 37
<212> TYPE: DNA
<213> ORGANISM: Artificial Sequence
<220> FEATURE:
<223> OTHER INFORMATION: Primer

<400> SEQUENCE: 17
catggatccc tccctacaac tgtatccaag cgcttcg                                    37

<210> SEQ ID NO 18
<211> LENGTH: 60
<212> TYPE: DNA
<213> ORGANISM: Artificial Sequence
<220> FEATURE:
<223> OTHER INFORMATION: Primer

<400> SEQUENCE: 18
ggtctagata acttcgtata atgtatgcta tacgaagtta tagacattag cagataaatt           60

<210> SEQ ID NO 19
<211> LENGTH: 40
<212> TYPE: DNA
<213> ORGANISM: Artificial Sequence
<220> FEATURE:
<223> OTHER INFORMATION: Primer

<400> SEQUENCE: 19
gggggtacca agcttgctag attttgtatt tcaaatcttg                                 40

<210> SEQ ID NO 20
<211> LENGTH: 31
<212> TYPE: DNA
<213> ORGANISM: Artificial Sequence
<220> FEATURE:
<223> OTHER INFORMATION: Primer

<400> SEQUENCE: 20
ccgaattcca ttttcacgtg tggaagatat g                                          31

<210> SEQ ID NO 21
<211> LENGTH: 41
<212> TYPE: DNA
<213> ORGANISM: Artificial Sequence
<220> FEATURE:
<223> OTHER INFORMATION: Primer

<400> SEQUENCE: 21
ccccatggta ggatcctatc gatttggtgt atcgagattg g                               41

<210> SEQ ID NO 22
<211> LENGTH: 29
<212> TYPE: DNA
<213> ORGANISM: Artificial Sequence
<220> FEATURE:
<223> OTHER INFORMATION: Primer

<400> SEQUENCE: 22
ccggatccaa ttcaaccaca agaactaac                                             29

<210> SEQ ID NO 23
```

```
<211> LENGTH: 34
<212> TYPE: DNA
<213> ORGANISM: Artificial Sequence
<220> FEATURE:
<223> OTHER INFORMATION: Primer

<400> SEQUENCE: 23
ggggctagcc atggcaggcc acacctgcat gcac                                   34

<210> SEQ ID NO 24
<211> LENGTH: 32
<212> TYPE: DNA
<213> ORGANISM: Artificial Sequence
<220> FEATURE:
<223> OTHER INFORMATION: Primer

<400> SEQUENCE: 24
ggggctagcc atggtcaatg ggttcaaata gg                                     32

<210> SEQ ID NO 25
<211> LENGTH: 40
<212> TYPE: DNA
<213> ORGANISM: Artificial Sequence
<220> FEATURE:
<223> OTHER INFORMATION: Primer

<400> SEQUENCE: 25
ggggagctcc atggctagct ccaatttact gaccgtacac                              40

<210> SEQ ID NO 26
<211> LENGTH: 42
<212> TYPE: DNA
<213> ORGANISM: Artificial Sequence
<220> FEATURE:
<223> OTHER INFORMATION: Primer

<400> SEQUENCE: 26
gggtctagac taatcgccat cctcgagcag gcgcaccatt gc                           42

<210> SEQ ID NO 27
<211> LENGTH: 19
<212> TYPE: DNA
<213> ORGANISM: tobacco
<220> FEATURE:
<223> OTHER INFORMATION: Primer

<400> SEQUENCE: 27
tcaatcgatg agttgcttc                                                    19

<210> SEQ ID NO 28
<211> LENGTH: 60
<212> TYPE: DNA
<213> ORGANISM: Artificial Sequence
<220> FEATURE:
<223> OTHER INFORMATION: Primer

<400> SEQUENCE: 28
ggtctagata acttcgtata gcatacatta tacgaagtta tgctcccaga aatatagcca        60

<210> SEQ ID NO 29
<211> LENGTH: 61
<212> TYPE: DNA
<213> ORGANISM: Artificial Sequence
<220> FEATURE:
<223> OTHER INFORMATION: Primer

<400> SEQUENCE: 29
```

```
gggaattcat aacttcgtat agcatacatt atacgaagtt atagacatta gcagataaat    60
t                                                                    61
```

<210> SEQ ID NO 30
<211> LENGTH: 16
<212> TYPE: DNA
<213> ORGANISM: Artificial Sequence
<220> FEATURE:
<223> OTHER INFORMATION: initiation sequence

<400> SEQUENCE: 30

```
ggaggaataa cttatg                                                    16
```

<210> SEQ ID NO 31
<211> LENGTH: 1370
<212> TYPE: DNA
<213> ORGANISM: Escherichia coli

<400> SEQUENCE: 31

```
catatgaaaa atctggattg ttgggtcgac aatgaagaag atatagatgt tatattaaaa     60
aagagtacaa ttttaaattt agatattaat aatgatatta tatcagatat atctgggttt    120
aattcatctg taataacata tccagatgct caattggtgc ccggaataaa tggcaaagca    180
atacatttag taaacaatga atcttctgaa gttatagtgc ataaagctat ggatattgaa    240
tataatgata tgtttaataa ttttaccgtt agcttttggt tgagggttcc taaagtatct    300
gctagtcatt tagaacaata tggcacaaat gagtattcaa taattagctc tatgaaaaaa    360
catagtctat caataggatc tggttggagt gtatcactta aggtaataa cttaatatgg    420
actttaaaag attccgcggg agaagttaga caaataactt ttagggattt acctgataaa    480
tttaatgctt atttagcaaa taaatgggtt tttataacta ttactaatga tagattatct    540
tctgctaatt tgtatataaa tggagtactt atgggaagtg cagaaattac tggtttagga    600
gctattagag aggataataa tataacatta aaactagata gatgtaataa taataatcaa    660
tacgtttcta ttgataaatt taggatattt tgcaaagcat taaatccaaa agagattgaa    720
aaattataca caagttattt atctataacc ttttaagag acttctgggg aaaacccttta   780
cgatatgata cagaatatta tttaatacca gtagcttcta gttctaaaga tgttcaattg    840
aaaaatataa cagattatat gtatttgaca aatgcgccat cgtatactaa cggaaaattg    900
aatatatatt atagaaggtt atataatgga ctaaaattta ttataaaaag atatacacct    960
aataatgaaa tagattcttt tgttaaatca ggtgatttta ttaaattata tgtatcatat   1020
aacaataatg agcacattgt aggttatccg aaagatggaa atgcctttaa taatcttgat   1080
agaattctaa gagtaggtta taatgcccca ggtatccctc tttataaaaa aatggaagca   1140
gtaaaattgc gtgatttaaa aacctattct gtacaactta attatatga tgataaaaat   1200
gcatctttag gactagtagg tacccataat ggtcaaatag gcaacgatcc aaatagggat   1260
atattaattg caagcaactg gtactttaat catttaaaag ataaaatttt aggatgtgat   1320
tggtactttg tacctacaga tgaaggatgg acaaatgatt aatttctaga              1370
```

<210> SEQ ID NO 32
<211> LENGTH: 1368
<212> TYPE: DNA
<213> ORGANISM: Artificial Sequence
<220> FEATURE:
<223> OTHER INFORMATION: Synthetic

<400> SEQUENCE: 32

```
catatgaaaa accttgattg ttgggtcgac aacgaagaag acatcgatgt tatcctgaaa     60
aagtctacca ttctgaactt ggacatcaac aacgatatta ctctccgacat ctctggtttc    120
aactcctctg ttatcacata tccagatgct caattggtgc cgggcatcaa cggcaaagct    180
atccacctgg ttaacaacga atcttctgaa gttatcgtgc acaaggccat ggacatcgaa    240
tacaacgaca tgttcaacaa cttcaccgtt agcttctggc tgcgcgttcc gaaagtttct    300
gcttcccacc tggaacagta cggcactaac gagtactcca tcatcagctc tatgaagaaa    360
cactccctgt ccatcggctc tggttggtct gtttccctga gggtaacaa cctgatctgg     420
actctgaaag actccgcggg cgaagttcgt cagatcactt tccgcgacct gccggacaag    480
ttcaacgcgt acctggctaa caatgggtt ttcatcacta tcactaacga tcgtctgtct    540
tctgctaacc tgtacatcaa cggcgttctg atgggctccg ctgaaatcac tggtctgggc    600
gctatccgtg aggacaacaa catcactctt aagctggacc gttgcaacaa caacaaccag    660
tacgtatcca tcgacaagtt ccgtatcttc tgcaaagcac tgaacccgaa agagatcgaa    720
aaactgtata ccagctacct gtctatcacc ttcctgcgtg acttctgggg taacccgctg    780
cgttacgaca ccgaatatta cctgatcccg gtagcttcta gctctaaaga cgttcagctg    840
aaaaacatca ctgactacat gtacctgacc aacgcgccgt cctacactaa cggtaaactg    900
aacatctact accgacgtct gtacaacggc ctgaaattca tcatcaaacg ctacactccg    960
aacaacgaaa tcgattcttt cgttaaatct ggtgacttca tcaaactgta cgtttcttac   1020
aacaacaacg aacacatcgt tggttacccg aaagacggta acgctttcaa caacctggac   1080
agaattctgc gtgttggtta caacgctccg ggtatcccgc tgtacaaaaa aatggaagct   1140
gttaaactgc gtgacctgaa aacctactct gttcagctga actgtacga cgacaaaaac   1200
gcttctctgg gtctggttgg tacccacaac ggtcagatcg gtaacgaccc gaaccgtgac   1260
atcctgatcg cttctaactg gtacttcaac cacctgaaag acaaaatcct gggttgcgac   1320
tggtacttcg ttccgaccga tgaaggttgg accaacgact aatctaga               1368
```

<210> SEQ ID NO 33
<211> LENGTH: 1163
<212> TYPE: DNA
<213> ORGANISM: Escherichia coli

<400> SEQUENCE: 33

```
ggtacccata tgaaaaatat aactttcatt ttttttatt tattagcatc gccattatat      60
gcaaatggcg acagattata ccgtgctgac tcaagacccc cagatgaaat aaaacgttcc    120
ggaggtctta tgcccagagg gcataatgag tacttcgata gaggaactca atgaatatt    180
aatctttatg atcacgcgag aggaacacaa accggctttg tcagatatga tgacggatat    240
gtttccacta aacttagttt gagatctgct cacttagcag acagtctat attatcagga    300
tattccactt actatatata tgttatagcg acagcaccaa atatgtttaa tgttaatgat    360
gtattaggcg tatacagccc tcaccctat gaacaggagg tttctgcgtt aggcggaata    420
ccatattctc agatatatgg atggtatcgt gttaattttg gtgtgattga tgaacgatta    480
catcgtaaca gggagtatag agaccggtat tacagaaatc tgaatatagc ccggcagag    540
gatggttaca gattagcagg tttcccaccg gatcaccaag cttggagaga agaaccctgg    600
attcatcatg caccacaagg ttgtggaaat tcatcaagaa caatcacagg tgatacttgt    660
aatgaggaga cccagaatct gagcacaata tatctcaggg aatatcaatc aaaagttaag    720
```

```
aggcagatat tttcagacta tcagtcagag gttgacatat ataacagaat tcgggatgaa    780
ttatgaataa agtaaaatgt tatgttttat ttacggcgtt actatcctct ctatatgcac    840
acggagctcc ccagactatt acagaactat gttcggaata tcgcaacaca caaatatata    900
cgataaatga caagatacta tcatatacgg aatcgatggc aggcaaaaga gaaatggtta    960
tcattacatt taagagcggc gaaacatttc aggtcgaagt cccgggcagt caacatatag   1020
actcccagaa aaaagccatt gaaaggatga aggacacatt aagaatcaca tatctgaccg   1080
agaccaaaat tgataaatta tgtgtatgga ataataaaac ccccaattca attgcggcaa   1140
tcagtatgaa aaactagtct aga                                           1163

<210> SEQ ID NO 34
<211> LENGTH: 41
<212> TYPE: DNA
<213> ORGANISM: Escherichia coli

<400> SEQUENCE: 34
ggtacccata tgaatggcga cagattatac cgtgctgact c                       41

<210> SEQ ID NO 35
<211> LENGTH: 41
<212> TYPE: DNA
<213> ORGANISM: Escherichia coli

<400> SEQUENCE: 35
ggtaccatgg ggaatggcga cagattatac cgtgctgact c                       41

<210> SEQ ID NO 36
<211> LENGTH: 44
<212> TYPE: DNA
<213> ORGANISM: Escherichia coli

<400> SEQUENCE: 36
ggtaccatgg ctagcaatgg cgacagatta taccgtgctg actc                    44

<210> SEQ ID NO 37
<211> LENGTH: 26
<212> TYPE: DNA
<213> ORGANISM: Escherichia coli

<400> SEQUENCE: 37
gaattcggga tgaattatga tctaga                                        26

<210> SEQ ID NO 38
<211> LENGTH: 26
<212> TYPE: DNA
<213> ORGANISM: Escherichia coli

<400> SEQUENCE: 38
gaattcggga tgaattatga gagctc                                        26

<210> SEQ ID NO 39
<211> LENGTH: 29
<212> TYPE: DNA
<213> ORGANISM: Escherichia coli

<400> SEQUENCE: 39
gaattcggga tgaattatga tttatggct                                     29

<210> SEQ ID NO 40
```

-continued

```
<210> SEQ ID NO 40
<211> LENGTH: 29
<212> TYPE: DNA
<213> ORGANISM: Escherichia coli

<400> SEQUENCE: 40
gaattcggga tgaattatga catatggct                                    29

<210> SEQ ID NO 41
<211> LENGTH: 89
<212> TYPE: DNA
<213> ORGANISM: Escherichia coi

<400> SEQUENCE: 41
gaattcggga tgaattatga gggagaccac aacggtttcc cactagaaat aatttttgttt   60 aactttaaga aggagatata catatggct                                    89

<210> SEQ ID NO 42
<211> LENGTH: 28
<212> TYPE: DNA
<213> ORGANISM: Escherichia coli

<400> SEQUENCE: 42
gaattcagtt gtagggaggg atccatgg                                     28

<210> SEQ ID NO 43
<211> LENGTH: 385
<212> TYPE: DNA
<213> ORGANISM: Escherichia coli

<400> SEQUENCE: 43
catatgaata aagtaaaatg ttatgtttta tttacggcgt tactatcctc tctatatgca   60
cacggagctc cccagactat tacagaacta tgttcggaat atcgcaacac acaaatatat  120
acgataaatg acaagatact atcatatacg gaatcgatgg caggcaaaag agaaatggtt  180
atcattacat ttaagagcgg cgaaacattt caggtcgaag tcccgggcag tcaacatata  240
gactcccaga aaaagccat tgaaaggatg aaggacacat taagaatcac atatctgacc  300
gagaccaaaa ttgataaatt atgtgtatgg aataataaaa cccccaattc aattgcggca  360
atcagtatga aaactagtt ctaga                                         385

<210> SEQ ID NO 44
<211> LENGTH: 324
<212> TYPE: DNA
<213> ORGANISM: Escherichia coli

<400> SEQUENCE: 44
catatggctc cccagactat tacagaacta tgttcggaat atcgcaacac acaaatatat   60
acgataaatg acaagatact atcatatacg gaatcgatgg caggcaaaag agaaatggtt  120
atcattacat ttaagagcgg cgaaacattt caggtcgaag tcccgggcag tcaacatata  180
gactcccaga aaaagccat tgaaaggatg aaggacacat taagaatcac atatctgacc  240
gagaccaaaa ttgataaatt atgtgtatgg aataataaaa cccccaattc aattgcggca  300
atcagtatga aaactagtc taga                                          324

<210> SEQ ID NO 45
<211> LENGTH: 82
<212> TYPE: DNA
<213> ORGANISM: Escherichia coli

<400> SEQUENCE: 45
```

```
tctagataac ttcgtataat gtatgctata cgaagttatg aattcgaagc gcttggatac    60
agttgtaggg agggatccat gg                                              82
```

<210> SEQ ID NO 46
<211> LENGTH: 98
<212> TYPE: DNA
<213> ORGANISM: Escherichia coli

<400> SEQUENCE: 46

```
tctagaaatt aaccgatcga cgtgcaagcg gacatttatt ttaaattcga taatttttgc    60
aaaaacattt cgacatattt atttatttta ttcatatg                            98
```

<210> SEQ ID NO 47
<211> LENGTH: 45
<212> TYPE: DNA
<213> ORGANISM: Artificial Sequence
<220> FEATURE:
<223> OTHER INFORMATION: Primer

<400> SEQUENCE: 47

```
cgggtaccca tatgaaaaat ctggattgtt gggtcgacaa tgaag                    45
```

<210> SEQ ID NO 48
<211> LENGTH: 27
<212> TYPE: DNA
<213> ORGANISM: Artificial Sequence
<220> FEATURE:
<223> OTHER INFORMATION: Primer

<400> SEQUENCE: 48

```
cgtctagaaa ttaatcattt gtccatc                                        27
```

<210> SEQ ID NO 49
<211> LENGTH: 32
<212> TYPE: DNA
<213> ORGANISM: Artificial Sequence
<220> FEATURE:
<223> OTHER INFORMATION: Primer

<400> SEQUENCE: 49

```
cgggtaccca tatgaaaaac cttgattgtt gg                                  32
```

<210> SEQ ID NO 50
<211> LENGTH: 27
<212> TYPE: DNA
<213> ORGANISM: Artificial Sequence
<220> FEATURE:
<223> OTHER INFORMATION: Primer

<400> SEQUENCE: 50

```
gctctagatt agtcgttggt ccaacct                                        27
```

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51

```
tcacctgccg aatcaactag c                                              21
```

<210> SEQ ID NO 52

-continued

```
<211> LENGTH: 20
<212> TYPE: DNA
<213> ORGANISM: Artificial Sequence
<220> FEATURE:
<223> OTHER INFORMATION: Primer

<400> SEQUENCE: 52
gacttccctt gcctacattg                                              20

<210> SEQ ID NO 53
<211> LENGTH: 10
<212> TYPE: PRT
<213> ORGANISM: Escherichia coli

<400> SEQUENCE: 53

Met Asn Gly Asp Arg Leu Tyr Arg Ala Asp
 1               5                  10

<210> SEQ ID NO 54
<211> LENGTH: 11
<212> TYPE: PRT
<213> ORGANISM: Escherichia coli

<400> SEQUENCE: 54

Met Gly Asn Gly Asp Arg Leu Tyr Arg Ala Asp
 1               5                  10

<210> SEQ ID NO 55
<211> LENGTH: 12
<212> TYPE: PRT
<213> ORGANISM: Escherichia coli

<400> SEQUENCE: 55

Met Ala Ser Asn Gly Asp Arg Leu Tyr Arg Ala Asp
 1               5                  10

<210> SEQ ID NO 56
<211> LENGTH: 10
<212> TYPE: PRT
<213> ORGANISM: Escherichia coli

<400> SEQUENCE: 56

Met Arg Ala Pro Gln Thr Ile Thr Glu Leu
 1               5                  10

<210> SEQ ID NO 57
<211> LENGTH: 9
<212> TYPE: PRT
<213> ORGANISM: Escherichia coli

<400> SEQUENCE: 57

Met Ala Pro Gln Thr Ile Thr Glu Leu
 1               5
```

HIGH LEVEL EXPRESSION OF IMMUNOGENIC PROTEINS IN THE PLASTIDS OF HIGHER PLANTS

This application is a continuation-in-part of U.S. patent application Ser. No. 10/088,634, which claims priority under 35 U.S.C. §371 to International Application No. PCT/US00/25930 filed Sep. 21, 2000, which claims priority under 35 U.S.C. §119(e) to U.S. Provisional Applications 60/155,007 and 60/211,139 filed Sep. 21, 1999 and Jun. 13, 2000, respectively. This application also claims priority under 35 U.S.C. §119(e) to U.S. Provisional Applications 60/335,699, filed Oct. 25, 2001, and 60/279,591, filed Mar. 29, 2001.

FIELD OF THE INVENTION

This invention relates to the fields of transgenic plants and molecular biology. More specifically, DNA constructs and methods of use thereof are provided which facilitate the excision of target DNA sequences from transplastomic plants.

BACKGROUND OF THE INVENTION

Several publications and patent documents are referenced in this application by author name and year of publication in parentheses in order to more fully describe the state of the art to which this invention pertains. Full citations for these reference can be found at the end of the specification. The disclosure of each of these publications is incorporated by reference herein.

The plastid genetic system of higher plants is highly polyploid. For example, in a tobacco leaf there are as many as 100 chloroplasts, each carrying ~100 identical genome copies, a total of 10,000 copies in a leaf cell. High-level protein expression, lack of pollen transmission and the feasibility to engineer polycistronic expression units make the plastid genome an attractive alternative to nuclear engineering. Plastid transformation vectors often contain a selective marker, most commonly a spectinomycin resistance (aadA) gene, flanked by plastid DNA sequences targeting insertion of the marker gene by homologous recombination into the plastid gnome. Genes of commercial value but lacking a selectable phenotype are physically linked to the selective marker and the two genes are integrated together as a block of heterologous sequences. Plastid transformation is accomplished by biolistic DNA delivery or polyethylene glycol induced uptake of the transforming DNA followed by selection for the antibiotic resistance marker to ensure preferential propagation of plastids with transformed genome copies. As the result, all the 10,000 wild-type plastid genome copies in a cell are replaced with transgenic copies during a gradual process (Maliga, 1993).

Incorporation of a selectable marker gene is essential to ensure preferential maintenance of the transformed plastid genome copies. However, once transformation is accomplished, maintenance of the marker gene is undesirable. One problem may be the metabolic burden imposed by the expression of the selectable marker gene. For example FLARE-S, the product of the marker gene with good prospects to transform cereal chloroplasts, accumulates up to 18% of the total soluble cellular protein (Khan and Maliga 1999). The second problem is the relatively high potential for horizontal transfer of plastid marker genes to microbes (Tepfer 1989; Dröge et al. 1998; Sylvanen 1999), as commonly used plastid maker gene constructs are efficiently expressed in *E. coli* (Carrer et al. 1993; Svab and Maliga 1993). Therefore, having plastid marker genes in commercial products is undesirable.

SUMMARY OF THE INVENTION

In accordance with the present invention, methods and systems are provided which facilitate the manipulation of the plastid genomes of higher plants. The methods and systems of the invention may be employed to remove heterologous sequences from the plastid genome, such as selectable marker genes following successful isolation of transformed progeny. Alternatively, they may be designed to remove endogenous genes involved in plant cell metabolism, growth, development and fertility.

In one embodiment of the invention, a site specific recombination method for removal of predetermined nucleic acid sequences from the plastid genome is provided. The method comprises providing a first nucleic acid construct, the construct comprising a promoter being operably linked to a nucleic acid encoding an optional plastid targeting transit sequence which is in turn operably linked to a nucleic acid encoding a protein having excision activity, the construct further comprising a first selectable marker encoding nucleic acid having plant specific 5' and 3' regulatory nucleic acid sequences. The method also entails the use of a second DNA construct, the second construct comprising an second selectable marker encoding nucleic acid and excision sites. The second construct optionally contains a gene of interest and further comprises flanking plastid targeting nucleic acid sequences which facilitate homologous recombination into said plastid genome. The second DNA construct is introduced into plant cell and the cells are cultured in the presence of a selection agent, thereby selecting for those plant cells expressing the proteins encoded by said second DNA construct. The first DNA construct is then introduced into cells having the second construct in the presence of a selection agent and those plant cells expressing proteins encoded by said first construct are selected. If present, the excising activity acts on the excision sites, thereby excising said predetermined target sequence. Plants may then be regenerated from plant cells obtained by the foregoing method.

Proteins having excision activity suitable for the practice of the invention include, without limitation, CRE, flippase, resolvase, FLP, SSV1-encoded integrase, and transposase. Sequences corresponding to excision sites suitable for the practice of the inventin, include, for example, LOX sequences, and frt sequences.

A variety of selection of agents may be selected. These include without limitation, kanamycin, gentamycin, spectinomycin, streptomycin and hygromycin, phosphinotricin, basta, glyphosate and bromoxynil.

In an alternative embodiment, a site specific recombination method for removal of predetermined nucleic acid sequences from the plastid genome is provided. The method comprising providing a first nucleic acid construct, said construct comprising a regulated promoter being operably linked to a nucleic acid encoding an optional plastid targeting transit sequence which is operably linked to a nucleic acid encoding a protein having excision activity, said construct optionally further comprising a first selectable marker encoding nucleic acid having plant specific 5' and 3' regulatory nucleic acid sequences. A second DNA construct is also provided, said second construct comprising an second selectable marker encoding nucleic acid and excision sites, said second construct further comprising flanking plastid targeting nucleic acid sequences which facilitate homologous recombination into said plastid genome at a predetermined target sequence such that excision sites flank said predetermined target sequence following homologous recombination and introducing said second DNA construct into a plant cell. The plant cell so generated is then cultured in the presence of a selection agent, thereby selecting for those plant cells expressing the proteins encoded by said second DNA construct. A plant is then regenerated from cells containing the second construct and the first DNA construct is introduced into these cells in the presence of a selection agent and those plant cells expressing proteins encoded by said first construct are selected. The excising activity then acts on the excision sites, thereby excising said predetermined target sequence.

Regulatable promoters suitable for this embodiment of the invention include, without limitation, inducible promoters, tissue specific promoters, developmentally regulated promoters and chemically inducible promoters.

Candidate predetermined target sequences, may include for example genes associated with male sterility, clpP, ribosomal proteins, ribosomal operon sequences.

In yet a further embodiment of the invention compostions and methods are provided for expressing immunogenic proteins in selectable marker free plants. Exemplary immunogenic proteins include, without limitation the TetC protein from C. tetani and the heat labile enterotoxin from E. coli. DNA constructs useful in the methods of the present invention comprising operons containing a plurality of immunogenic proteins are also provided. Transgenic plants comprising the foregoing immunogenic proteeins are also within the scope of the invention.

BRIEF DESCRIPTION OF THE DRAWINGS

FIG. 8A: The codA region was amplified with the O1/O2 primers: the size of aadA-codA fragment is 2.0 kb; the coda deletion fragment is 0.7 kb (FIG. 4). FIG. 8B: Testing for cre sequences by PCR amplification with the Cre1/Cre3 oligonucleotides.

DETAILED DESCRIPTION OF THE INVENTION

Figure 1:
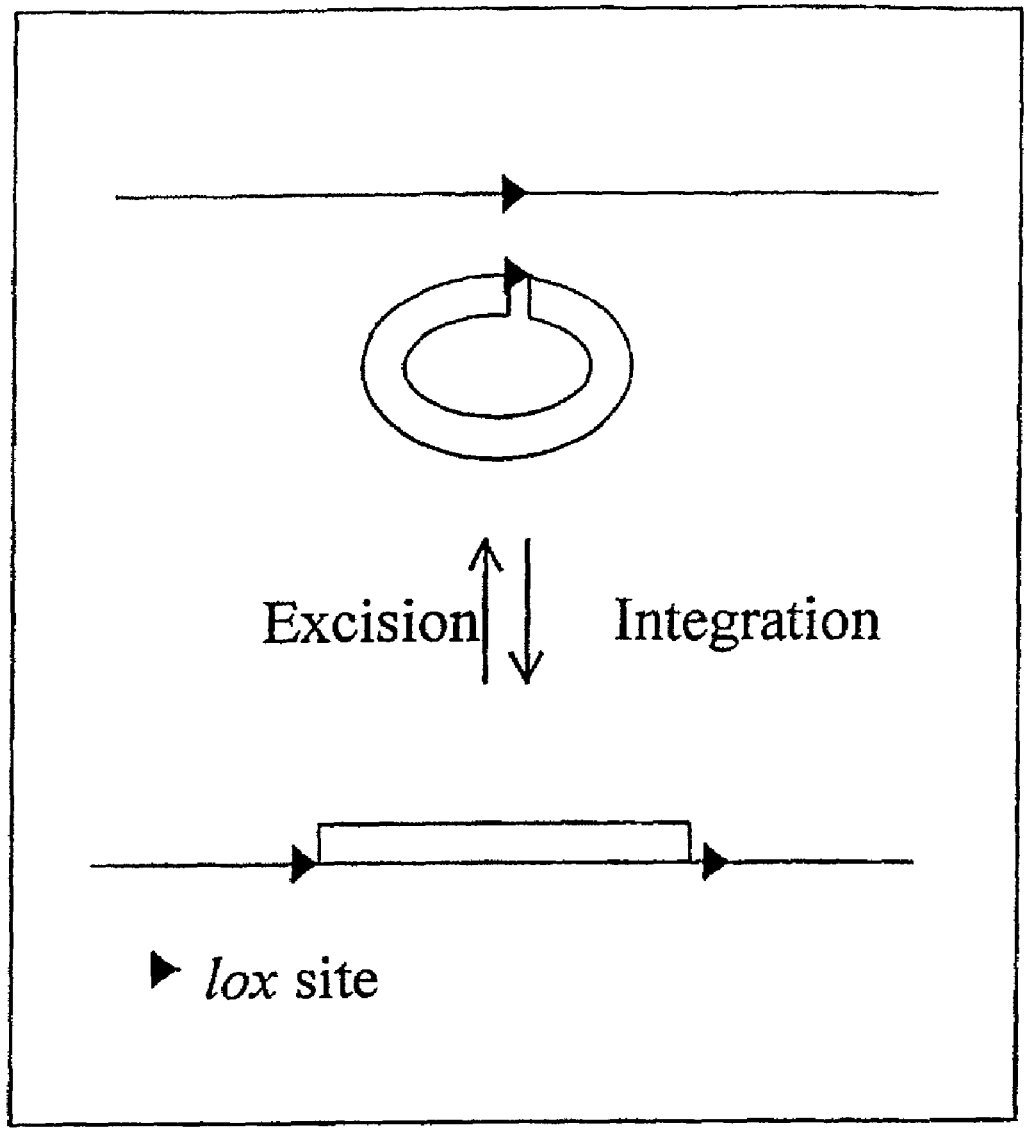
FIG. 1 is a schematic diagram depicting CRE-mediated excision and integration of DNA segments.

The following definitions are provided to aid in understanding the subject matter regarded as the invention.

Heteroplastomic refers to the presence of a mixed population of different plastid genomes within a single plastid or in a population of plastids contained in plant cells or tissues.

Homoplastomic refers to a pure population of plastid genomes, either within a plastid or within a population contained in plant cells and tissues. Homoplastomic plastids, cells or tissues are genetically stable because they contain only one type of plastid genome. Hence, they remain homoplastomic even after the selection pressure has been removed, and selfed progeny are also homoplastomic. For purposes of the present invention, heteroplastomic populations of genomes that are functionally homoplastomic (i.e., contain only minor populations of wild-type DNA or transformed genomes with sequence variations) may be referred to herein as "functionally homoplastomic" or "substantially homoplastomic." These types of cells or tissues can be readily purified to a homoplastomic state by continued selection.

Plastome refers to the genome of a plastid.

Transplastome refers to a transformed plastid genome.

Transformation of plastids refers to the stable integration of transforming DNA into the plastid genome that is transmitted to the seed progeny of plants containing the transformed plastids.

Selectable marker gene refers to a gene that upon expression confers a phenotype by which successfully transformed plastids or cells or tissues carrying the transformed plastid can be identified.

Transforming DNA refers to homologous DNA, or heterologous DNA flanked by homologous DNA, which when introduced into plastids becomes part of the plastid genome by homologous recombination.

An alternative type of transforming DNA refers to a DNA which contains recombination site sequences for a site-specific recombinase or integrase. Insertion of this type of DNA is not dependent of the degree of homology between the transforming DNA and the plastid to be transformed but rather is catalyzed by the action of the recombinase or integrase on the first and second recombination sites.

Operably linked refers to two different regions or two separate genes spliced together in a construct such that both regions will function to promote gene expression and/or protein translation. "Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

The terms "percent similarity", "percent identity" and "percent homology" when referring to a particular sequence are used as set forth in the University of Wisconsin GCG software program.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the production of a polypeptide coding sequence in a host cell or organism. Such expression signals may be combined such that production of said polypeptide occurs transiently or is produced stably over the life of the cell.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specfically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product. Amino acid residues described herein are preferred to be in the "L" isomeric form. However, residues in the "D" isomeric form may be substituted for any L-amino acid residue, provided the desired properties of the polypeptide are retained.

All amino-acid residue sequences represented herein conform to the conventional left-to-right amino-terminus to carboxy-terminus orientation.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion, biolistic bombardment and the like.

A "clone" or "clonal cell population" is a population of cells derived from a single cell or common ancestor by mitosis.

A "cell line" is a clone of a primary cell or cell population that is capable of stable growth in vitro for many generations.

Cre-Mediated Site Specific Recombination

The plastid genome of higher plants is present in 100–10,000 copies per cell. Incorporation of a selectable marker gene is essential to ensure preferential maintenance of the transformed plastid genome copies carrying useful genes with no selectable phenotype. However, once transformation is accomplished, maintenance of the marker gene is undesirable. In accordance with the present invention, a bacteriophage P1CRE-loxP site-specific recombination system is provided which is suitable for efficient elimination of marker genes from the plastid genome. The system exemplified herein has two components: a plastid tester strain carrying a cytosine deaminase (coda) transgene flanked by lox sites conferring sensitivity to 5-fluorocytosine and a nuclear CRE line carrying a nuclear-encoded, plastid-targeted CRE. Both the plastid tester (no CRE activity) and the nuclear CRE line (no lox sequence) were genetically stable. However, coda was eliminated at a very fast rate when the plastid-targeted CRE was introduced into the plastid tester strain by transformation or crossing. The gene for the nuclear-encoded CRE was subsequently separated from the transformed plastids by segregation in the seed progeny. Excision of coda by CRE was often accompanied by deletion of a plastid genome segment flanked by short directly repeated sequences. Removal of the antibiotic resistance marker from the transplastomic plants eliminates the metabolic burden imposed by the expression of the selectable marker gene and should also improve public acceptance of the transgenic crops. Additional applications of the CRE-lox site-specific recombination system are activation of plastid gene expression by deletion or inversion of plastid genome sequences and induction of controlled cell death by deleting vital genes in the male reproductive tissue.

Although the use the CRE recombinase is exemplified herein, other prokaryotic and eukaryotic site-specific recombinases would be equally suitable for the elimination of the marker genes.

Recently, several prokaryotic and lower eukaryotic site-specific recombination systems have been shown to operate successfully in higher eukaryotes. In plant and animal cells functional site-specific recombination systems from bacteriophages P1 (Cre-lox) Mu (Gin-gix), and from the inversion plasmids of *Saccharomyces cerevisiae* (FLP-frt) (Morris et al. 1991; O'Gorman et al. 1991; Lichtenstein and Barrena 1993; Lyznik et al. 1993; Lyznik et al. 1995; Lyznik et al. 1996) and *Zygosaccharomiyces rouxii* (R-RS). In each of these systems, no additional factor aside from the recombinase and target sequences is required for recombination. Reviewed in van Haaren and Ow, 1993. The CRE-loxP site-specific recombination system of bacteriophage P1 has been studied extensively in vitro and in *E. coli* (Craig 1988; Adams et al. 1992). Expression of the CRE protein (38.5 kDa) is sufficient to cause recombination between 34 bp loxP sites that consist of 13 bp inverted repeats separated by 8 bp asymmetric spacer sequence. If there are two loxP sites within a DNA segment, the result of the recombination reaction depends on the relative position of the recombination sites. If the recombination sites form a direct repeat, that if they are in the same orientation, recombination results in deletion of the intervening DNA. If the recombination sites are in an inverted orientation, CRE-mediated recombination results in an inversion of the intervening DNA. The products of these reactions are shown in FIG. 1. The CRE site-specific recombination system has been employed for the elimination of nuclear genes in a number of eukaryotic systems, including higher plants (Dale and Ow 1991; Russell et al. 1992; Srivastava et al. 1999).

Before the present invention, the efficiency of CRE-mediated elimination of targeted plastid genes was unknown. To explore this system for this purpose, CRE-mediated elimination of the coda gene encoding cytosine deaminase (CD; EC 3.5.4.1) was assessed. Cytosine deaminase converts 5-fluorocytosine (5FC) into 5-fluorouracil (5FU), the precursor of 5-fluoro-dUMP. 5FC is lethal for CD-expressing cells due to irreversible inhibition of thymidylate synthase by 5-fluoro-dUMP (Beck et al. 1972). Cytosine deaminase is absent in plants. Expression of the bacterial coda in plastids renders cells sensitive to 5FC, while cells deficient in transgene expression are resistant (Serino and Maliga 1997). Thus, 5FC resistance could be used for positive identification of cells with CRE-induced coda deletion, even if such deletion events were relatively rare. The test system of the present invention incorporates a coda gene in the tobacco plastid genome between two directly oriented lox sites (>codA>). The transplastome was stable in the absence of CRE activity. However, highly efficient elimination of >codA> was triggered by introduction of a nuclear-encoded plastid-targeted CRE.

EXAMPLE 1

Cre-Mediated Deletion of the Selectable Plastid Marker

Cre-mediated deletion of the selective plastid marker in the plastids of tobacco somatic cell is described in Example I. The selectable marker flanked by the lox sites is exemplified here by coda. However, it could be any other selectable and non-selectable marker gene, or any DNA sequence independent of information content flanked by lox sites in the palstid genome. Components of the test stystem are tobacco plants carrying a coda coding region flanked by lox sites (>codA>). A second component of the test system is a nuclear gene encoding a plastid targeted CRE-site specific recombinase. Deletion of a plastid encoded >coda> is achieved by introducing nuclear Cre into the nucleus of somatic (leaf) tobacco cells by Agrobacterium-mediated transformation. Alternatively, the nuclear encoded Cre gene may be introduced by fertilization with pollen of an appropriate activator-of-deletion strain. The nuclear Cre gene is subsequently removed by segregation in the seed progeny.

Materials and Methods for the Practice of Example 1

The following materials and methods are provided to facilitate the practice of Example 1.

Plastid Coda with Direct lox Sites.

Figure 2:
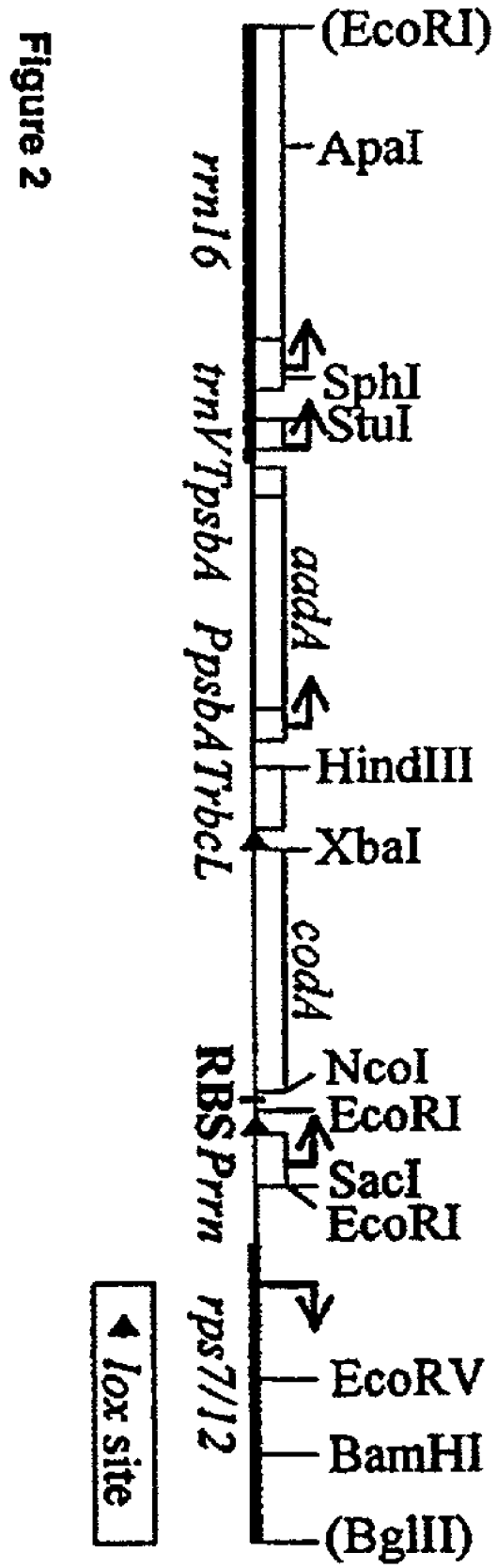
FIG. 2 is a map of a plastid transformation vector pSAC48, with coda bracketed by direct loxp sites. Positions of plastid genes rrn16, trnV, rps12/7 (Shinozaki et al. 1986), the aadA and coda transgenes and relevant restriction sites are marked.

The coda gene is contained in a SacI-HindHIII fragment. The gene map is shown in FIG. 2. PrrnloxD (SEQ. ID NO: 4) is a plastid rRNA operon (rrn16) promoter derivative. It is contained in a SacI-EcoRI fragment obtained by PCR using oligonucleotides 5'-GGGGAGCTCGCTCCCCCGC-CGTCGTTCAATG-3' (SEQ ID NO: 14) and 5'-GGGAAT-TCATAACTTCGTATAGCATACATTATACGAAGTTAT GCTCCCAGAAATATAGCCA-3' (SEQ ID NO: 15) as primers and plasmid pZS176 (progenitor of plasmid pZS197; Svab and Maliga 1993) as a template. The promoter fragment PrrnloxD contains a lox site at the 3' end adjacent to the EcoRI site. The EcoRI-NcoI fragment contains the ribosome binding site from plasmid pZS176. The fragment was obtained by annealing the complementary oligonucleotides 5'-AATTCGAAGCGCTTGGATACAGT-TGTAGGGAGGGATC-3' (SEQ ID NO: 16) and 5'-CATG-GATCCCTCCCTACAACTGTATCCAAGCGCTTCG-3' (SEQ ID NO: 17). The codA coding region is contained in an NcoI-XbaI fragment (Serino and Maliga 1997). The TrbcLloxD (SEQ. ID NO: 5) is the rbcL 3'-untranslated region contained in an XbaI-HindIII fragment obtained by PCR using oligonucleotides 5'-GGTCTAGATAACTTCG-TATAATGTATGCTATACGAAGTTATAGA-CATTAGCAGATA AATT-3' (SEQ ID NO: 18) and 5'-GGGGGTACCAAGCTTGCTAGATTT TGTATTTCAAATCTTG-3' (SEQ ID NO: 19) and plasmid pMSK48 (Khan and Maliga 1999) as template. TrbcLloxD contains a lox site adjacent to the XbaI site in direct orientation relative to the lox site in the coda 5' UTR. The chimeric PrrnloxD:codA:TrbcloxD gene was introduced into the tobacco plastid transformation vector pPRV111B (Zoubenko et al. 1994) as a SacI-HindIII fragment to obtain plasmid pSAC48.

Figure 3:
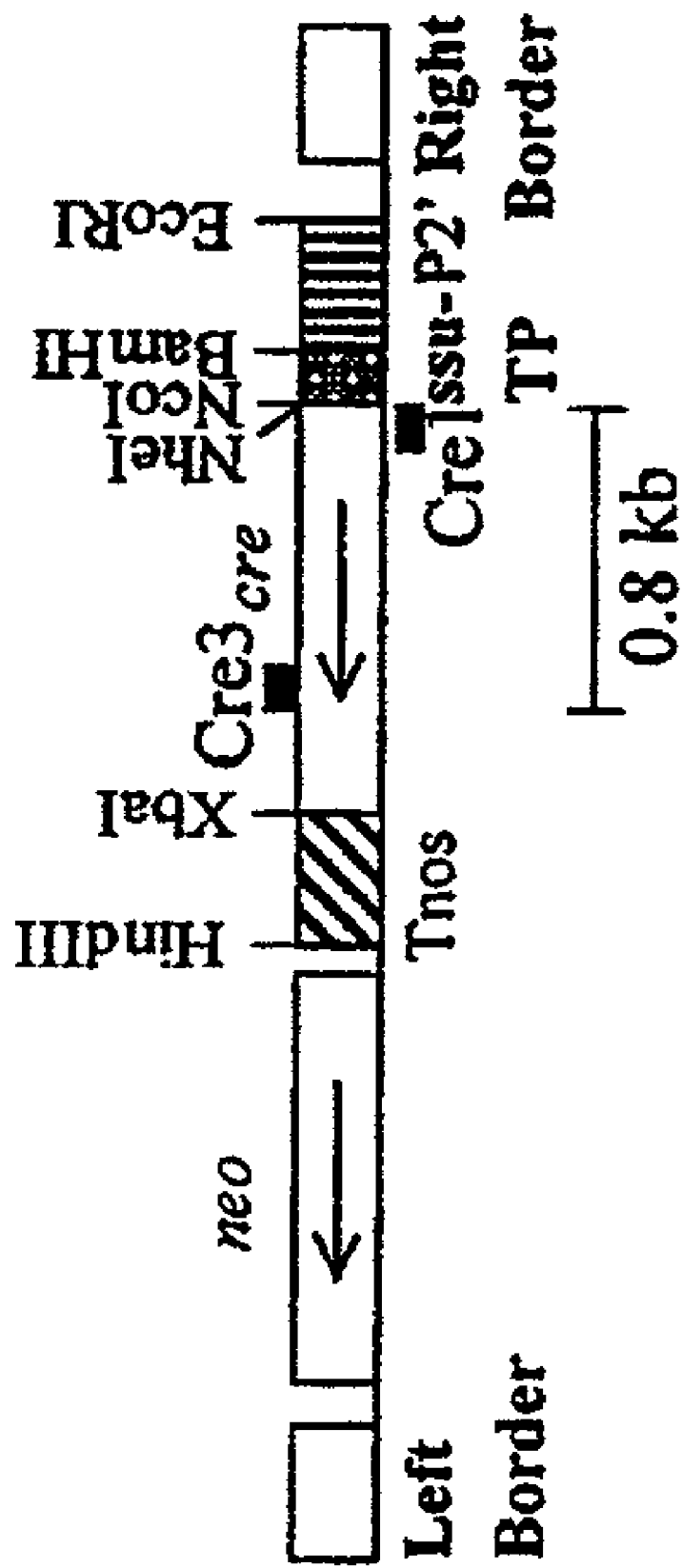
FIG. 3 is a map of an *Agrobacterium* binary vector pPZP212 with a plastid-targeted Ssu-tp-cre gene. Marked are: *Agrobacterium* Left and Right Border fragments; the kanamycin resistance (neo) gene; P2' promoter; SSU transit peptide (ssu-tp); cre coding region; recognition sequences for restriction enzymes BamHI, EcoRI, HindIII, NcoI, NheI and XbaI.

Plastid-targeted nuclear cre linked to a nuclear kanamycin resistance gene. Two plastid targeted nuclear cre genes were tested. The cre gene in *Agrobacterium* binary vector pKO27 and pKO28 encode the CRE recombinase at its N terminus translationally fused with the pea Rubisco small subunit (SSU) chloroplast transit peptide (Timko et al. 1985) and twenty two and five amino acids of the mature Rubisco small subunit, respectively. Both cre genes are contained in an EcoRI-HindIII fragment. The schematic map of the genes is shown in FIG. 3. The P2' *Agrobacterium* promoter (Velten et al. 1984) (SEQ ID NO: 9) is contained in an EcoRI-NcoI fragment. The P2' promoter fragment was obtained by PCR using oligonucleotides 5'-cc gaattcCATTTTCACGTGTGGAAGATATG-3' (SEQ ID NO: 20) and 5'-ccccatggtaggatcctatCGATTTGG TGTATC-GAGATTGG-3' (SEQ ID NO: 21) as primers and plasmid pHC1 (Carrer et al. 1990) as template. PCR amplification introduced an EcoRI site at the 5' end and ClaI, BamHI and a NcoI sites at the 3'end. A T introduced between the ClaI and the BamHI sites eliminates an ATG and introduces an in-frame stop codon (Sriraman 2000). The Rubisco SSU transit peptides are included in BamHI-NcoI fragments. The pKO27 fragment (Pea SSU-TP22; Sequence ID No. 7) was obtained by using oligonucleotides 5'-CCGGA TCCAAT-TCAACCACAAGAACTAAC-3' (SEQ ID NO: 22) and 5'-GGGGCTAGCCATGGCAGGCCACACCTG-CATGCAC-3' (SEQ ID NO: 23) as primers and plasmid pSSUpGEM4 as the template (Timko et al. 1985). The pKO28 fragment (Pea SSU-TP5; SEQ ID NO: 6) was obtained by using oligonucleotides 5'-CCGGATC CAAT-TCAACCACAAGAACTAAC-3' (SEQ ID NO: 22) and 5'-GGGGCTAGCCATGGTCAATGGGTTCAAATAGG-3' (SEQ ID NO: 24) as primers and plasmid pSSUpGEM4 as the template (Timko et al. 1985). A pea SSU-TP with 23 amino acids of the mature polypeptide is shown in SEQ ID NO: 8. The cre coding region included in a NcoI-XbaI fragment (SEQ ID NO: 3) was obtained by PCR amplification using the Cre1 5'-GGGGAGCTCCATGGCTAGCTC-CAATTTACTGACCGTACAC-3' (SEQ ID NO: 25) and Cre2 5'-GGGTCTAGACTAATCGCCATCCTCGAGCA GGCGCACCATTGC-3' (SEQ ID NO: 26) oligonucleotides as primers and DNA isolated from *Escherichia coli* strain BNN132 (ATCC number 47059) as template. The presence of cre gene in plant nuclear DNA was confirmed by PCR amplification with the Cre 1 and Cre3 oligonucleotides. The sequence of Cre3 oligonucleotide is 5'-TCAATCGAT GAGTTGCTTC-3' (SEQ ID NO: 27). The *Agrobacterium* nos terminator (Tnos) is included in a XbaI-HindIII fragment (Svab et al. 1990). The plastid targeted nuclear cre genes were introduced as EcoRI-HindIII fragments into the pPZP212 *Agrobacterium* binary vectors (Hajdukiewicz et al. 1994) to obtain plasmids pKO27 and pKO28 with twenty two and five amino acids of the mature Rubisco SSU. A schematic map of the *Agrobacterium* vectors is shown in FIG. 3.

Transgenic plants. Plastid transformation using the biolistic protocol, selection of transplastomic tobacco clones (RMOP medium, 500 mg/L spectinomycin dihydrochloride) and characterization of the transplastomic clones by DNA gel blot analysis was described (Svab and Maliga 1993). Transformation with *Agrobacterium* vectors pKO28 or pKO27 and regeneration of transformed tobacco plants has also been reported (Hajdukiewicz et al. 1994). Briefly, nuclear gene transformants were selected by kanamycin resistance on RMOP shoot regeneration medium containing 100 mg/L kanamycin and 500 mg/L carbenicillin. Kanamycin resistance of the shoots was confirmed by rooting on plant maintenance (RM) medium containing 100 mg/L kanamycin. Testing of 5FC cytotoxicity was carried out on RMPO medium according to published procedures (Serino and Maliga 1997).

Transplastomic Tobacco Plants with a Coda Gene Flanked by Direct lox sites.

Plastid transformation vector pSAC48 carries a codA gene in which two lox sites flank the coding region in a direct orientation. If the coda coding region is deleted via the lox sites, a lox site flanked by the promoter (Prrn) and terminator (TrbcL) are left behind. The selective marker in pSAC48, a pPRV111B vector derivative, is a spectinomycin resistance (aadA) gene (FIG. 2). Transformation with plasmid pSCAC48 yielded a number of independently transformed transplastomic lines, of which four were purified to the homoplastomic state: Nt-pSAC48-21A, Nt-pSAC48-16C, Nt-pSAC48-16CS and Nt-pSAC48-9A. These lines are considered identical other than they have been generated independently. A uniform population of transformed plastid genomes in the transplastomic plants was verified by DNA gel blot analysis (see below).

Nuclear-encoded Plastid-targeted Cre Genes.

To activate deletion of the plastid >coda> gene we introduced an engineered cre gene into the nucleus of the transplastomic lines encoding a plastid-targeted CRE. Targeting of nuclear-encoded plastid proteins is by an N-terminal transit peptide (TP) cleaved off during import from the cytoplasm into plastids (Soll and Tien, 1998). To ensure plastid targeting of the CRE recombinase, it was translationally fused with the Rubisco small subunit (SSU) transit peptide (Timko et al. 1985). Therefore, the product of the protein fusion is SSU-TP-CRE. Efficiency of import of chimeric proteins depends on the size of mature protein N-terminus incorporated in the construct (Wasmann et al. 1986; Lubben et al. 1989). Two chimeric cre genes (Ssu-tp-cre) were prepared, one with 5 (vector pKO28) and one with 22 (plasmid pKO27) amino acids of the mature SSU N-terminus, encoding SSU-TP5-CRE and SSU-TP22-CRE, respectively. These genes are also referred to as Cre1 and Cre2, respectively (Table 1). The cre genes were expressed in the P2' promoter and Tnos terminator cassettes in the Agrobacterium pPZP212 binary vector which carries kanamycin resistance (neo) as a selectable marker (FIG. 3).

Tobacco plant transformed with Ssu-tp5-cre (pKO37)and Ssu-tp22-cre (pKO26) were also obtained. In these plants the nuclear cre is expressed from the cauliflower mosaic virus 35S promoter (SEQ ID NO: 10) Timmermans et al. 1990.

| Line | Plastid genotype[a] | Nuclear marker |
|---|---|---|
| Wild-type | trnV+ aadA− codA− | |
| Nt-pSAC48-21A | trnV+ aadA+ codA+ | |
| Nt-pSAC48-16C | | |
| Cre1-1 | trnV+ aadA+ codA− | neo |
| | trnV− aadA− codA− | |
| Cre1-2 | trnV+ aadA+ codA− | neo |
| | trnV− aadA− codA− | |
| Cre1-3 | trnV+ aadA− codA− | neo |
| Cre1-4 | trnV− aadA− codA− | neo |
| Cre1-10 | trnV− aadA− codA− | neo |
| Cre2-1 | trnV+ aadA+ codA− | neo |
| Cre2-2 | trnV+ aadA+ codA− | neo |
| | trnV+ aadA*+ codA− | |
| | trnV− aadA− codA− | |
| Cre2-3 | trnV+ aadA+ codA+ | neo |
| | trnV+ aadA+ codA− | |
| | trnV+ aadA*+ codA− | |
| | trnV− aadA− codA− | |
| Cre2-4 | trnV+ aadA+ codA− | neo |
| Cre2-5 | trnV+ aadA+ codA− | neo |
| Cre2-10 | trnV+ aadA+ codA− | neo |
| | trnV− aadA− codA− | |
| Cre1-100 | trnV+ aadA− codA− | neo |
| Cre2-100 | trnV+ aadA− codA− | neo |
| Cre2-200 | trnV+ aadA− codA− | neo |
| Cre2-300 | trnV+ aadA− codA− | neo |

[a]presence or absence of plastid gene is indicated by + or −. Since the plastid trnV gene is deleted in some of the lines, the wild-type plastid genotype is trnV+ aadA− codA−.

Deletion of codA from the Plastid Genome in Somatic Cells.

To test the efficiency of CRE-mediated deletion in somatic cells, the Ssu-tp-cre genes were introduced into the nucleus of the transplastomic >codA> lines by cocultivation of *Agrobacterium* and tobacco leaf disks. Plants representing 11 individual Ssu-tp-cre insertion events have been characterized. Five lines (Cre1-derivatives) were obtained by transformation with Ssu-tp5-cre gene (vector pKO28) and six lines (Cre2-derivatives) were obtained by transformation with the Ssu-tp22-cre (vector pKO27) (Table 1).

Deletion of coda was first tested in a DNA sample taken from one leaf of eleven kanamycin resistant shoots representing an individual integration event of the nuclear Cre gene. Subsequently, 4 to 7 additional leaves were sampled from six shoots to confirm that the result of the analysis is typical for the plant.

The initial DNA samples were first screened for the loss of >codA> by PCR using the O1/O2 primer pair complementary to sequences in the aadA coding region N terminus and the coda promoter (FIG. 4A). Amplification with these primers yields a ~0.7-kb fragment if >coda> is deleted and a ~2.0-kb fragment if the >coda> gene is still present. Ethidium bromide stained gels of PCR products in FIG. 5 indicate complete loss of >coda> in each of the samples. A perfect, reconstituted lox site between Prrn and TrbcL was confirmed in eight clones by PCR amplification of the region with primers O1/O4 from the same DNA samples and direct sequencing of the amplification product with primer O2 (not shown). In two clones (Cre1-4, Cre1-10) a fragment is missing due to deletion of aadA alongside with coda (see below).

Figure 4:
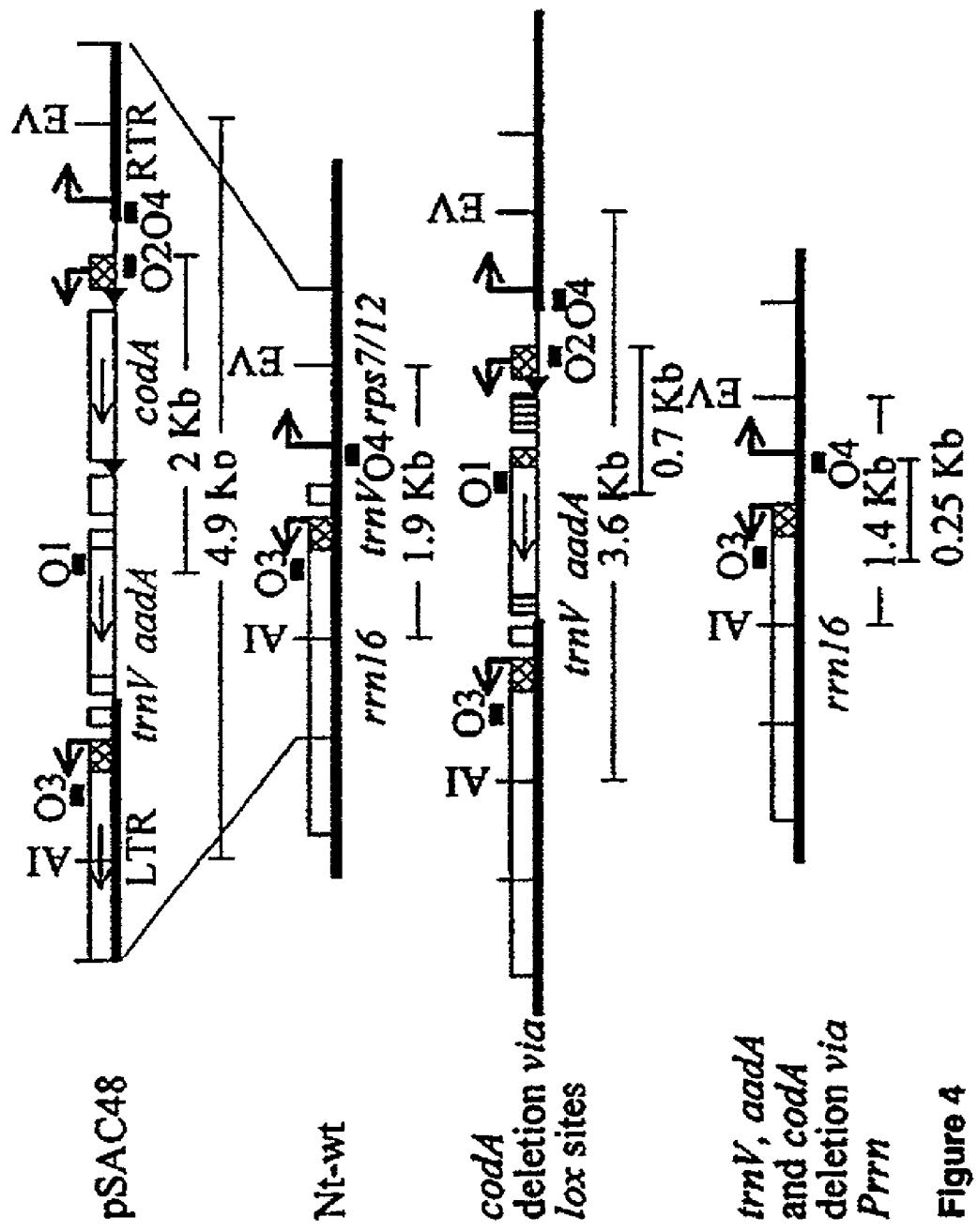
FIG. 4 shows maps of the plastid genome >codA> deletion derivatives. Shown are the plastid targeting region of vector pSAC48; the map of same region of the wild-type plastid genome (Nt-wt); the map of the plastid genome with CRE-mediated deletion of coda via the lox sites; and the map of the plastid genome with deletion via Prrn sequences lacking trnV, aada and cod. Positions of plastid genes rrn16, trnV and rps12/7 (Shinozaki et al. 1986), aada and coda transgenes, primers (O1–O4) and relevant restriction sites (AI, ApaI; EV, EcoRV) are marked.
Figure 5:
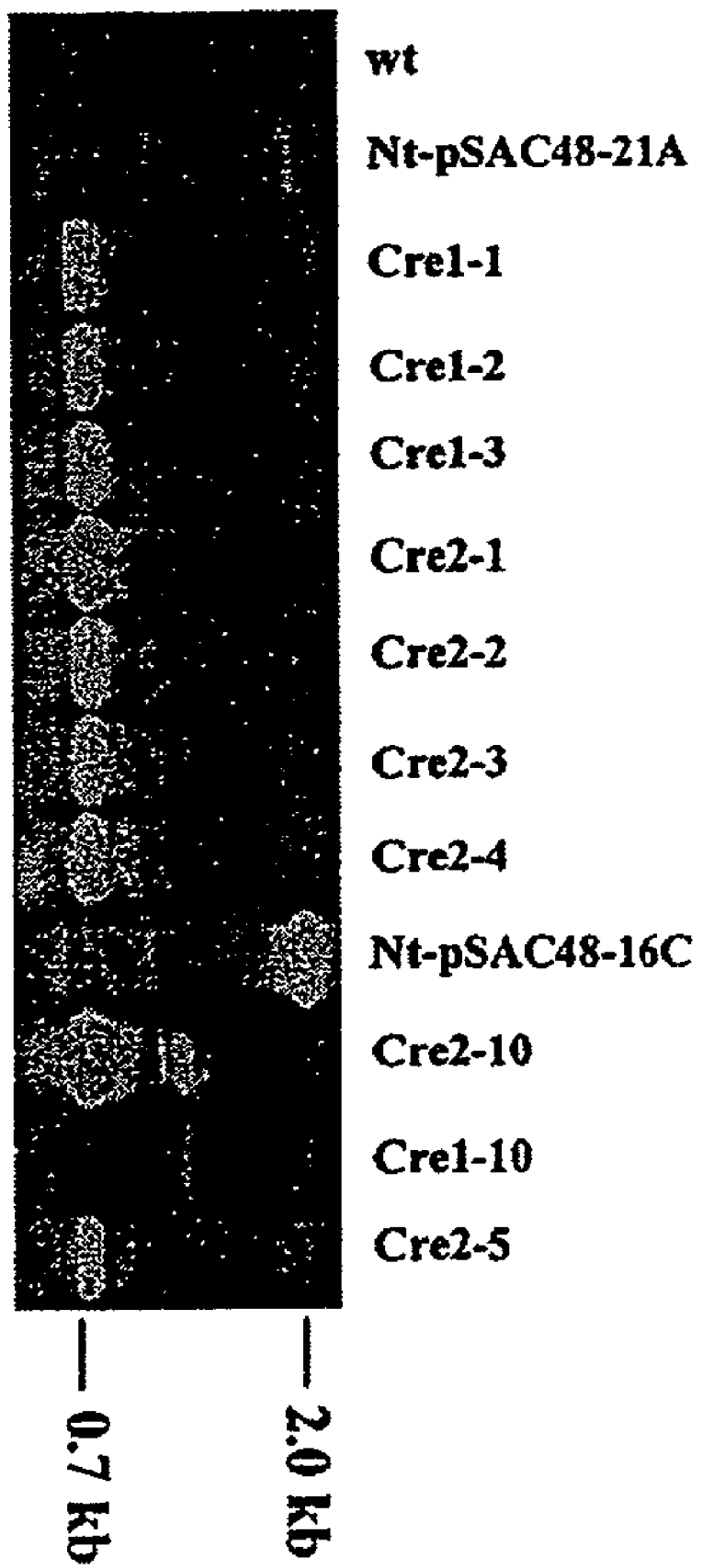
FIG. 5 is a gel showing PCR amplification which confirms CRE-mediated deletion of coda from the plastid genome. Primers O1 and O2 (FIG. 3) amplified the 0.7-kb fragment of the deleted region. Same primers amplify the 2.0-kb aadA-codA fragment in tester lines Nt-pSAC48-21A and Nt-pSAC-16C (no transgenic Cre gene). No specific fragment was obtained in wild-type DNA sample and in Cre1-10 line. The lines obtained are listed in Table 1.
Figure 6:
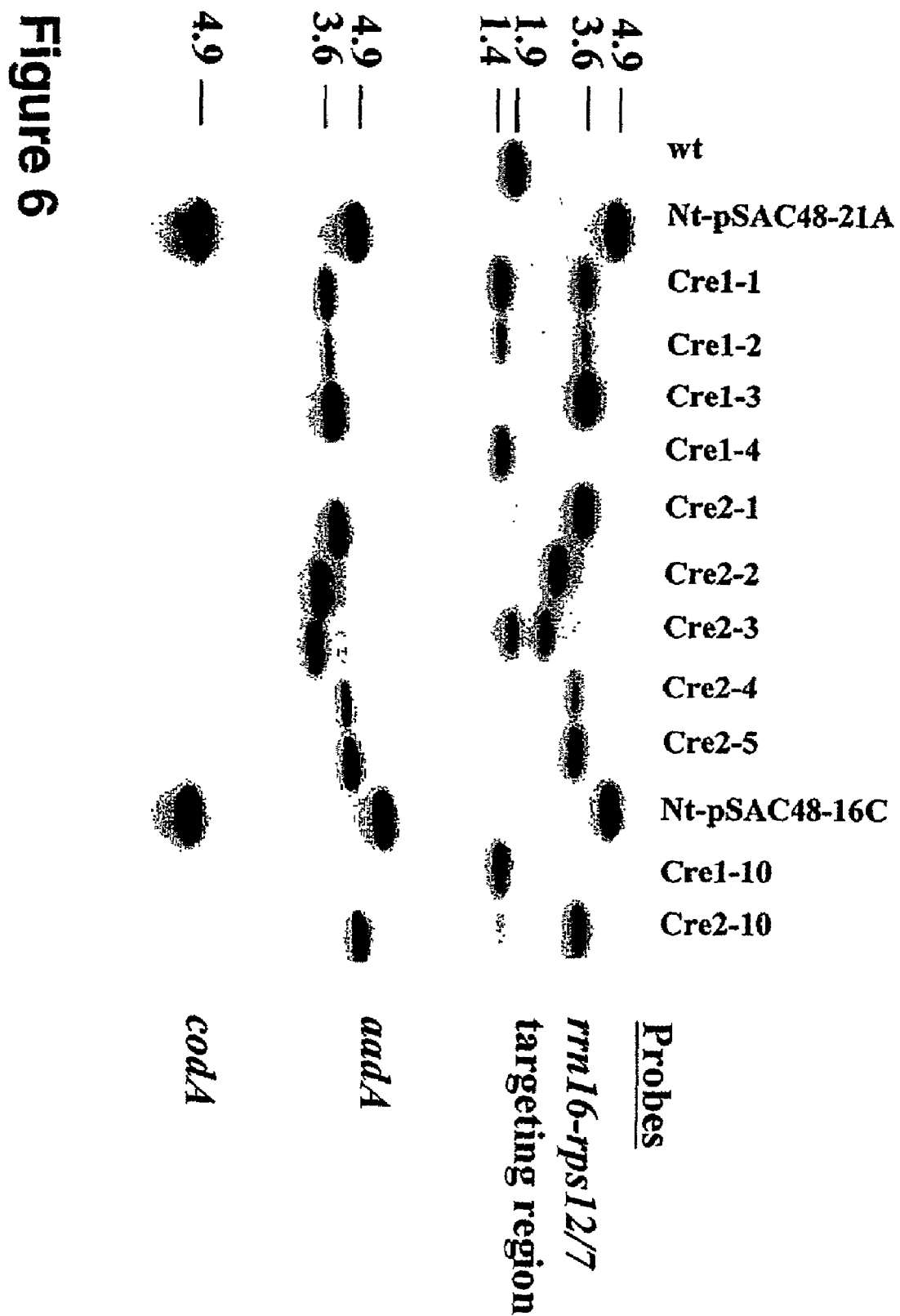
FIG. 6 shows the results of DNA gel blot analysis wherein plastid genome structure was determined in the indicated plant samples. Total cellular DNA was isolated from the leaves of plants listed in Table 1 and digested with the ApaI and EcoRV restriction endonucleases. The probes were the wild-type ApaI-EcoRV plastid targeting region and the aadA (NcoI-XbaI fragment) and codA (NcoI-XbaI fragment) coding regions. The hybridizing fragments are marked in FIG. 3.

Plastid genome structure in the initial DNA sample was determined by gel blot analysis of ApaI-EcoRV digested total cellular DNA. The probes were the plastid targeting region and the aadA and coda coding regions. The DNA gel blots are shown in FIG. 6. The maps of the parental genomes and deletion derivatives that help to interpret these genomes are shown in FIG. 4. In the plastid tester strains expressing no CRE (Nt-pSAC48-21A, Nt-pSAC48-16C) all three probes hybridized to the same 4.9-kb DNA fragment consistent with both coda and aadA being present in all the plastid genome copies. In the SSU-TP-CRE expressing plants no 4.9-kb fragment was detectable indicating the dramatic speed by which the >coda> gene was eliminated from the plastid genome. CRE-mediated deletion of >codA> via the lox sites yielded the 3.6-kb fragment detected in nine of the eleven clones. The 3.6-kb fragment was the only product detected in four clones, and was present in a heteroplastomic population in five clones. Unanticipated was formation of a 1.4-kb ApaI-EcoRV fragment in five clones. DNA gel blot analysis confirmed that this fragment lacks both coda and aadA, and is smaller than the wild type ApaI-EcoRV fragment (1.9-kb). Direct sequencing of PCR products in this region confirmed deletion of cod, aadA and trnV by homologous recombination via the duplicated Prrn promoter regions. One of the Prrn promoters is driving cod, the other is upstream of the rRNA operon at its native location. Deletion of trnv is the reason why the ApaI-EcoRV fragment derived from this region (1.4-kb) is smaller than the wild-type fragment (1.9-kb).

Figure 7:
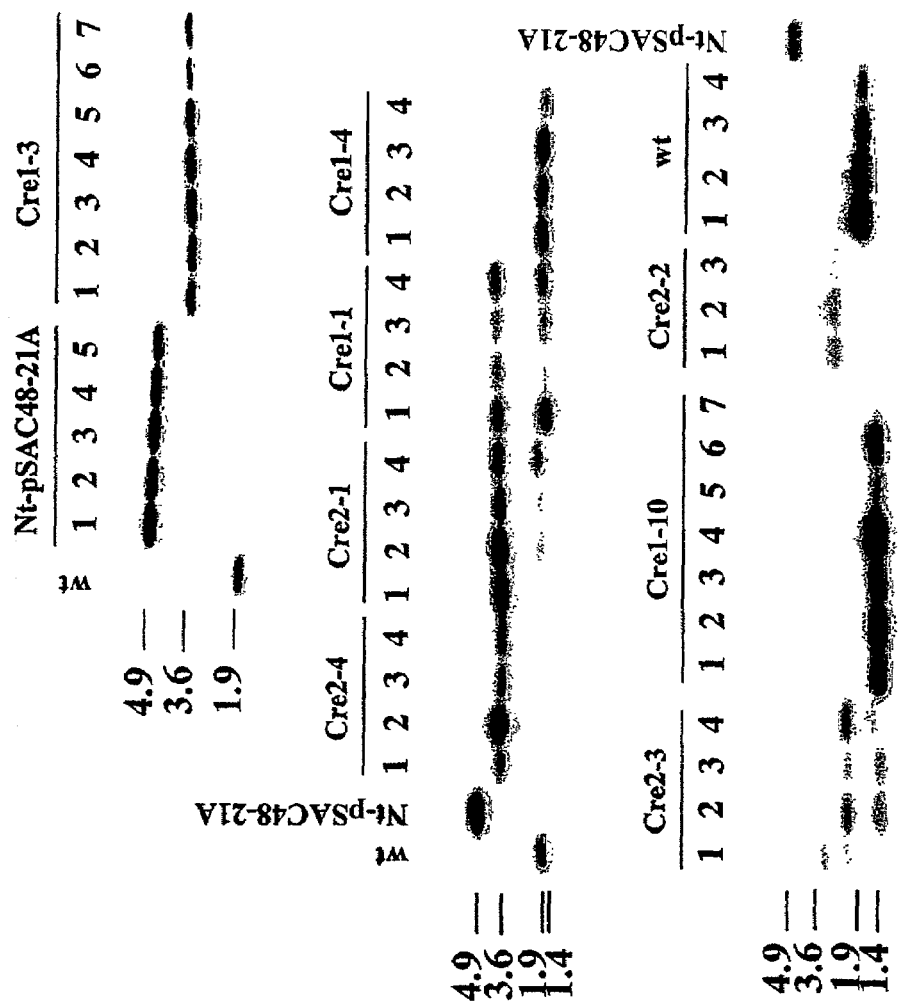
FIG. 7 are gels showing uniformity of plastid genome populations in the Ssu-tp-cre transformed plants. Total cellular DNA extracted from several leaves was probed with the ApaI-EcoRV targeting region probe. Numbers identify leaves from which DNA was extracted. For example, seven different leaves were probed from the Cre1-3 plant. For details, see Brief Description of FIG. 6.

The initial DNA samples were taken from one leaf of a plant obtained by rooting the shoot obtained after transformation with the Ssu-tp-cre genes. To confirm that the DNA samples extracted from the leaf were typical for the plant, we have sampled several more leaves from the same plants (FIG. 7). In four clones coda was excised by CRE via the lox sites, and the shoots were homoplastomic for the deleted genome. Two of these, Cre1-3 and Cre2-4 were further characterized by testing seven and four additional leaves of the same plants, respectively. DNA gel blot analysis of these samples confirmed a uniform deletion of >coda> from all genome copies. These plants are the desired final products carrying the desired plastid transgenes and lacking the undesirable selective marker. These plants and their progeny can be used directly for the production of recombinant proteins as they are free from the selectable marker gene. Furthermore, these plants are a source of engineered chloroplasts for introduction into breeding lines by sexual crossing. The seed progeny of the plants is segregating for the Ssu-tp-cre activator gene. Plants with the desired chloroplasts but lacing the activator gene can be identified by PCR testing for cre sequences. Alternatively, individuals lacking cre can be identified in the seed progeny by sensitivity to kanamycin, since the Ssu-tp-cre genes in the pKO27 and pKO28 *Agrobacterium* vectors are physically linked to kanamycin resistance (neo gene; FIG. 3). In two clones, Cre1-4 and Cre1-10, deletion of trnV (encoding tRNA-Val$^{GAC}$), aadA and coda occurred by homologous recombination via the duplicated Prrn promoter region. The Cre1-10 plant is homoplastomic for the deletion based on probing seven additional leaves (FIG. 7). Apparently, the one remaining trnv gene encoding tRNA-Val$^{UAC}$ is sufficient for the translation of all valine codons, or there is import of tRNA-Val$^{GAC}$ from the cytoplasm. In the Cre1-4 clone some of the leaves (two out of four) contained residual genome copies with trnV and aadA.

In five clones the initial DNA samples contained more than one type of plastid genome copies. Mixed populations of plastid genome populations were confirmed in all parts of the plants by testing additional leaves (FIG. 7). Genetically stable coda deletion lines can be obtained from these heteroplastomic plants by testing plants regenerated from single somatic cells or individual seedlings in a segregating seed progeny.

Deletion of coda from the Plastid Genome in the Seed Progeny.

CRE-mediate deletion of the negative plastid marker coda in somatic cells was described in the previous section. Deletion of the plastid marker gene in the somatic cells of the transplastomic plants, without going though a sexual cycle, is highly desirable to accelerate the production of marker-free transplastomic plants. However, this approach is feasible only if there is a system for tissue culture and plant regeneration from somatic cells. Such system is unavailable for the economically important cereal crops rice and maize. As an alternative to transformation of somatic cells, we developed CRE activator lines carrying a nuclear-encoded plastid-targeted Cre to be used as the source of Cre gene when used as a pollen parent. The tobacco CRE activator lines were obtained by transforming the nucleus of wild-type plants with SSU-TP-CRE constructs. Lines in which the Cre is linked to a nuclear kanamycin resistance gene in a wild-type cytoplasm are Cre1-100, Cre-2-100, Cre2-200 and Cre2-300 (Table 1).

To activate deletion of >coda> in the seed progeny, tester plants Nt-pSAC48-21A and Nt-pSAC48-16C were emasculated to prevent self fertilization, and fertilized with pollen from the Cre2-200 and Cre2-300 activator lines. The activator lines are primary transgenic plants ($T_0$) segregating for the Ssu-tp-cre gene. Therefore, a proportion of the seed progeny derived from the cross will have the activator genes while others will not. If the coda gene is present, the O1/O2 primer pair marked in FIG. 4 amplifies a 2.0-kb fragment. If the coda gene is absent, the same primers will amplify a 0.7-kb fragment. PCR analysis shown in FIG. 8 confirmed CRE-mediated deletion of >coda> in seedlings. The Cre1-100, Cre2-100 and Cre2-300 activator lines are apparently expressing CRE efficiently, indicated by the presence of only of the 0.7-kb fragment in seedlings carrying the nuclear cre gene. In seedlings with no cre sequence the same primers amplified the 2.0-kb coda-containing fragment. Interestingly, cre+seedlings from the cross with Cre2-200 contained a mixed population of coda containing (2.0-kb) and coda-deleted (0.7-kb) fragments indicating less efficient CRE-induced deletion of >codA>. Thus, expression level and tissue specificity of the two nuclear Ssu-tp22-cre genes are characteristic for the individual transformation events. CRE activity of Cre1-100, Cre2-100 and Cre2-300 activator lines is more suitable for rapid elimination of >coda> in a cross than the Cre2-200 line.

It is undesirable to maintain the Ssu-tp-cre activator genes in the production lines. However, these are encoded in the nucleus, and can be separated from the transgenic chloroplasts in the next seed progeny. Linkage of Ssu-tp-cre to the nuclear kanamycin resistance gene facilitates identification of seedlings lacking cre in a segregating seed population.

CRE site-specific recombinase for deletion of plastid DNA sequences. Biolistic transformation of tobacco leaves always yields shoots containing a mixed population of plastid genome copies. A mixed population of plastid genome copies is determined by DNA gel blot analysis (Carrer et al. 1993; Svab and Maliga 1993; Carrer and Maliga 1995) and can be visualized in UV light when expressing the green fluorescence protein in plastids (Khan and Maliga 1999). Homoplastomic, genetically stable plants are obtained during a second cycle of plant regeneration from the leaves of the regenerated plants or in the seed progeny. The cells of the >coda> tester strains carry a uniform population of plastid genome copies. Thus, the Ssu-tp-cre is introduced into the nuclear genome of a cell that is homoplastomic for >codA>. It was expected that the regenerated shoots would contain a mixed population of plastid genome copies. Instead, all plastid genome copies lack >codA>, an evidence for the enormous selection pressure by CRE activity against plastid genome copies that carry two lox sites. It is important that deletion of >coda> occurs in the absence of selection against >coda> by exposure to 5-fluorocytosine. Virtually complete elimination of >coda> may also be obtained when CRE activity is introduced by crossing, using pollen of an appropriate deletion activator strain. Deletion of the selectable marker in somatic cells is the preferred choice over elimination of the marker in the seed progeny. The most important advantage is time saving. Introduction of Ssu-tp-cre into the nucleus of somatic cells requires only three to six weeks; Ssu-tp-cre segregates out in the first seed progeny. In contrast, introduction and elimination of Ssu-tp-cre takes one additional seed progeny, about three months.

Interestingly, genome copies with one lox site or no lox site (wild-type) are stable in CRE-expressing cells. Instability of genomes with two lox sites may be due to formation of linear ends during the excision process. The linear ends may then re-circularize by homologous recombination via the Prrn promoter sequences yielding the trnV-aadA-codA deletion derivatives.

CRE engineering. Although CRE is a prokaryotic protein, it naturally carries a nuclear localization signal (NLS) that targeted a CRE-GFP fusion protein to the nucleus in mammalian cells. The NLS sequences overlap the DNA binding regions and the integrity of this region is important for DNA recombinase activity (Le et al. 1999). We targeted the newly-synthesized TP-CRE protein to plastids using a plastid-targeting transit peptide (TP). The TP is localized at the N terminus of plastid proteins and is cleaved off during import from the cytoplasm into plastids (Soll and Tien, 1998).

Therefore, we translationally fused a plastid transit peptide with CRE to direct its import from the cytoplasm to plastids. Translational fusion yielded a protein with an N-terminal plastid targeting signal and an internal nuclear localization signal. Efficient CRE-mediated deletion of plastid-encoded coda genes indicates targeting of SSU-TP-CRE to plastids. When two potential targeting sequences are present, in general one of them out-competes the other (Small et al. 1998). N-terminal organelle targeting sequences normally dominate the second internal localization signal. For example, the 70-kDa heat shock protein of watermelon cotyledons that carry N-terminal plastidal and internal glyoxysomal targeting sequences are exclusively targeted to plastids. Proteins are localized to glyoxysomes only in the absence of the plastidal presequence (Wimmer et al. 1997). The tRNA modification enzymes contain information for both mitochondrial (N-terminal extension) and nuclear targeting. The enzyme with the N-terminal extension is targeted to mitochondria and only the short form lacking the N-terminal extension is targeted to the nucleus (Small et al. 1998). It was fortunate, that the Rubisco SSU N-terminal transit peptide dominated the CRE nuclear localization signals and the TP-CRE fusion protein was directed to plastids (chloroplasts).

A second property that is important for the present invention is maintenance of recombinase activity when CRE is fused with proteins or peptides at its N and C termini. N-terminal fusion of CRE with the *E. coli* maltose binding protein did not interfere with recombinase function (Kolb and Siddell 1996). CRE was also shown to accept a C-terminal fusion with GFP (Le et al. 1999) as well as an 11-amino-acid epitope to the herpes simplex virus (HSV) glycorpotein D coat protein. The epitope tag facilitates detection of CRE expression in vitro and in vivo using immunofluorescent labeling with a commercially available antibody (Stricklett et al. 1998). Apparently, the five and 22 amino acids that are left behind after processing of the SSU-TP5-CRE and SU-TP22-CRE proteins did not interfere with CRE function.

Dominant negative selection markers for positive identification of deletion derivatives. A practical application of the present invention is the removal of selectable marker genes from the transformed plastid genome. In tobacco, the excision process mediated by the CRE constructs described herein is so efficient that the >coda> deletion derivatives can be identified in the absence of 5FC selection. However, in other crops CRE-mediated excision of marker genes may be less efficient. In these species, the positive selective marker (aadA) may be fused with a dominant negative selective marker using linker peptides as described in the literature (Khan and Maliga 1999) or the positive and negative marker genes may be combined in a dicistronic operon (Staub and Maliga 1995). Dominant negative selection markers allow normally non-toxic compounds to be used as toxic agents, so that cells which express these markers are non-viable in the presence of the compound, while cells that don't carry them are unaffected. For example, cytosine deaminase is absent in plants. Expression of cod, encoding cytosine deaminase (CD; EC 3.5.4.1), in plastids renders tissue culture cells and seedlings sensitive to 5FC, facilitating direct identification of clones lacking this negative selective marker (Serino and Maliga 1997). Cytosine deaminase converts 5-fluorocytosine (5FC) into 5-fluorouracil (5FU), the precursor of 5-fluoro-dUMP. 5FC is lethal for CD-expressing cells due to irreversible inhibition of thymidylate synthase by 5-fluoro-dUMP (Beck et al. 1972). We have found that seedlings and plant tissues expressing >coda> were sensitive to 5FC. Seedlings lacking coda could be readily identified by 5FC resistance. Thus, the constructs described here are suitable to express cytosine deaminase at sufficiently high levels to be useful to implement a negative selection scheme.

Alternative negative selective markers can be obtained by adaptation of substrate-dependent negative selection schemes described for nuclear genes. Such negative selection schemes are based on resistance to indole, napthyl, or naphtalene acetamide (Depicker et al. 1988; Karlin-Neumann et al. 1991; Sundaresan et al. 1995), chlorate (Nussaume et al. 1991), kanamycin (Xiang and Guerra 1993) and 5-fluorocytosine (5FC) (Perera et al. 1993; Stougaard 1993).

EXAMPLE 2

Cre-Mediated Inversion of Plasmid DNA Sequences

Figure 9:
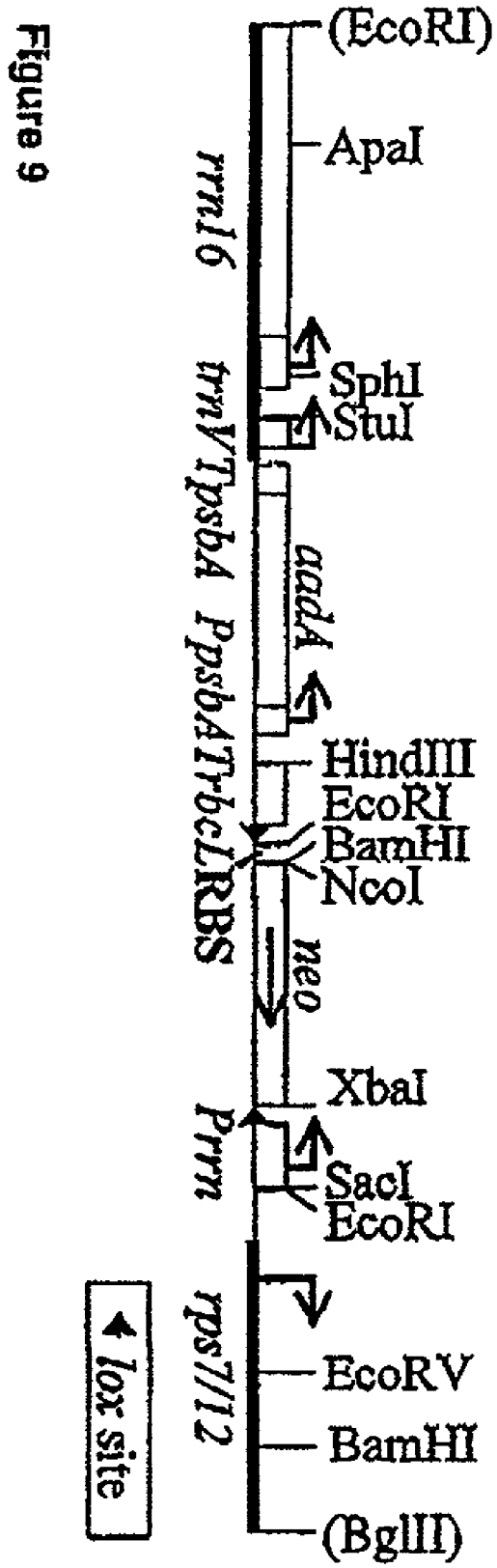
FIG. 9 is a diagram of the plastid transformation pSAC38 with the >neo< bracketed by inverted lox sites. Positions of plastid genes rrn16, trnV and rps12/7 (Shinozaki et al., 1986), the aada and coda transgenes and relevant restriction sites are marked.

If the lox sites in bacteria are in an inverted orientation, CRE-mediated recombination results in an inversion of the intervening DNA. We have tested, whether the CRE-mediated inversion reaction also occurs in plastids of higher plants containing DNA sequences flanked by inverted lox sites. This was assessed using a kanamycin-resistance (>neo<) coding region in an inverted orientation relative to the promoter (FIG. 9). In this construct the non-coding strand of neo is transcribed and the plants are kanamycin sensitive. The >neo< coding region is flanked by inverted lox sites. CRE-mediated inversion of the sequences reverses neo orientation resulting in the transcription of the sense strand and expression of kanamycin resistance. Inversion of the plastid-encoded >neo< coding region may be achieved by multiple approaches. One approach is to introduce a nuclear Cre into the nucleus of somatic tobacco cells, e.g., leaf, by *Agrobacterium*-mediated transformation. A second approach is introduction of the nuclear-encoded Cre gene by fertilization with pollen of an appropriate activator-of-inversion strain. Additional approaches are to provide CRE-activity via the incorporation of chemically inducible promoter into the construct, or to transiently express CRE from a nuclear of chloroplast construct.

Materials and Methods for the Practice of Example 2

Figure 8:
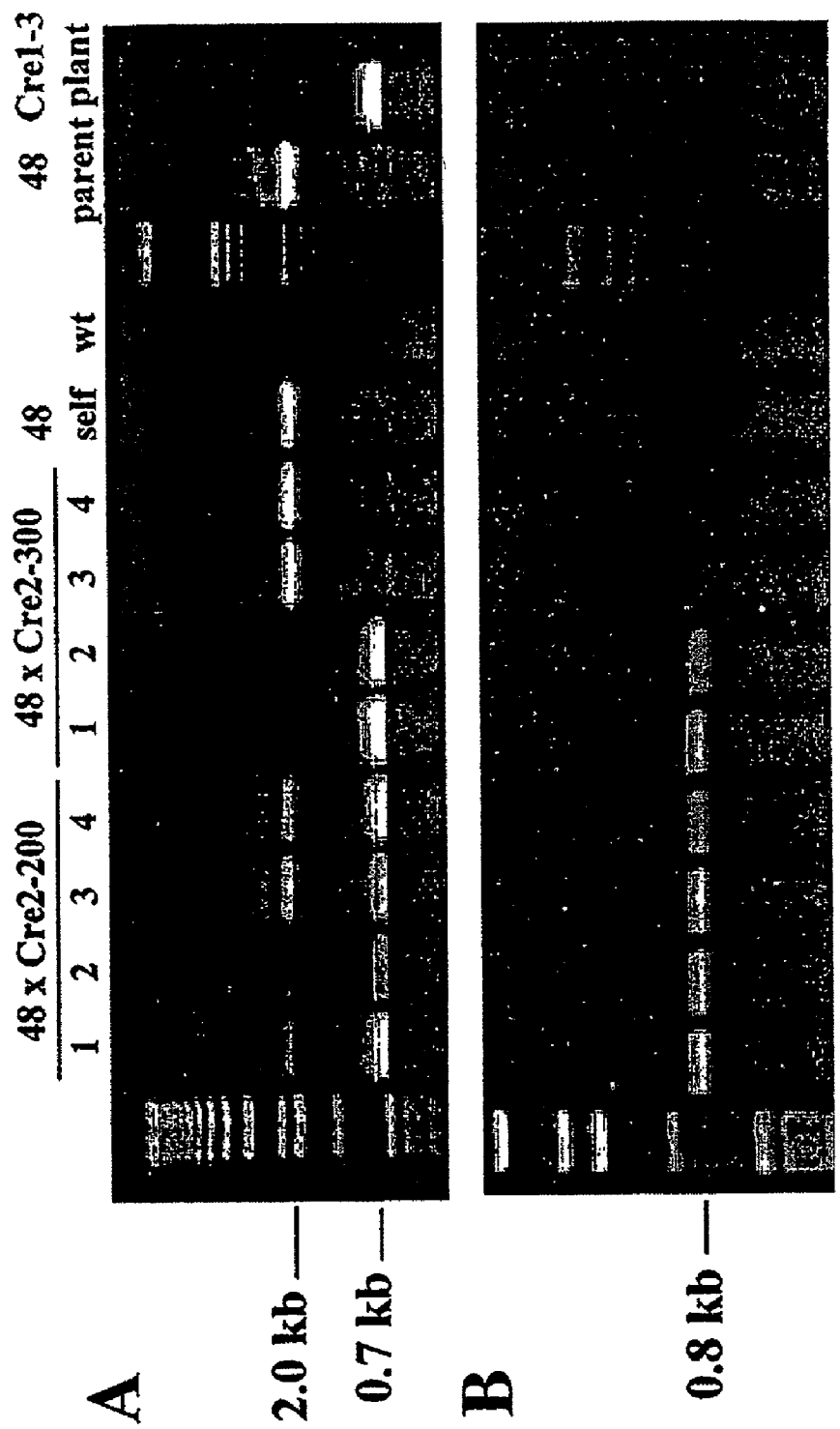
FIGS. 8A and 8B are gels of PCR analysis confirming CRE-mediated deletion of coda in seedlings obtained by pollination with Ssu-tp-cre activator lines. 5-day old seedlings were tested from the cross Nt-pSAC48-21A as maternal parent and Cre2-200 and Cre2-300 activator lines as pollen parents. Amplification products are also shown for controls Nt-pSAC48-21A selfed seedling (48 self), wild-type (wt), the parental plant (48P) and the Cre1-3 plant.

Plastid neo gene with inverted lox sites. The neo gene is contained in a SacI-HindHIII fragment. The gene map is shown in FIG. 8. PrrnloxI (SEQ ID NO: 1) is a plastid rRNA operon (rrn16) promoter derivative. It is contained in a SacI-XbaI fragment obtained by PCR using oligonucleotides 5'-ggggagctcGCTCCCCCGCCGTCGTTCAATG-3' (SEQ ID NO: 14) and 5'-ggtctagataacttcgtatagcatacattat acgaagttatGCTCCCAGAAATATAGCCA-3' (SEQ ID NO: 28) as primers and plasmid pZS176 (progenitor of plasmid pZS197; Svab and Maliga 1993) as a template. The promoter fragment PrrnloxI contains a lox site at the 3' end adjacent to the XbaI site.

Figure 28:
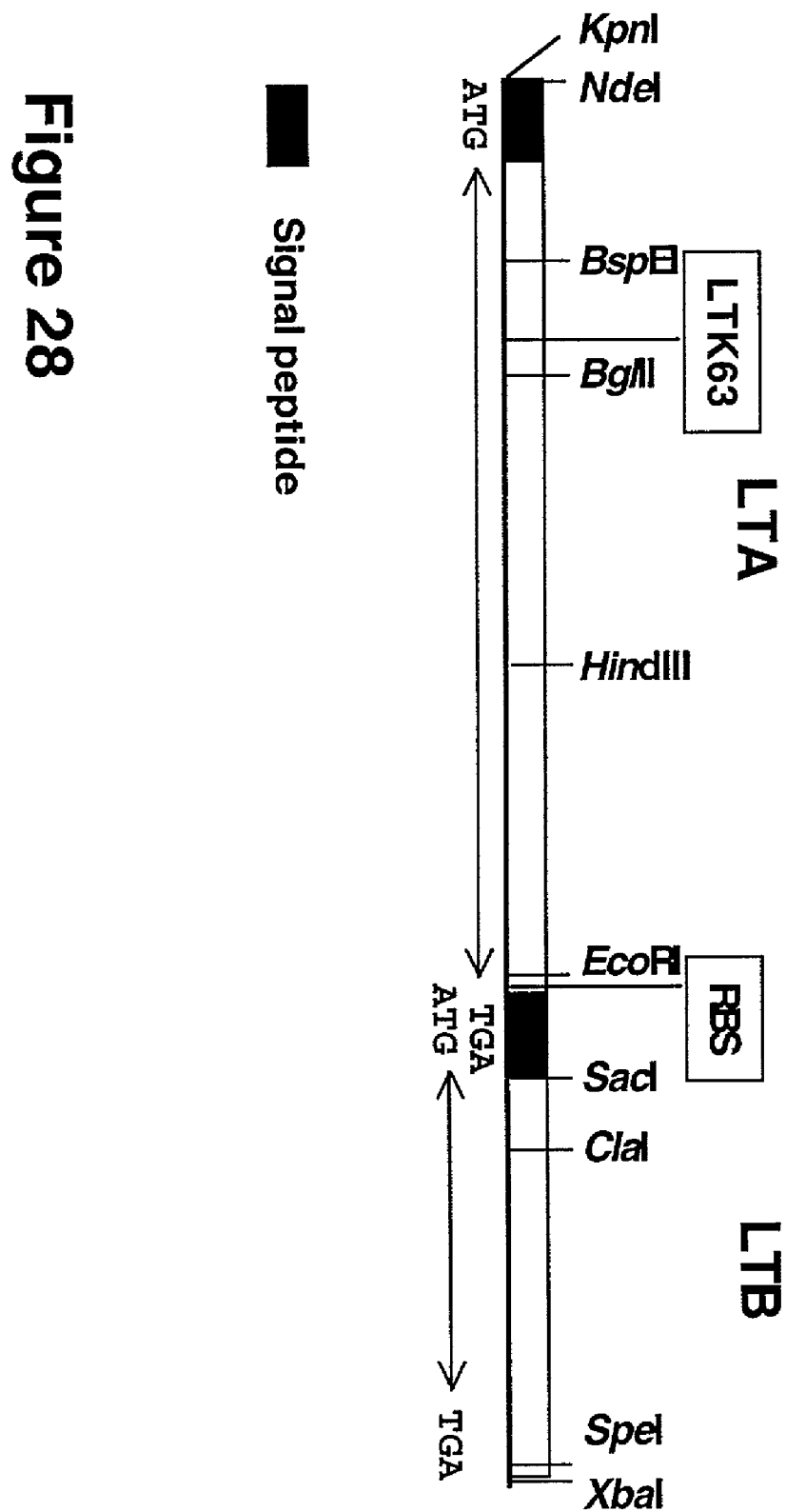
FIG. 28. Map of the engineered LTK63 bacterial operon with unique restriction sites for expression in chloroplast vectors and for engineering.
Figure 29:
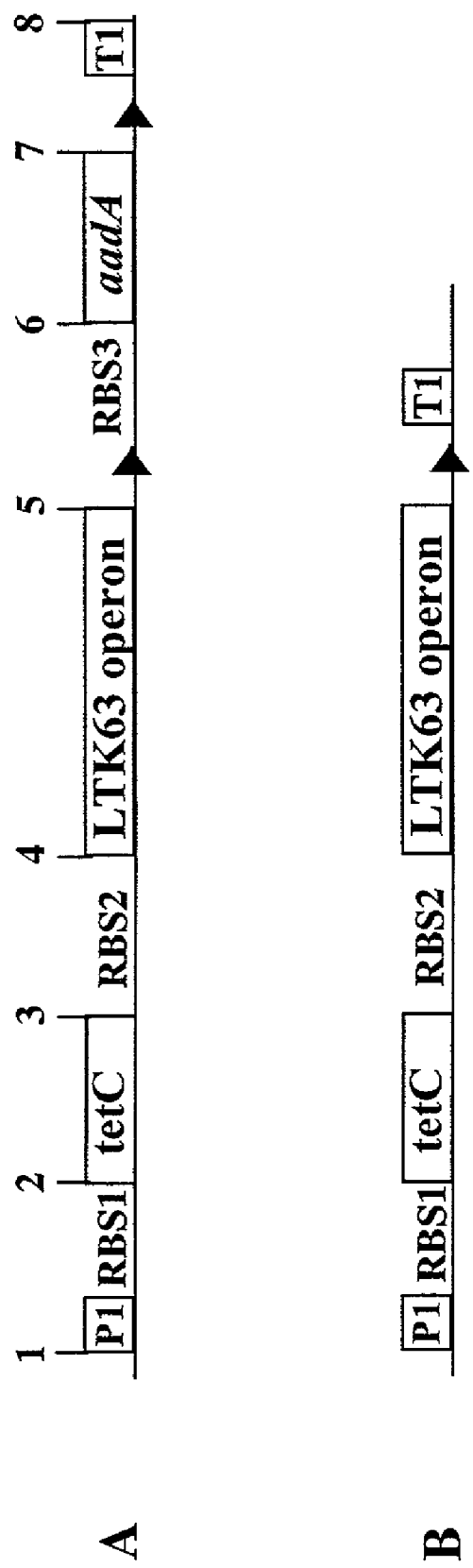
FIG. 29. (A) TetC-LTK63 operon with excisable selective marker (aadA). The numbers define the boundaries of functional units. (B) The TetC-LTK63 operon in the plastid genome after CRE-mediated excision of aadA.

The neo coding region is contained in an NcoI-XbaI fragment derived from plasmid pHC62. The neo sequence in plasmid pHC62 is identical with the neo sequence shown in FIG. 28B, U.S. Pat. No. 5,877,402. The EcoRI-NcoI fragment contains the ribosome binding site from plasmid pZS176. The fragment was obtained by annealing the complementary oligonucleotides 5'-AATTCGAAGCGCT-TGGATACA GTTGTAGGGAGGGATC-3' (SEQ ID NO: 16) and 5'-CATGGATCCCTC CCTACAACTGTATC-CAAGCGCTTCG-3' (SEQ ID NO: 17). The TrbcLloxI (SEQ ID NO: 2) is the rbcL 31-untranslated region contained in an EcoRI-HindIII fragment obtained by PCR using oligonucleotides 5'-gggaattcataacttcgt atagcatacattatac-gaagttatAGACATTAGCAGATAAATT-3' (SEQ ID NO: 29) and 5'-gggggtaccaagcttgCTAGATTTTGTATTTCAAA TCTTG-3' (SEQ ID NO: 19)and plasmid pMSK48 (Khan and Maliga 1999) as template. TrbcLloxI contains a lox site adjacent to the EcoRI site in an inverted orientation relative to the lox site in PrrnloxI. The chimeric PrrnloxI:neo: TrbcLloxI gene was introduced into the tobacco plastid transformation vector pPRV111B (Zoubenko et al. 1994) as a SacI-HindIII fragment to obtain plasmid pSAC38.

Plastid-targeted nuclear cre linked to a nuclear gentamycin resistance (aacC1) gene. The plastid targeted nuclear cre genes were introduced as EcoRI-HindIII fragments into the pPZP222 *Agrobacterium* binary vectors which carry a plant-selectable gentamycin resistance gene (Hajdukiewicz et al. 1994) to obtain plasmids pKO30 and pKO31 with twenty two and five amino acids of the mature Rubisco SSU. The map of the *Agrobacterium* vectors is identical with the one shown in FIG. 3. other than they carry a gentamycin resistance gene.

Transplastomic Tobacco Plants with a Neo Gene Flanked by Inverted lox Sites.

Plastid transformation vector pSAC38 with the inverted >neo< gene is shown in FIG. 9. The inverted >neo< gene was introduced into plastids by selection for spectinomcyin resistance (aadA) encoded in the vector. Two independently transformed lines were purified to the homoplastomic state: Nt-pSAC38-9A and Nt-pSAC38-10C. The homoplastomic state was confirmed by DNA gel blot analysis.

Nuclear-encoded Plastid-targeted Cre Genes.

Plant activator lines in which Ssu-tp-cre is linked to a nuclear kanamycin resistance gene have been described in Example 1. The plastid marker to test CRE-activated inversion described in Example 2 utilizes a kanamycin resistance gene. Kanamycin resistance conferred by the plastid gene due to CRE-mediated inversion could not be distinguished from kanamycin resistance conferred by the marker gene of the *Agrobacterium* binary vector that was used to introduce the nuclear cre. Therefore, we have constructed activator strains in which Ssu-tp-cre is linked to gentamycin resistance. The Ssu-tp22-cre gene linked to the nuclear gentamycin resistance is the Cre3 strain and the Ssu-tp5-cre gene linked to gentamycin resistance is the Cre4 strain.

Inversion of >neo< in the Plastid Genome of Somatic Cells.

Figure 10:
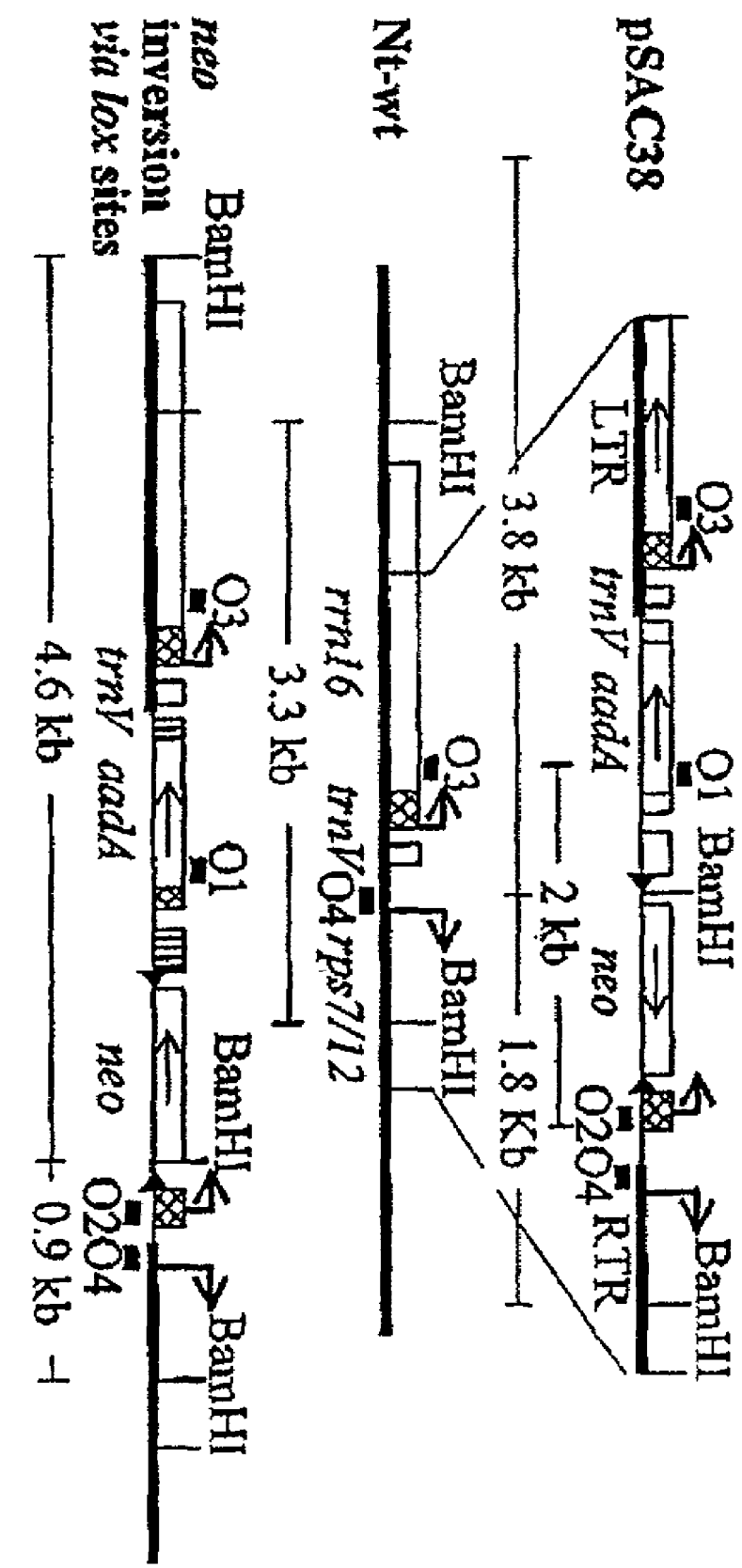
FIG. 10 shows a map of the plastid genome containing the >neo< inversion construct. Shown are the plastid targeting region of vector pSAC38; the map of the same region of the wild-type plastid genome (Nt-wt); map of the plastid genome with CRE-mediated inversion of neo via the lox sites. Positions of the plastid genes rrn16, trnV and rps12/7 (Shinozaki et al., 1986) aadA and neo transgenes, primers (O1–O4) and relevant restriction sites (BamHI) are marked.
Figure 11:
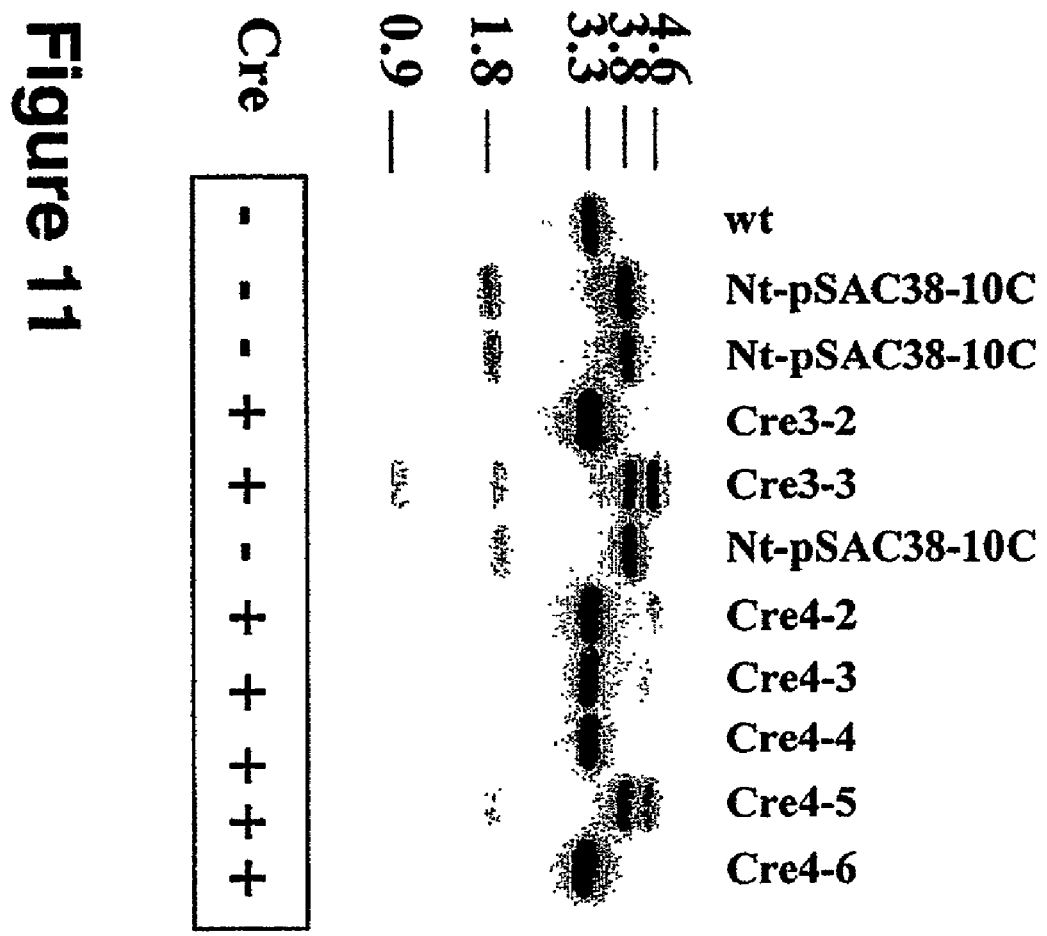
FIG. 11 shows the results of DNA gel blot analysis for the determination of plastid genome structure of CRE-activated >neo< plants by DNA gel blot analysis. Total cellular DNA was digested with the BamHI restriction endonuclease. The probes was the wild-type ApaI-EcoRV plastid targeting region. The hybridizing fragments are marked in FIG. 10.

The nuclear are genes were introduced into the chloroplast >neo< tester strains by cocultivation of tobacco leaves with the *Agrobacterium* strains and selection for gentamycin resistance (100 mg/L). Digestion of total cellular DNA with BamHI and probing with the plastid targeting region (ApaI-EcoRV fragment, FIG. 4) hybridizes to 1.8-kb and a 3.8-kb fragments in the parental Nt-pSAC38-10C lines (FIG. 10). Activation by CRE in lines Cre3-3 and Cre4-5 created a mixed population of >neo< genes representing the original and inverted orientations detected as the original 3.8-kb and 1.8-kb and the newly created 4.6-kb and 0.9-kb hybridizing fragments. Lines carrying the are and an approximately wild-type size fragment are aadA-neo deletion derivatives, similar to those shown in FIG. 4. Thus, it appears that CRE mediated inversion via lox sites creates increased local recombination frequencies that leads to deletion of the transgenes via the short direct repeats of Prrn promoters.

Controlling Inversion Via lox Sites by CRE Activity.

Here we describe constructs for CRE-mediated inversion of plastid genome segments flanked by inverted lox sites. Inversion of the sequences is independent of the encoded genetic information and relies only on CRE activity. CRE activity may be provided transiently, by expression in plastids from plastid signals described in U.S. Pat. No. 5,877, 402, or from nuclear genes encoding a plastid-targeted CRE. Such plastid-targeted CRE constructs are described in Example 1, for example the Ssu-tp5-cre or Sssu-tp22-cre genes. Alternative approaches to provide CRE activity are stable incorporation of a plastid-targeted nuclear Cre into the nucleus of somatic (leaf) cells by *Agrobacterium*-mediated, PEG induced or biolistic transformation or by fertilization with pollen from a transformed plant. The *Agrobacterium* P2 promoter and cauliflower mosaic virus 35S promoter exemplified here are constitutive promoters. Regulated expression of CRE may be important for certain applications. Developmentally timed expression may be obtained from promoters with tissue specific activity. Regulated expression of CRE may be obtained from chemically induced nuclear gene promoters responding to elicitors, steroids, copper or tetracycline (reviewed in; Gatz et al. 1992; Mett et al. 1993; Aoyama and Chau 1997; Gatz 1997; Martinez et al. 1999; Love et al. 2000) and described in U.S. pat. 5,614,395.

Controlled Expression of Deleterious Gene Products

There are a variety of valuable heterologous proteins that interfere with plastid metabolism. For example, certain proteins may be inserted into photosynthetic membranes and interfere with photosynthesis. This problem can be circumvented by first growing the plants to maturity, then activating production of the deleterious protein by chemically inducing CRE expression. CRE, in turn, will make the gene expressible by lox-mediated inversion of the coding region.

Figure 12:
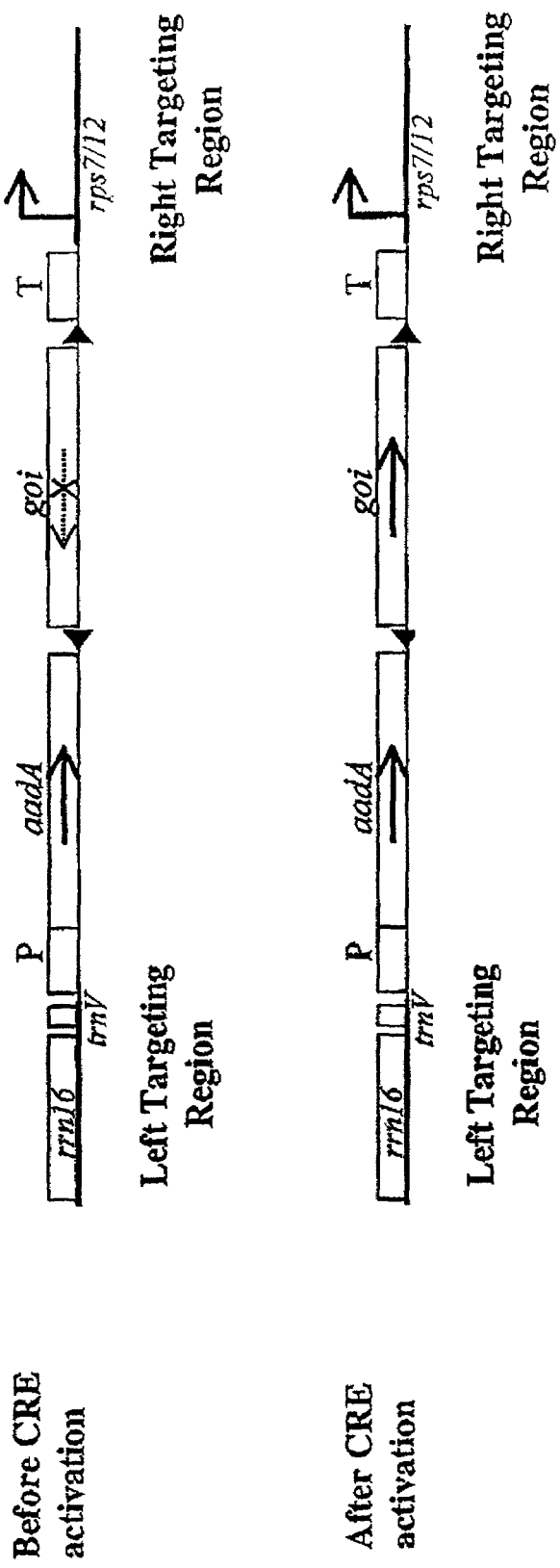
FIG. 12 shows an exemplary monocistronic inversion vector. The gene of interest (goi) coding region is flanked by inverted lox sites (triangles). CRE activates goi expression by inversion, so that the coding strand is transcribed. rrn16, trnV and rps12/7 are plastid genes (Shinozaki et al. 1986).

The molecular tools necessary for the construction of such plastid genes are described in present application. In case of the monocistronic inversion vector the gene of interest (goi)

is flanked by inverted lox sites and is introduced by linkage with aadA (FIG. 12). The selectable marker (aadA) coding region is the first reading frame, and is expressed from the promoter. The goi reading frame is the second coding region, and it is not expressed as it is in an inverted orientation relative to the promoter. Expression of goi is induced by CRE-mediated inversion of the goi coding region, as described for >neo< in Example 2 and is shown in FIG. 12.

Figure 13:
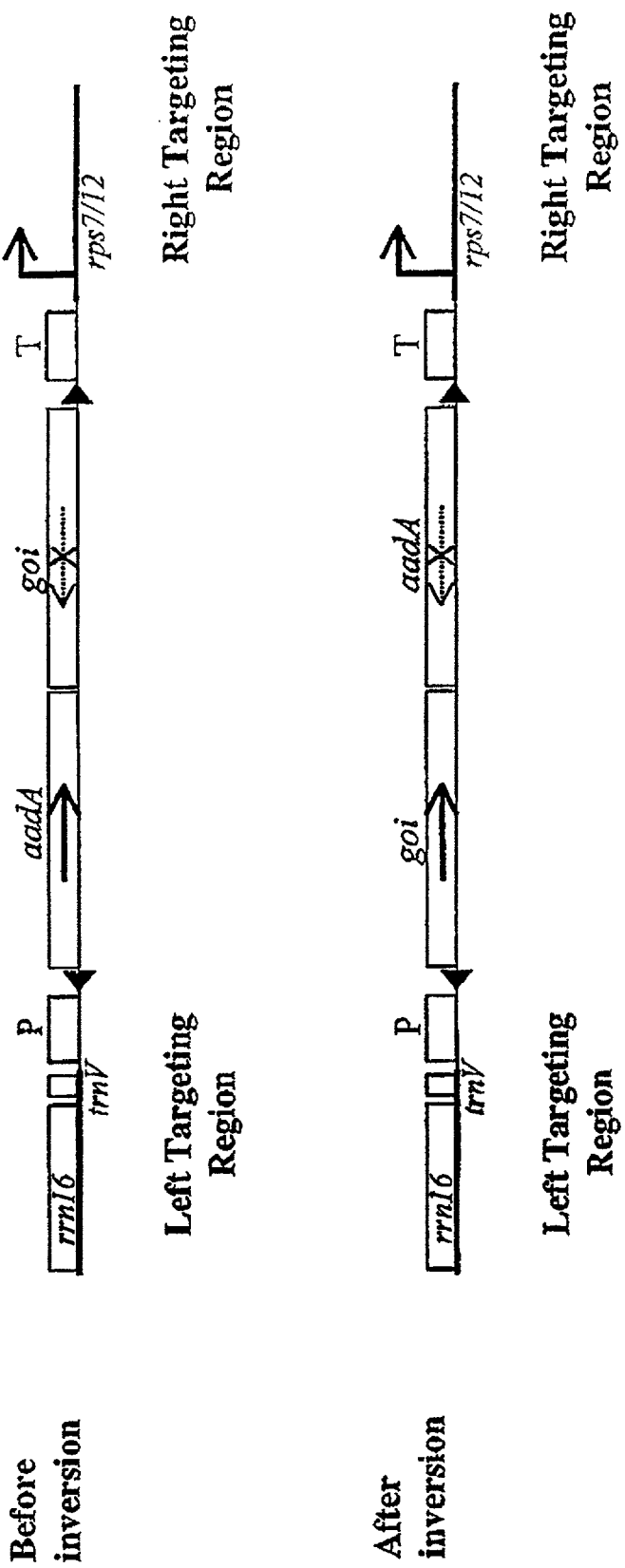
FIG. 13 shows an alternative dicistronic lox inversion vector. Note that the inverted lox sites flank the selective marker (aadA) and goi, and only one gene is expressed. rrn16, trnv and rps12/7 are plastid genes (Shinozaki et al. 1986).

The dicistronic lox inversion vector is shown in FIG. 13. In this case the inverted lox sites flank both aadA and goi. The selectable marker (aadA) coding region is expressed from the promoter. The goi reading frame is not expressed as it is in an inverted orientation relative to the promoter. Expression of goi is induced by CRE-mediated inversion of the aadA-goi containing region that results in simultaneous expression of goi and inactivation of aadA.

The presence of two lox sites may destabilize the plastid genome that leads to CRE-independent deletion of plastid genome sequences. However, it appears that CRE activity by itself is not mutagenic, and the plastid genomes are stable if only one lox site is present. Mutant lox sites that are efficiently excised but recombine into excision resistant sites have been described (Hoess et al. 1982; Albert et al. 1995). Such lox sites would mediate efficient inversion, but the new lox sites would be resistant to additional cycles of CRE activation. Providing only a short burst of CRE activation using a chemically induced promoter could further refine the expression system.

EXAMPLE 3

Cre-Mediated Deletion to Obtain Marker Free Transplastomic Plants and for High Level Expression of the Recombinant Proteins Plastid loxP vectors in this section are described for CRE-mediated excision of selective markers in transplastomic plants. Since excision of sequences between directly oriented lox sites is very efficient, variants of the same vectors can be used for CRE-activated expression of recombinant proteins. A family of plastid vectors with suitably positioned lox sites is shown schematically in FIG. 14 through FIG. 17.

Figure 14:
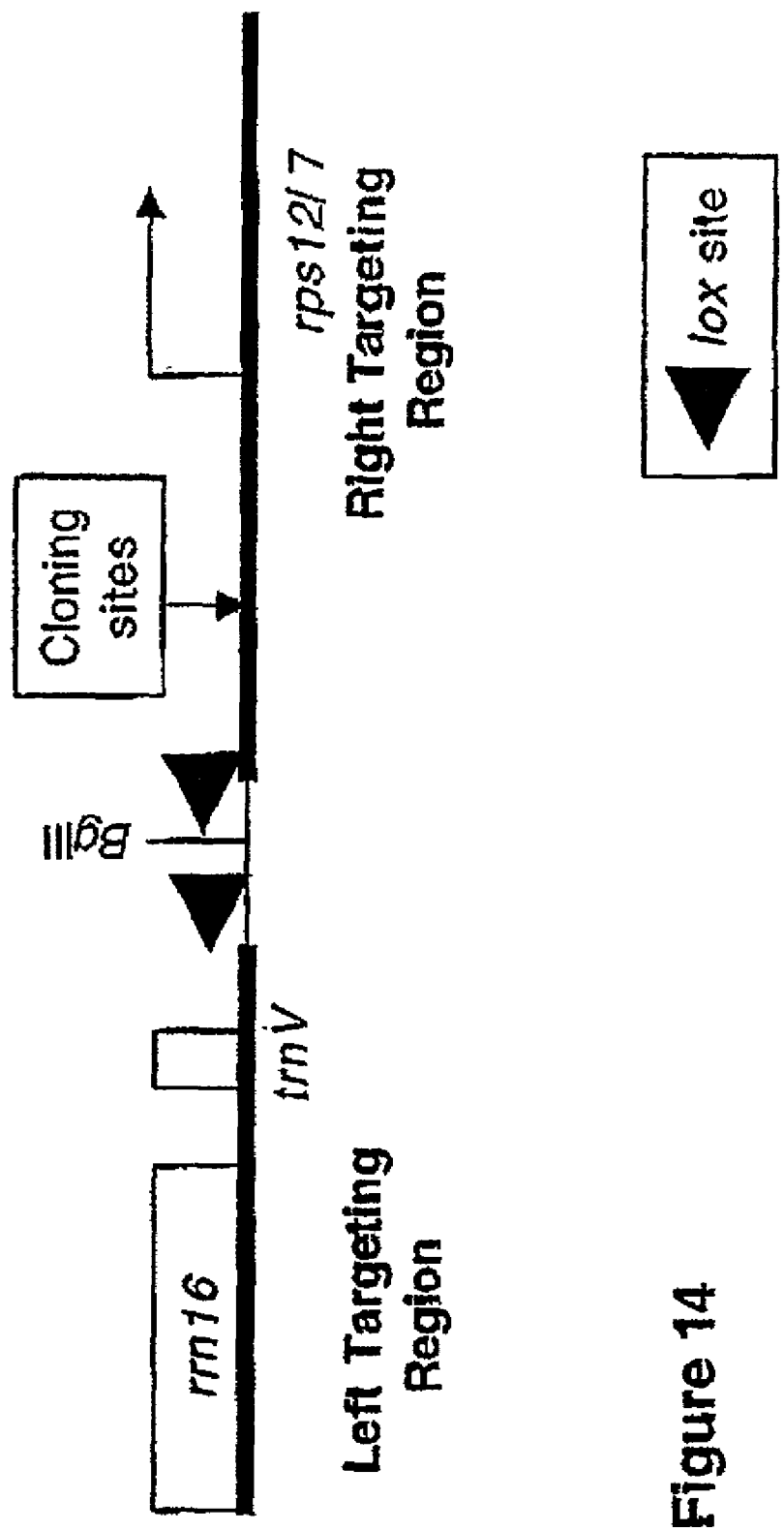
FIG. 14 shows a basic tobacco plastid lox deletion vector. The vector provides is a suitable backbone for vector construction and targets insertions into the trnV-rps12/7 intergenic region.

The map of the basic tobacco plastid lox deletion vector is shown in FIG. 14. It contains (a) two directly oriented lox sites separated by a unique BglII cloning site and (b) an adjacent polycloning site. These sequences (Seg. ID No. 11) are inserted into the ScaI site plastid repeat vector pPRV100 (U.S. Pat. No. 5,877,402; Zoubenko et al. 1994). Suitable marker genes (aadA, neo or kan, bar, glyphosate resistance, bromoxynil resistance) for insertion into the BglII site have been described in U.S. Pat. No. 5,877,402, WO 00/07421 and WO 00/03022.

Figure 15:
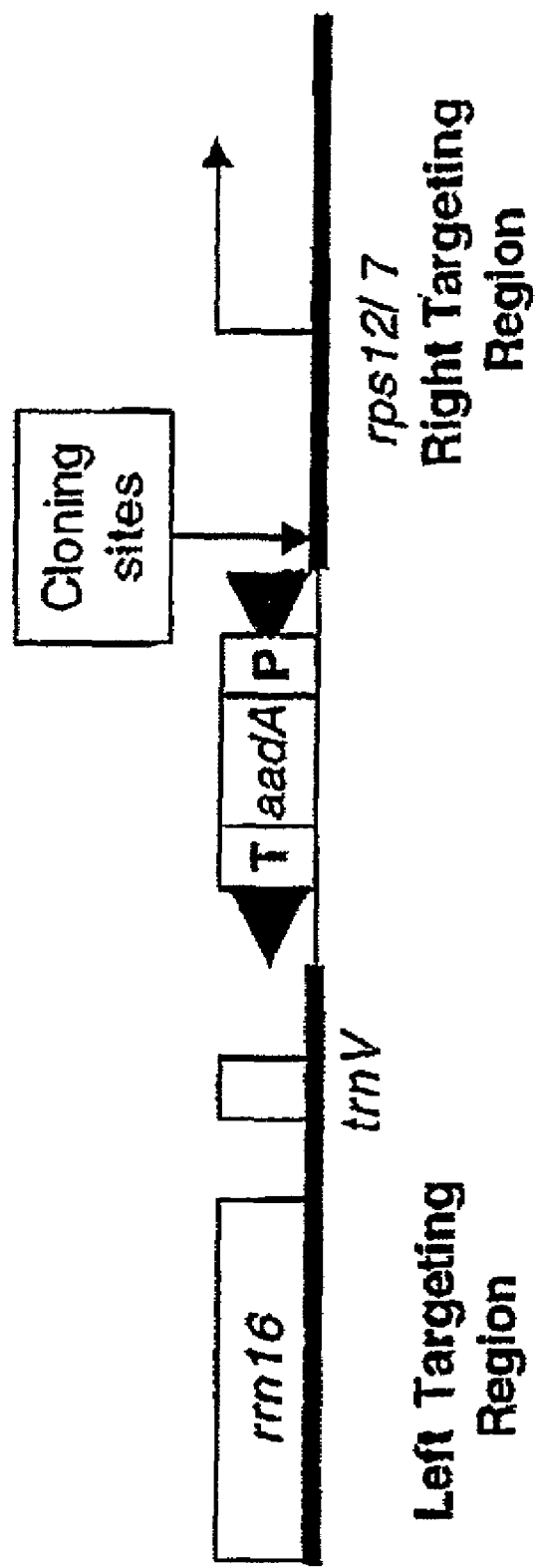
FIG. 15 shows a tobacco plastid lox >aadA> deletion vector. rrn16, trnv and rps12/7 are plastid genes (Shinozaki et al. 1986).

The map of the tobacco plastid lox >aadA> deletion vector is shown in FIG. 15. It is the basic lox deletion vector with an aadA gene cloned into the BglII sites oriented towards the rrn operon.

Figure 16:
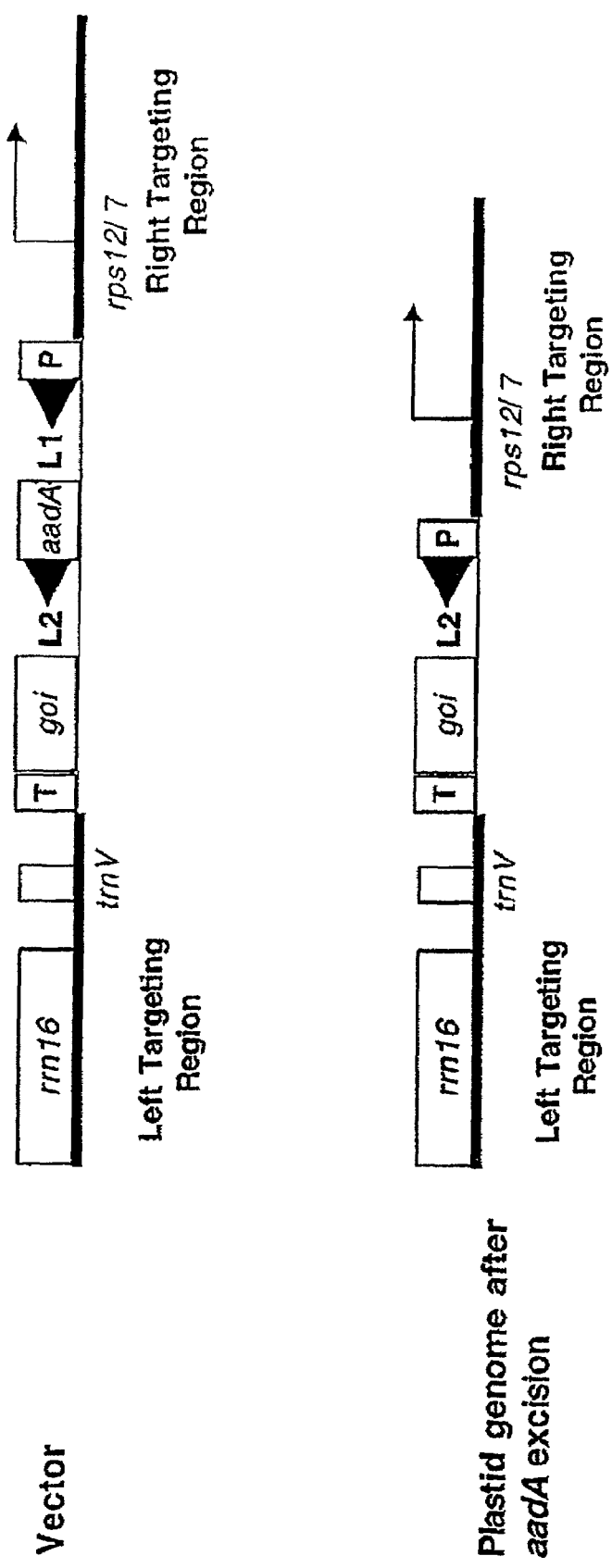
FIG. 16 shows a tobacco constitutive >aadA> dicistronic deletion vector. rrn16, trnV and rps12/7 are plastid genes and are described in (Shinozaki et al. 1986).
Figure 17:
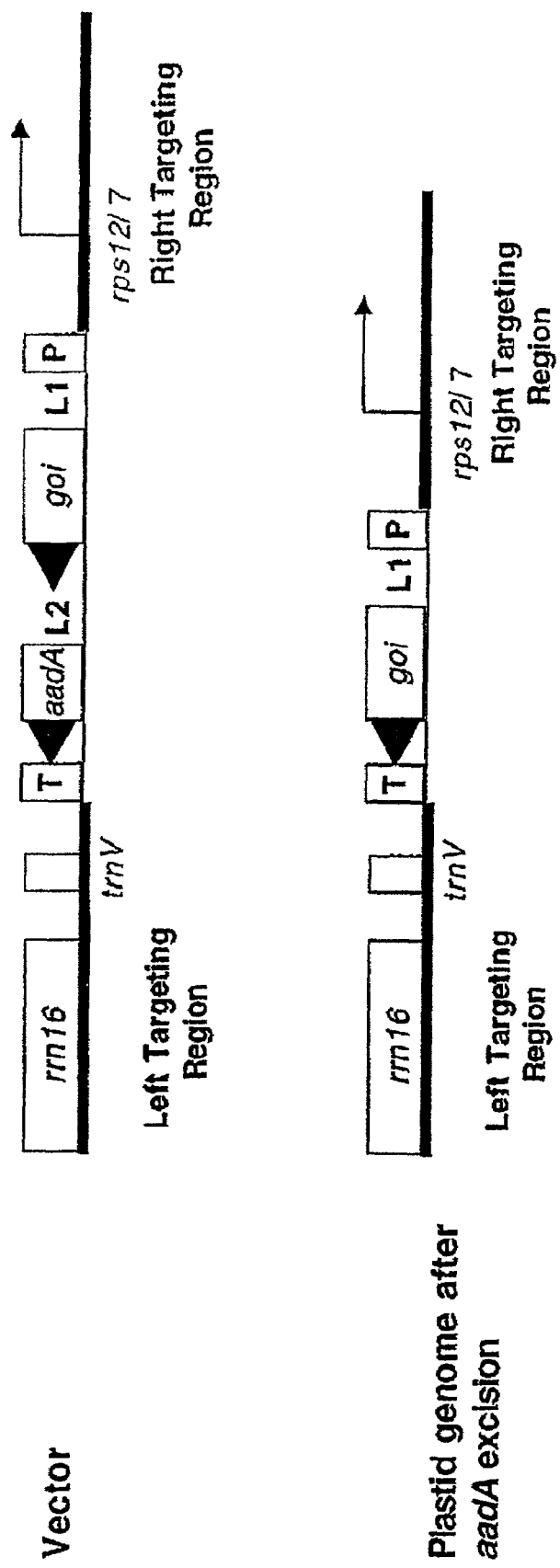
FIG. 17 shows a tobacco constitutive goi >aadA> dicistronic deletion vector. Note that vectors shown in FIG. 16 and FIG. 17 differ in the relative order of marker gene and the gene of interest. rrn16, trnV and rps12/7 are plastid genes (Shinozaki et al. 1986).
Figure 18:
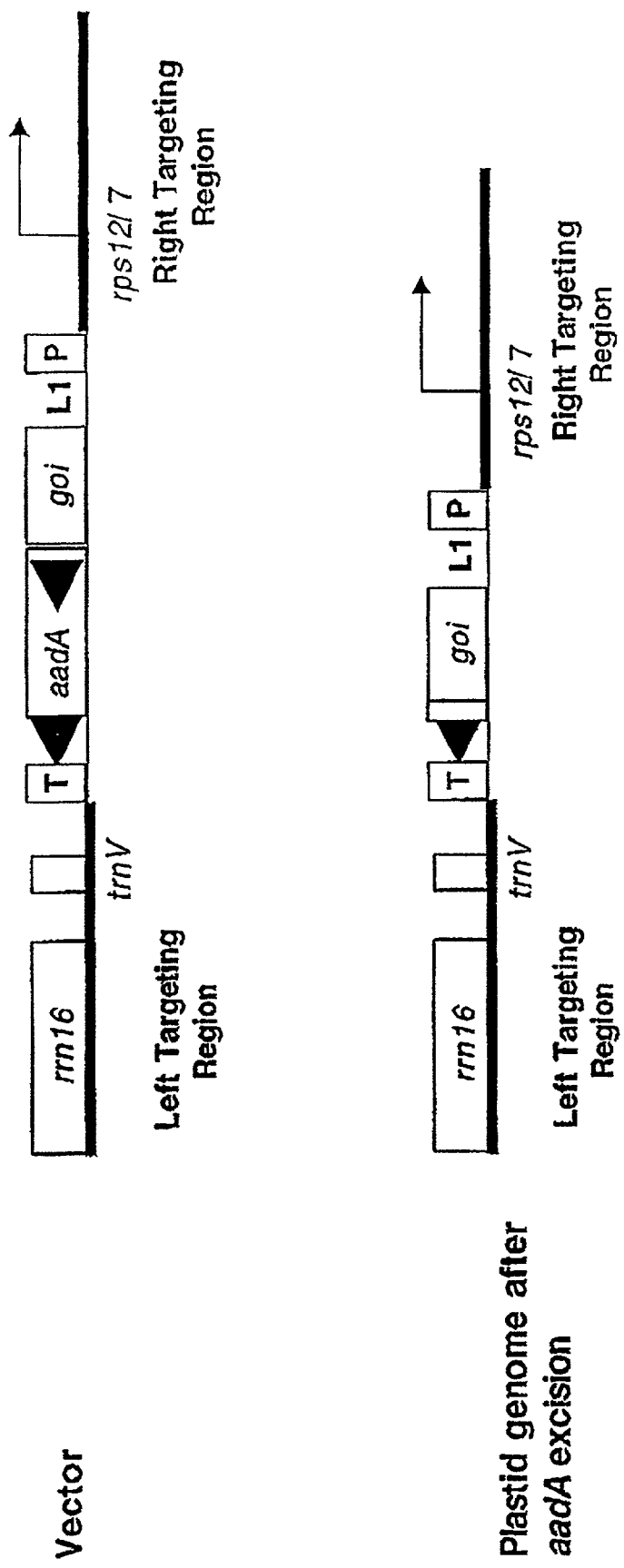
FIG. 18 shows a tobacco constitutive goi >aadA> dicistronic deletion vector, in which expression of aadA is dependent on translational coupling. Note that in this construct only one leader sequence is utilized. rrn16, trnV and rps12/7 are plastid genes (Shinozaki et al. 1986).

Maps of constitutive lox dicistronic deletion vectors are shown in FIG. 16 through FIG. 18. This dicistronic design enables simultaneous expression of both the first and the second open reading frames. The selectable marker designed for excision may be encoded in the first (FIG. 16) or second (FIG. 17, FIG. 18) open reading frames. Since a minimally 34 bp lox site is located between the two reading frames, both the marker gene (aadA) and the gene of interest have their own leader sequence to facilitate translation (FIG. 16, FIG. 17). Translational coupling may also be feasible if the lox site is incorporated in the marker gene coding region N terminus (FIG. 18). DNA sequence of promoter-lox constructs shown in FIG. 16 is set forth in Seq. ID No. 1. Promoters and promoter-leader combinations suitable to promote high-level protein expression in plastids are described in European Patent Applications WO 00/07421, WO 97/06250 and WO 98/55595. Sequences suitable for directly oriented lox sites are given in Seq. ID No. 11. Translational coupling between a gene of interest and the downstream aadA is shown in FIG. 18. There are multiple ways of achieving translational coupling between adjacent genes (Baneyx 1999). One approach is incorporation of a properly spaced ribosome binding-site in the upstream gene's coding region (Schoner et al. 1986; Omer et al. 1995). An example for a suitable sequence directly upstream of the translation initiation codon (ATG) would be G-GAG-GAA-TAA-CTT-ATG (SEQ ID NO: 30). A specific example for the use of the sequence is translational coupling between a bar (suitable source described in European Patent Application WO 00/07421) and a downstream aadA are given in Seq. ID No. 12. Note SalI site downstream of AUG incorporated to facilitate engineering the BglII-SalI region and the directly oriented lox sites in the aadA coding region and downstream of aadA. The sequence is given for a BglII-SpeI fragment. The BglII site is within the bar coding region; the SpeI site is downstream of the second lox site, as marked in FIG. 18. If a C-terminal extension to create a ribosome binding site is unacceptable, a suitable sequence may be obtained by silent mutagenesis of the coding region at the third codon position. Variants of plastid ribosome binding sites have been catalogued (Bonham-Smith and Bourque 1989)

Figure 19:
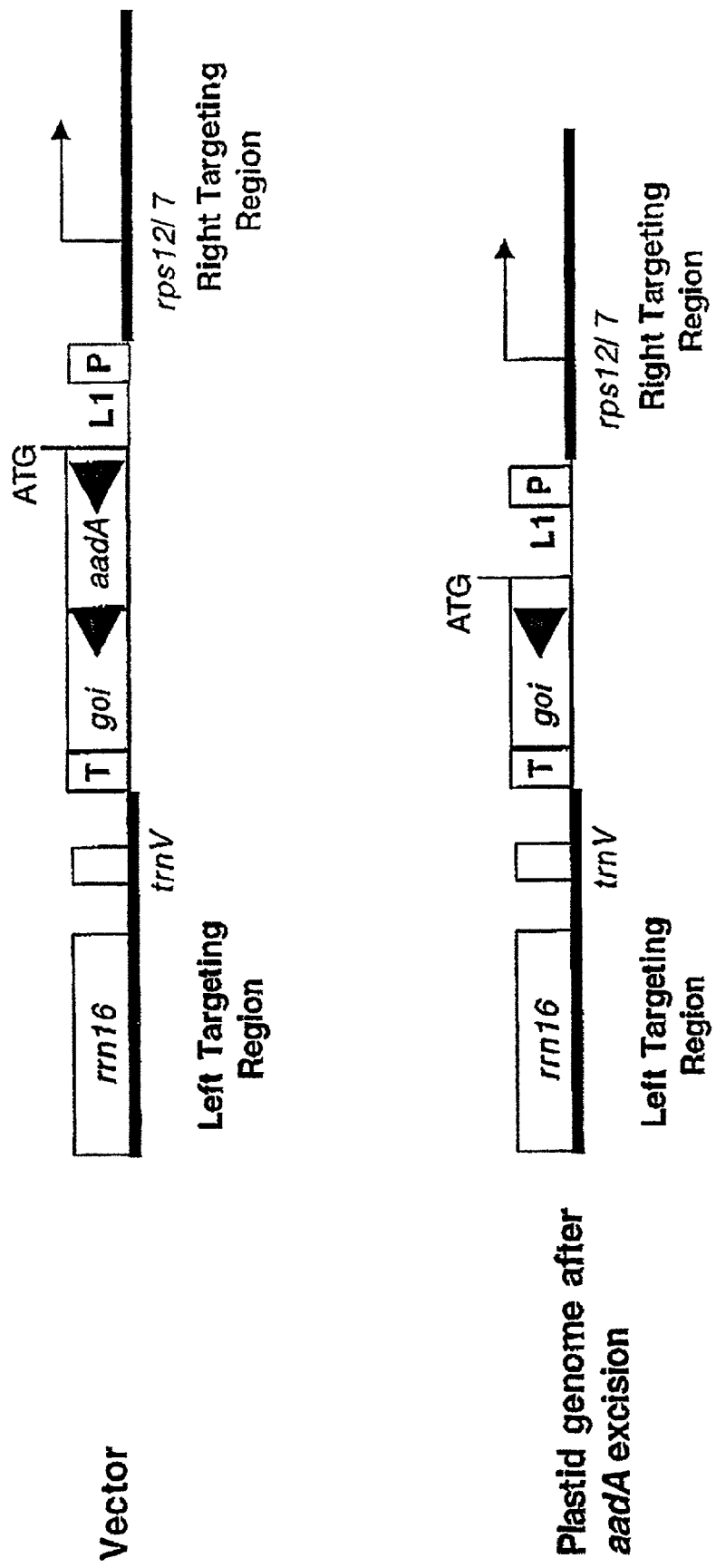
FIG. 19 shows a tobacco inducible lox deletion vector. Expression of goi is dependent on aadA excision. rrn16, trnv and rps12/7 are plastid genes (Shinozaki et al. 1986). Abbreviations: P, promoter; T, 3' untranslated region; L1 is 5' leader sequence.

A tobacco inducible lox deletion vector is shown in FIG. 19. The marker gene (aadA) is encoded in the first reading frame, followed by a silent goi lacking the translation initiation codon (ATG) and the 5' untranslated leader. Expression of the goi frame is triggered by aadA excision that results in translational fusion of the aadA N-terminal region with the goi. After aadA excision the goi mRNA is translated from the aadA translation control signals, the 5' UTR and AUG. DNA sequence of the SacI-NheI fragment is given in Seq. ID. No. 13. The Prrn promoter-atpB translational control region is described in European Patent Application WO 00/07421. The aadA construct has two directly-oriented lox sites: one in the coding region N-terminus and one downstream of aadA to facilitate CRE-mediated excision of the marker gene.

EXAMPLE 4

Deletion of Vital Plastid Genes to Obtain Cytoplasmic Male Sterility

U.S. Pat. No. 5,530,191 provides a cytoplasmic male sterility (CMS) system for plants, which is based on modification of the plastid genome. The CMS system comprises three transgenes: a "plastid male sterility" gene that causes plastid and cellular disablement of the anther tissue, and two nuclear genes that regulate the expression of the plastid gene. An important feature of the system is developmentally timed cellular death based on the expression, or the lack of the expression, of a plastid gene. As one specific approach to induce developmentally timed ablation of anther tissue we describe CRE-mediate excision of essential plastid genes via directly oriented lox sites.

The number of genes encoded by the plastid genome is about 120. Some of the genes are non-essential and may be inactivated by targeted gene disruption without a major phenotypic consequence. Good examples are the plastid ndh genes (Burrows et al. 1998; Shikanai et al. 1998) or the trnV gene the deletion of which has been described in Example 1. Excision of these genes is unlikely to cause cell ablation. The photosynthetic genes are essential for survival under field conditions. However, pigment deficient, non-photosynthetic plants can be maintained as long as they are grown on a sucrose-containing medium, or are grafted onto photosynthetically active wild-type (green) plants (Kanevski and Maliga 1994). Some of the house-keeping genes, such as the genes encoding the plastid multisubunit RNA polymerase are essential for photosynthetic growth, but not for survival (Allison et al. 1996). Thus, deletion of these genes is not suitable to trigger cell death. Only a relatively small number of plastid genes have proven to be essential for viability. The essential nature of the genes was recognized by the lack of homoplastomic cells in gene disruption experiments indicating that the loss of these genes results in cellular death. Cellular death due to lack of plastid function is understandable, as plastids are the site of the biosynthesis of amino acids, several lipids and are required for nitrate assimilation. Examples of plastid genes essential for cellular survival are the clpP protease subunit gene (Huang et al. 1994), ycf1 and ycf2, the two largest plastid-encoded open reading frames (Drescher et al. 2000).

Figure 20:
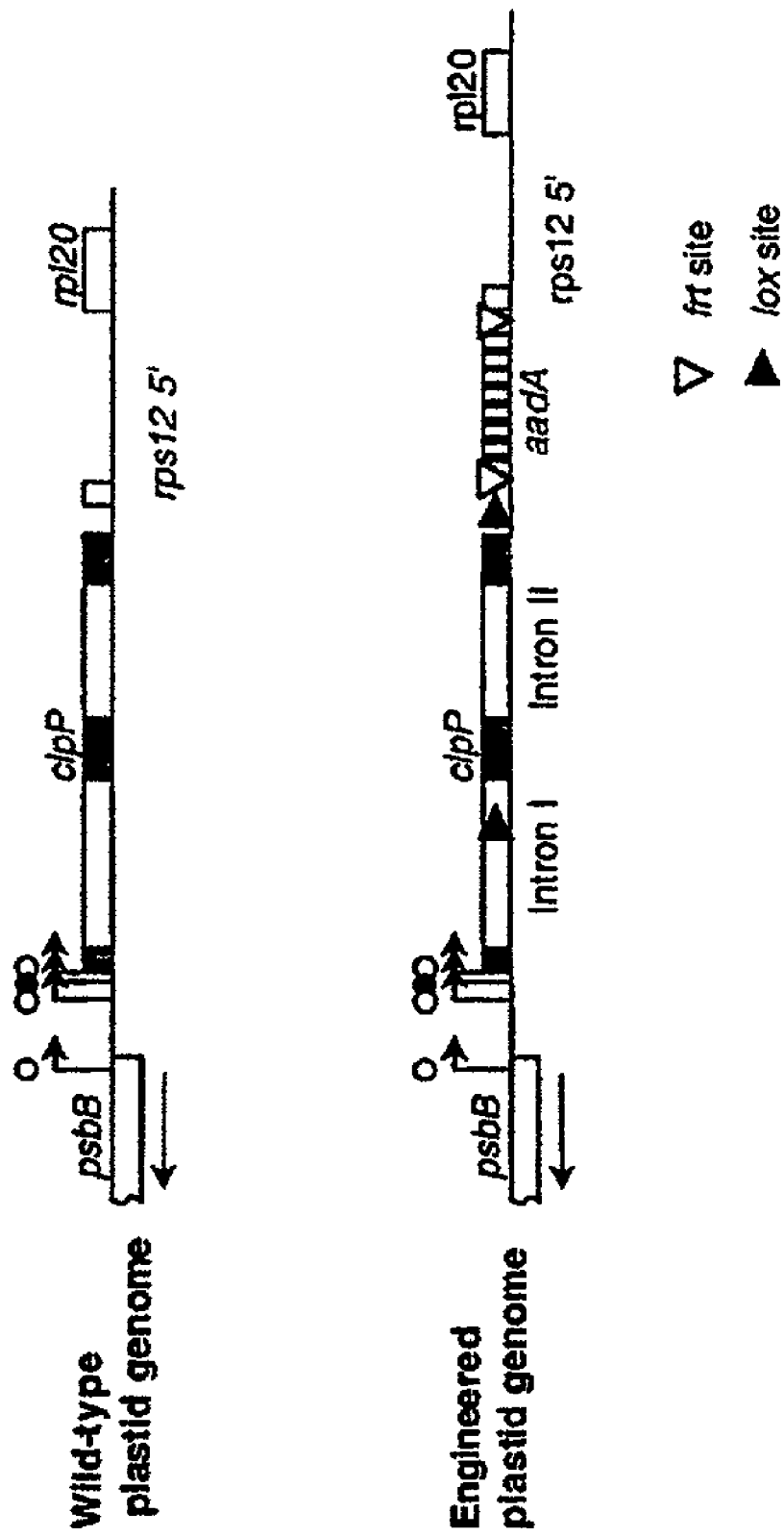
FIG. 20 shows a vector suitable for Cre-mediated deletion of clpP gene from the plastid genome. The region of engineered plastid genome shown is the sequence contained in the plastid transformation vector. The clpP Exons are dark boxes, the Introns are open boxes. Map position of plastid genes psbB, rps12 Exon I and rpl20 is also shown.
Figure 21:
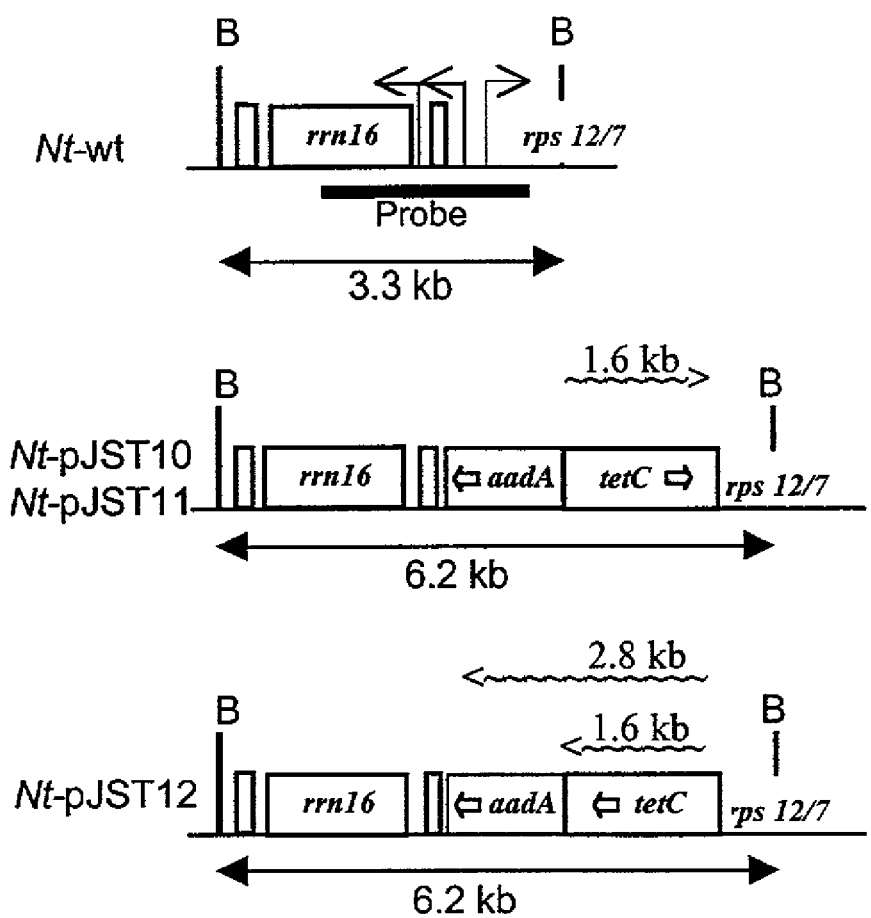
FIG. 21. Transformed plastid genomes with tetC gene. (A) The plastid tetC genes. (B) Map of wild-type (Nt-wt) and transformed plastid genomes. Horizontal arrows mark promoters in wild-type plastid genomes. Horizontal wavy lines represent TetC transcripts. Abbreviations: rrn16 and rps12/7 are plastid genes; aadA, spectinomycin resistance gene; tetC, tetC gene; B, BamHI site. (C) DNA gel blot analysis confirms integration of tetC in plastid genome. Total cellular DNA was digested with the BamHI restriction enzyme and the blots were probed with targeting region (rrn16-rps12 probe) and the aadA, tetC-AT and tetC-GC probes. Note that tetC gene probes do not cross-hybridize due to differences in codon usage.
Figure 21:
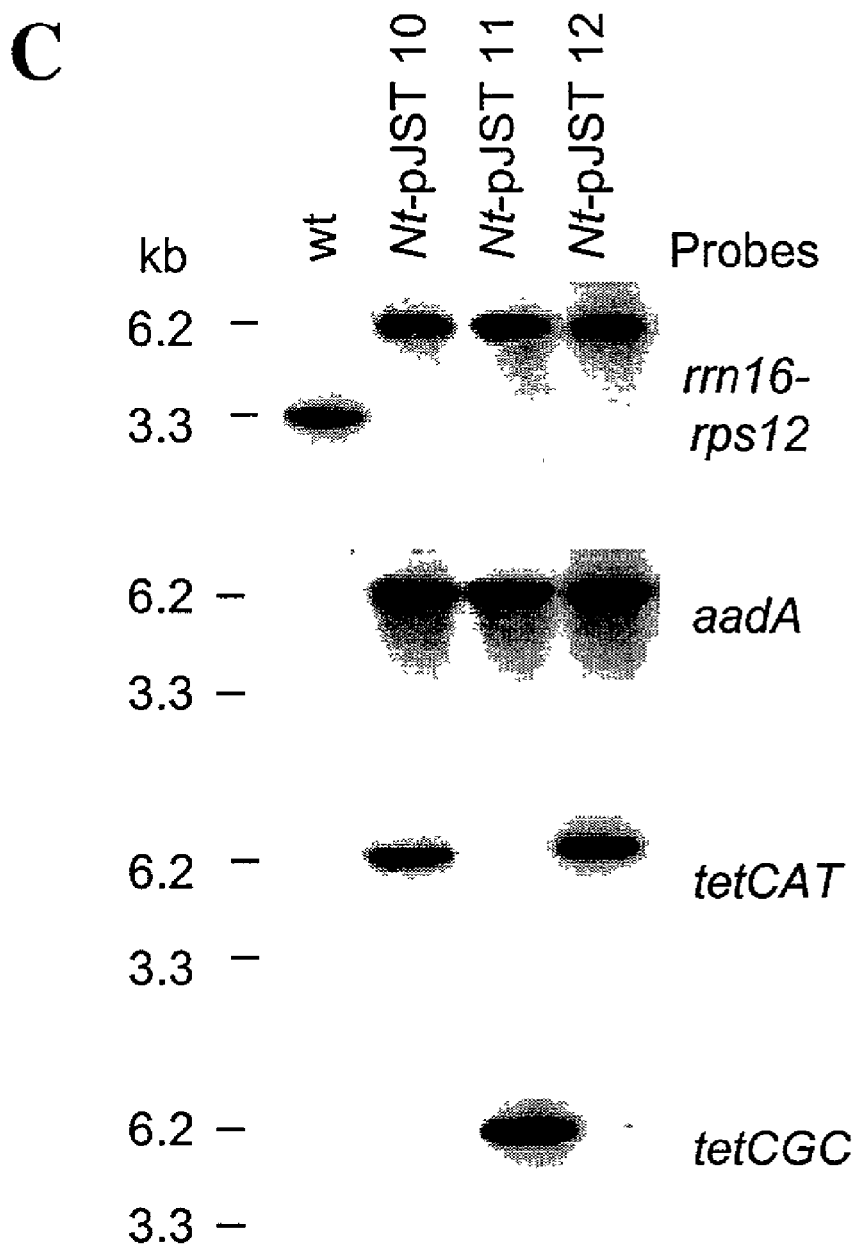
Figure 22:
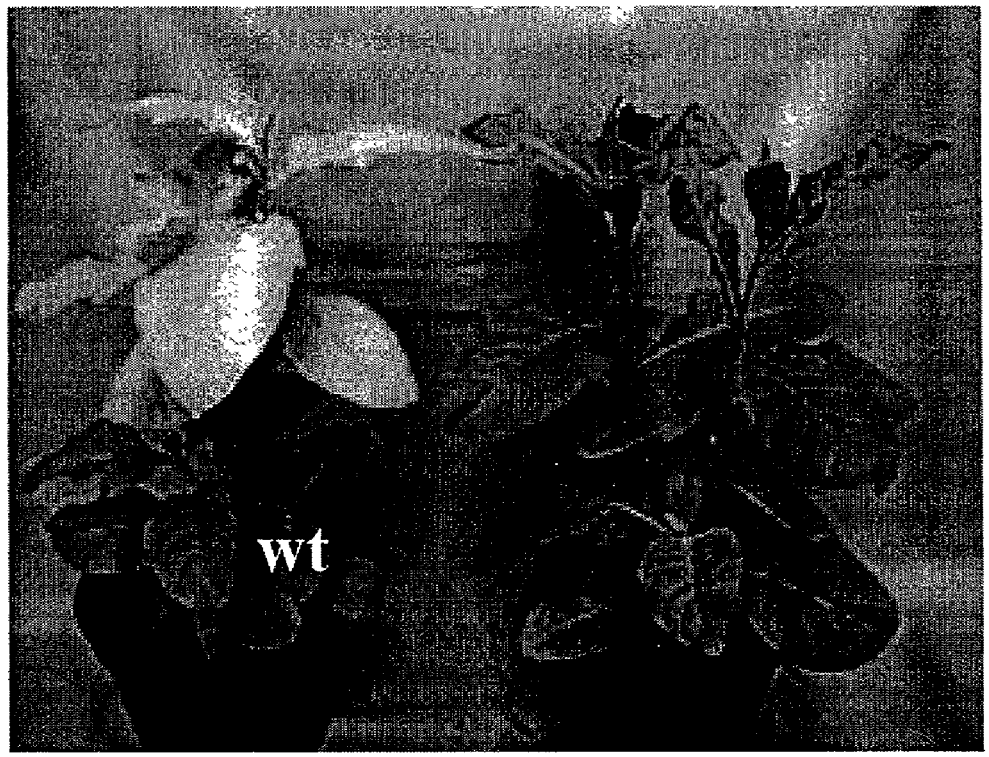
FIG. 22. High-level expression of TetC is detrimental to plants. Shown are an Nt-pJST10 shoot with chlorotic phenotype grafted onto wild-type plant (wt) and an Nt-pJST11 plant.
Figure 23:
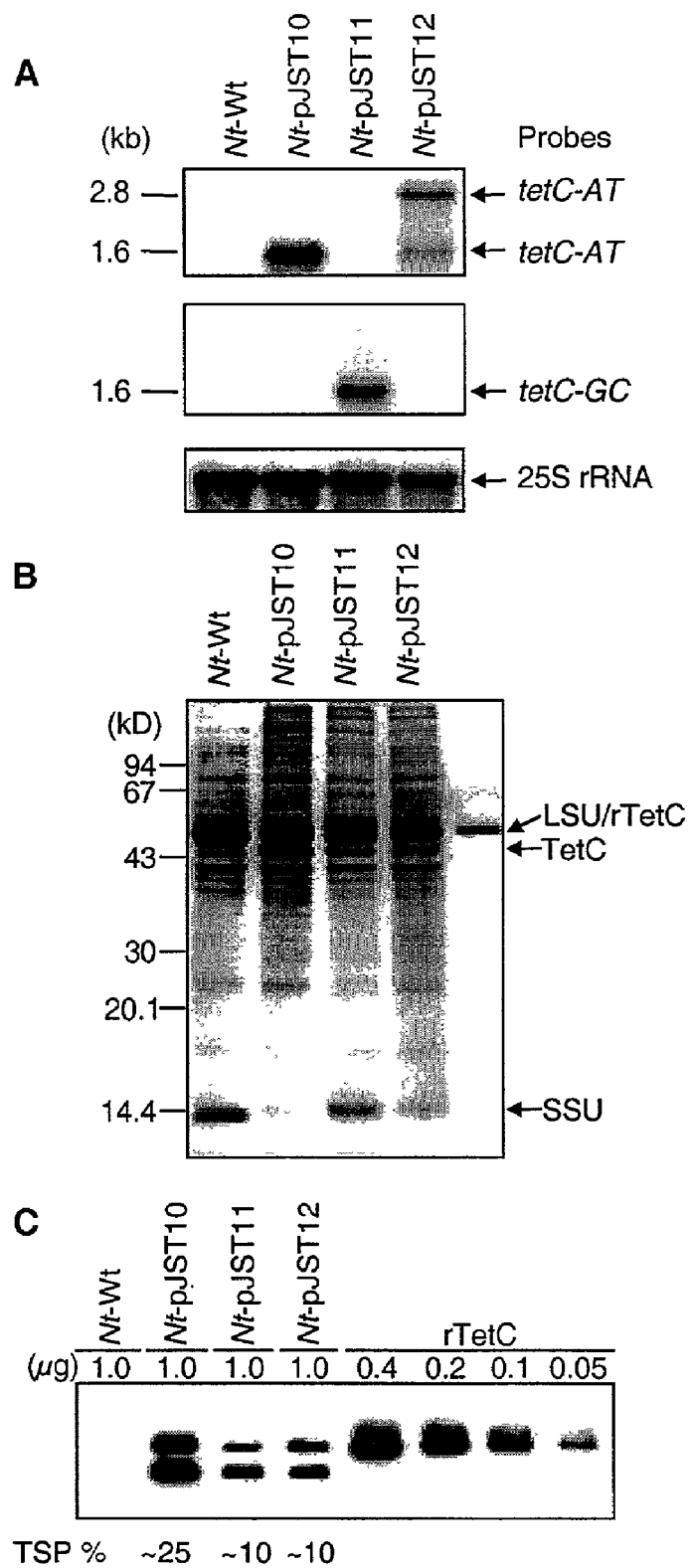
FIG. 23. Expression of tetC genes. (A) Accumulation of mRNA from the tetC genes. Monocistronic and dicistronic transcripts detected by the coding region probes are marked in FIG. 1B. Relative amounts of mRNAs were quantified using cytoplasmic 25S rRNA as reference. (B) Coomassie stained protein gel with novel plant-produced 43 kDa TetC band. Control rTetC and the Rubisco large and small subunits (LSU, SSU) are also marked. (C) Immunoblots to quantify TetC in leaf protein extracts.
Figure 24:
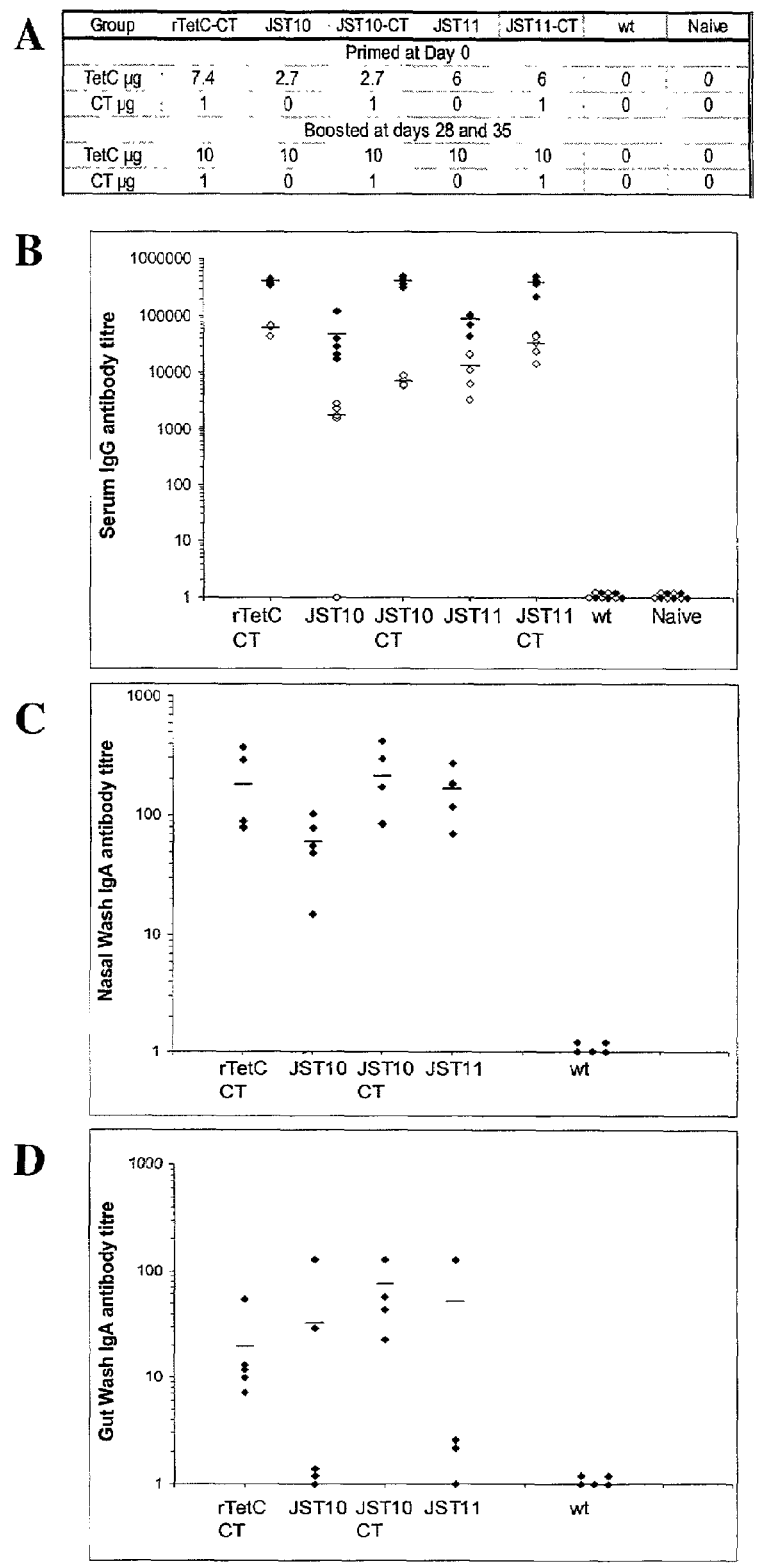
FIG. 24. Response to nasal vaccination with plant-produced TetC. (A) Immunization schedule and dosing. (B) Serum Anti-TetC IgG antibody titer indicates systemic immune response. (C) Nasal anti-TetC IgA titer. (D) Gut anti-TetC IgA titer. Open symbols are values after 27 days; filled symbols are values after 45 days. The bars are averages of five measurements.

To induce cellular death by CRE-mediated excision, directly oriented lox sites can be incorporated in the plastid genome flanking essential genes, as shown for clpP in FIG. 20. The clpP gene has two large introns (807 bp and 637 bp) and the region can be conveniently cloned as a SalI-SphI fragment. The selectable marker aadA is inserted into a KpnI restriction site created by PCR mutagenesis downstream of clpp Exon 3, oriented towards rps12 Exon I. One of the lox sites is engineered next to the aadA gene, the second lox site is inserted in Intron I. Cellular death is induced by activation of the nuclear Cre gene as described in U.S. Pat. No. 5,530,191. It is necessary to use a selective marker, such as aadA to introduce the lox sites into the plastid genome. The aadA gene can subsequently eliminated using a second, independent site specific recombinase such as FRT via the frt sites engineered into the transformation vector shown in FIG. 20.

Alternative targets for CRE-mediated deletion in a CMS system are the essential ribosomal protein genes such as rp123, the ribosomal RNA operon (for insertion sites see; Staub and Maliga 1992; Zoubenko et al. 1994) and the ycf1 and ycf2 genes (Drescher et al. 2000)

The following sequences are referred to throughout the specification and facilitate the practice of the present invention.

```
SEQ. No. 1: PrrnloxI. sequence
gagctcGCTCCCCCGCCGTCGTTCAATGAGAATGGATAAGAGGCTCGTGG
GATTGACGTGAGGGGGCAGGGATGGCTATATTTCTGGGAGCataacttcg
tataatgtatgctatacgaagttatctaga SEQ. No. 2: TrbcLloxI. sequence
gaattcataacttcgtatagcatacattatacgaagttatAGACATTAGC
AGATAAATTAGCAGGAAATAAAGAAGGATAAGGAGAAAGAACTCAAGTAA
TTATCCTTCGTTCTCTTAATTGAATTGCAATTAAACTCGGCCCAATCTTT
TACTAAAAGGATTGAGCCGAATACAACAAAGATTCTATTGCATATATTTT
GACTAAGTATATACTTACCTAGATATACAAGATTTGAAATACAAAATCTA
Gcaagcttggtacc SEQ. No. 3: cre coding region. sequence
gagctccATGgctagcTCC AATTTACTGA CCGTACACCA
AAATTTGCCT GCATTACCGG TCGATGCAAC GAGTGATGAG
GTTCGCAAGA ACCTGATGGA CATGTTCAGG GATCGCCAGG
```

```
-continued
CGTTTTCTGA GCATACCTGG AAAATGCTTC TGTCCGTTTG
CCGGTCGTGG GCGGCATGGT GCAAGTTGAA TAACCGGAAA
TGGTTTCCCG CAGAACCTGA AGATGTTCGC GATTATCTTC
TATATCTTCA GGCGCGCGGT CTGGCAGTAA AAACTATCCA
GCAACATTTG GGCCAGCTAA ACATGCTTCA TCGTCGGTCC
GGGCTGCCAC GACCAAGTGA CAGCAATGCT GTTTCACTGG
TTATGCGGCG GATCCGAAAA GAAAACGTTG ATGCCGGTGA
ACGTGCAAAA CAGGCTCTAG CGTTCGAACG CACTGATTTC
GACCAGGTTC GTTCACTCAT GGAAAATAGC GATCGCTGCC
AGGATATACG TAATCTGGCA TTTCTGGGGA TTGCTTATAA
CACCCTGTTA CGTATAGCCG AAATTGCCAG GATCAGGGTT
AAAGATATCT CACGTACTGA CGGTGGGAGA ATGTTAATCC
ATATTGGCAG AACGAAAACG CTGGTTAGCA CCGCAGGTGT
AGAGAAGGCA CTTAGCCTGG GGGTAACTAA ACTGGTCGAG
CGATGGATTT CCGTCTCTGG TGTAGCTGAT GATCCGAATA
ACTACCTGTT TTGCCGGGTC AGAAAAAATG GTGTTGCCGC
GCCATCTGCC ACCAGCCAGC TATCAACTCG CGCCCTGGAA
GGGATTTTTG AAGCAACTCA TCGATTGATT TACGGCGCTA
AGGATGACTC TGGTCAGAGA TACCTGGCCT GGTCTGGACA
CAGTGCCCGT GTCGGAGCCG CGCGAGATAT GGCCCGCGCT
GGAGTTTCAA TACCGGAGAT CATGCAAGCT GGTGGCTGGA
CCAATGTAAA TATTGTCATG AACTATATCC GTAACCTGGA
TAGTGAAACA GGGGCAATGG TGCGCCTGCT cGAgGATGGC
GATTAGtctaga SEQ. No. 4: PrrnloxD. Sequence
gagctcGCTCCCCCGCCGTCGTTCAATGAGAATGGATAAGAGGCTCGTGG
GATTGACGTGAGGGGGCAGGGATGGCTATATTTCTGGGAGCataacttcg
tataatgtatgctatacgaagttatgaattc SEQ. No. 5: TrbcLloxD. sequence
tctagataacttcgtataatgtatgctatacgaagttatAGACATTAGCA
GATAAATTAGCAGGAAATAAAGAAGGATAAGGAGAAAGAACTCAAGTAAT
TATCCTTCGTTCTCTTAATTGAATTGCAATTAAACTCGGCCCAATCTTTT
ACTAAAAGGATTGAGCCGAATACAACAAAGATTCTATTGCATATATTTTG
ACTAAGTATATACTTACCTAGATATACAAGATTTGAAATACAAAATCTAG
caagcttggtacc SEQ. No. 6: Pea ssuTP5. sequence
ccggatccAA TTCAACCACA AGAACTAACA AAGTCAGAAA
AATGGCTTCT ATGATATCCT CTTCCGCTGT GACAACAGTC
AGCCGTGCTT CTAGGGTGCA ATCCGCGGCA GTGGCTCCAT
TCGGCGGCCT GAAATCCATG ACTGGATTCC CAGTGAAGAA
GGTCAACACT GACATTACTT CCATTACAAG CAATGGTGGA
AGAGTAAAGT GCATGCAGGT GTGGCCTgcc atggctagc SEQ. No. 7: Pea ssuTP22. sequence
ccggatcc AA TTCAACCACA AGAACTAACA AAGTCAGAAA
AATGGCTTCT ATGATATCCT CTTCCGCTGT GACAACAGTC
AGCCGTGCTT CTAGGGTGCA ATCCGCGGCA GTGGCTCCAT
TCGGCGGCCT GAAATCCATG ACTGGATTCC CAGTGAAGAA
GGTCAACACT GACATTACTT CCATTACAAG CAATGGTGGA
AGAGTAAAGT GCATGCAGGT GTGGCCTCCA ATTGGAAAGA
AGAAGTTTGA GACTCTTTCC TATTTGCCAC CATTGACCat
ggctagc SEQ. No. 8: Pea ssuTP23. sequence
ccggatccAA TTCAACCACA AGAACTAACA AAGTCAGAAA
AATGGCTTCT ATGATATCCT CTTCCGCTGT GACAACAGTC
AGCCGTGCTT CTAGGGTGCA ATCCGCGGCA GTGGCTCCAT
TCGGCGGCCT GAAATCCATG ACTGGATTCC CAGTGAAGAA
GGTCAACACT GACATTACTT CCATTACAAG CAATGGTGGA
AGAGTAAAGT GCATGCAGGT GTGGCCTCCA ATTGGAAAGA
AGAAGTTTGA GACTCTTTCC TATTTGCCAC CATTGACCAG
AGATCAGTTG gctagcgg SEQ. No. 9: P2 promoter sequence
gaattCATTT TCACGTGTGG AAGATATGAA TTTTTTTGAG
AAACTAGATA AGATTAATGA ATATCGGTGT TTTGGTTTTT
TCTTGTGGCC GTCTTTGTTT ATATTGAGAT TTTTCAAATC
AGTGCGCAAG ACGTGACGTA AGTATCTGAG CTAGTTTTTA
TTTTTCTACT AATTTGGTCG TTTATTTCGG CGTGTAGGAC
ATGGCAACCG GGCCTGAATT TCGCGGGTAT TCTGTTTCTA
TTCCAACTTT TTCTTGATCC GCAGCCATTA ACGACTTTTG
AATAGATACG CTGACACGCC AAGCCTCGCT AGTCAAAAGT
GTACCAAACA ACGCTTTACA GCAAGAACGG AATGCGCGTG
ACGCTCGCGG TGACGCCATT TCGCCTTTTC AGAAATGGAT
AAATAGCCTT GCTTCCTATT ATATCTTCCC AAATTACCAA
TACATTACAC TAGCATCTGA ATTTCATAAC CAATTCTCGAT
ACACCAAATC GATaggatcc taccatgg
```

-continued

```
SEQ. No. 10: 35S promoter sequence
AAGCTTGCCA ACATGGTGGA GCACGACACT CTCGTCTACT
CCAAGAATAT CAAAGATACA GTCTCAGAAG ACCAAAGGGC
TATTGAGACT TTTCAACAAA GGGTAATATC GGGAAACCTC
CTCGGATTCC ATTGCCCAGC TATCTGTCAC TTCATCAAAA
GGACAGTAGA AAAGGAAGGT GGCACCTACA AATGCCATCA
TTGCGATAAA GGAAAGGCTA TCGTTCAAGA TGCCTCTGCC
GACAGTGGTC CCAAAGATGG ACCCCCACCC ACGAGGAGCA
TCGTGGAAAA AGAAGACGTT CCAACCACGT CTTCAAAGCA
AGTGGATTGA TGTGATAACA TGGTGGAGCA CGACACTCTC
GTCTACTCCA AGAATATCAA AGATACAGTC TCAGAAGACC
AAAGGGCTAT TGAGACTTTT CAACAAAGGG TAATATCGGG
AAACCTCCTC GGATTCCATT GCCCAGCTAT CTGTCACTTC
ATCAAAAGGA CAGTAGAAAA GGAAGGTGGC ACCTACAAAT
GCCATCATTG CGATAAAGGA AAGGCTATCG TTCAAGATGC
CTCTGCCGAC AGTGGTCCCA AAGATGGACC CCCACCCACG
AGGAGCATCG TGGAAAAAGA AGACGTTCCA ACCACGTCTT
CAAAGCAAGT GGATTGATGT GATATCTCCA CTGACGTAAG
GGATGACGCA CAATCCCACT ATCCTTCGCA AGACCCTTCC
TCTATATAAG GAAGTTCATT TCATTTGGAG AGGACACGCT
GAAATCACCA GTCTCTCTCT ACAAATCTAT CTCTCTCGAT
TCGCGAGCTC GGTACCCGGG gatcgatcc SEQ. No. 11: KpnI-loX-BglII-lox-HindIII fragment
ggtaccATAACTTCGTATAATGTATGCTATACGAAGTTATagatctATAA
CTTCGTATAATGTATGCTATACGAAGTTATaagctt Seq. ID No. 12. Translational coupling of bar and
aadA according to scheme in FIG. 18. BglII-SpeI
fragment.
GAGATCTGgg aggaataact tATGggggtc gacATAACTT
CGTATAATGT ATGCTATACG AAGTTATtaG AAGCGGTGAT
CGCCGAAGTA TCGACTCAAC TATCAGAGGT AGTTGGCGTC
ATCGAGCGCC ATCTCGAACC GACGTTGCTG GCCGTACATT
TGTACGGCTC CGCAGTGGAT GGCGGCCTGA AGCCACACAG
TGATATTGAT TTGCTGGTTA CGGTGACCGT AAGGCTTGAT
GAAACAACGC GGCGAGCTTT GATCAACGAC CTTTTGGAAA
CTTCGGCTTC CCCTGGAGAG AGCGAGATTC TCCGCGCTGT
AGAAGTCACC ATTGTTGTGC ACGACGACAT CATTCCGTGG
CGTTATCCAG CTAAGCGCGA ACTGCAATTT GGAGAATGGC
AGCGCAATGA CATTCTTGCA GGTATCTTCG AGCCAGCCAC
GATCGACATT GATCTGGCTA TCTTGCTGAC AAAAGCAAGA
GAACATAGCG TTGCCTTGGT AGGTCCAGCG GCGGAGGAAC
TCTTTGATCC GGTTCCTGAA CAGGATCTAT TTGAGGCGCT
AAATGAAACC TTAACGCTAT GGAACTCGCC GCCCGACTGG
GCTGGCGATG AGCGAAATGT AGTGCTTACG TTGTCCCGCA
TTTGGTACAG CGCAGTAACC GGCAAAATCG CGCCGAAGGA
TGTCGCTGCC GACTGGGCAA TGGAGCGCCT GCCGGCCCAG
TATCAGCCCG TCATACTTGA AGCTAGACAG GCTTATCTTG
GACAAGAAGA AGATCGCTTG GCCTCGCGCG CAGATCAGTT
GGAAGAATTT GTCCACTACG TGAAAGGCGA GATCACCAAG
GTAGTCGGCA AATAAATAAC TTCGTATAAT GTATGCTATA
CGAAGTTATa ctagt Seq. ID No. 13. CRE-induced expression of
recombinant protein according to design in FIG.
19. SacI-NheI fragment.
gagctcGCTC CCCCGCCGTC GTTCAATGAG AATGGATAAG
AGGCTCGTGG GATTGACGTG AGGGGGCAGG GATGGCTATA
TTTCTGGGAG AATTAACCGA TCGACGTGCa AGCGGACATT
TATTTTaAAT TCGATAATTT TTGCAAAAAC ATTTCGACAT
ATTTATTTAT TTTATTATTA TGgggATAAC TTCGTATAAT
GTATGCTATA CGAAGTTATt aGAAGCGGTG ATCGCCGAAG
TATCGACTCA ACTATCAGAG GTAGTTGGCG TCATCGAGCG
CCATCTCGAA CCGACGTTGC TGGCCGTACA TTTGTACGGC
TCCGCAGTGG ATGGCGGCCT GAAGCCACAC AGTGATATTG
ATTTGCTGGT TACGGTGACC GTAAGGCTTG ATGAAACAAC
GCGGCGAGCT TGATCAACG ACCTTTTGGA AACTTCGGCT
TCCCCTGGAG AGAGCGAGAT TCTCCGCGCT GTAGAAGTCA
CCATTGTTGT GCACGACGAC ATCATTCCGT GGCGTTATCC
AGCTAAGCGC GAACTGCAAT TTGGAGAATG GCAGCGCAAT
GACATTCTTG CAGGTATCTT CGAGCCAGCC ACGATCGACA
TTGATCTGGC TATCTTGCTG ACAAAAGCAA GAGAACATAG
CGTTGCCTTG GTAGGTCCAG CGGCGGAGGA ACTCTTTGAT
CCGGTTCCTG AACAGGATCT ATTTGAGGCG CTAAATGAAA
CCTTAACGCT ATGGAACTCG CCGCCCGACT GGGCTGGCGA
TGAGCGAAAT GTAGTGCTTA CGTTGTCCCG CATTTGGTAC
AGCGCAGTAA CCGGCAAAAT CGCGCCGAAG GATGTCGCTG
CCGACTGGGC AATGGAGCGC CTGCCGGCCC AGTATCAGCC
CGTCATACTT GAAGCTAGAC AGGCTTATCT TGGACAAGAA
GAAGATCGCT TGGCCTCGCG CGCAGATCAG TTGGAAGAAT
TTGTCCACTA CGTGAAAGGC GAGATCACCA AGGTAGTCGG
CAAATAAATA ACTTCGTATA ATGTATGCTA TACGAAGTTA
Ttagctagc
```

REFERENCES

Adams D E, Bliska J B, Cozzarelli N R (1992) Cre-lox recombination in *Escherichia coli* cells. Mechanistic differences from the in vitro reaction. J Mol Biol 226: 661–673

Albert H, Dale E C, Lee E, Ow D W (1995) Site-specific integration of DNA into wild-type and mutant lox sites placed in the plant genome. Plant J 7:649–659

Allison L A, Simon L D, Maliga P (1996) Deletion of rpoB reveals a second distinct transcription system in plastids of higher plants. EMBO J 15:2802–2809

Aoyama T, Chau N H (1997) A glucocorticoid-mediated transcriptional induction system in transgenic plants. Plant J 11:605–612

Baneyx F (1999) Recombinant protein expression in *Escherichia coli*. Curr Opin Biotechnol 10:411–421

Beck C F, Ingraham J L, Neuhard J, Thomassen E (1972) Metabolism of pyrimidines and pyrimidine nucleosides by *Salmonella typhimurium*. J Bacteriol 110:219–228

Bonham-Smith P C, Bourque D P (1989) Translation of chloroplast-encoded mRNA: potential initiation and termination signals. Nucleic Acids Res 17:2057–2080

Burrows P A, Sazanov L A, Svab Z, Maliga P, Nixon P J (1998) Identification of a functional respiratory complex in chloroplasts through analysis of tobacco mutants containing disrupted plastid ndh genes. EMBO J 17:868–876

Carrer H, Hockenberry T N, Svab Z, Maliga P (1993) Kanamycin resistance as a selectable marker for plastid transformation in tobacco. Mol Gen Genet 241:49–56

Carrer H, Maliga P (1995) Targeted insertion of foreign genes into the tobacco plastid genome without physical linkage to the selectable marker gene. Biotechnology 13:791–794

Carrer H, Staub J M, Maliga P (1990) Gentamycin resistance in Nicotiana conferred by AAC(3)-I, a narrow substrate specificity acetyl transferase. Plant Mol Biol 17:301–303

Craig N L (1988) The mechanism of conservative site-specific recombination. Annual Review Of Genetics 22:77–105

Dale E C, Ow D W (1991) Gene transfer with subsequent removal of the selection gene from the host genome. Proc Natl Acad Sci USA 88:10558–10562

Depicker A G, Jacobs A M, Montagu M C (1988) A negative selection scheme for tobacco protoplast-derived cells expressing the T-DNA gene 2. Plant Cell Rep 7:63–66

Drescher A, Ruf S, Calsa T, Carrer H, Bock R (2000) The two largestchloroplast genome-encoded open reading frames of higher plants are essential genes. The Plant Journal 22:97–104

Dršge M, PŸhler A, Selbitschka W (1998) Horizontal gene transfer as a biosafety issue: a natural phenomenon of public concern. J Biotechnol 64:75–90

Gatz C (1997) Chemical control of gene expression. Ann Rev Plant Physiol Plant Mol Biol 48:89–108

Gatz C, Frohberg C, Wendenburg R (1992) Stringent repression and homogeneous de-repression by tetracycline of a modified CaMV 35S promoter in intact transgenic tobacco plants. Plant J 2:397–404

Hajdukiewicz P, Svab Z, Maliga P (1994) The small, versatile pPZP family of *Agrobacterium* binary vectors for plant transformation. Plant Mol Biol 25:989–994

Hoess R H, Ziese M, Sternberg N (1982) P1 site-specific recombination: nucleotide sequence of the recombining sites. Proc Natl Acad Sci USA 79:3398–3402

Huang C, Wang S. Chen L, Lemioux C, Otis C, Turmel M, Liu XQ (1994) The *Chlamydomonas* chloroplast clpP gene contains translated large insertion sequences and is essential for cell growth. Molecular and Genetal Genetics 244:151–159

Kanevski I, Maliga P (1994) Relocation of the plastid rbcL gene to the nucleus yields functional ribulose-1,5-bisphosphate carboxylase in tobacco chloroplasts. Proc Natl Acad Sci USA 91:1969–1973

Karlin-Neumann G A, Brusslan J A, Tobin E M (1991) Phytochrome control of the tms2 gene in transgenic *Arabidopsis*: a strategy for selecting mutants in the signal transduction pathway. Plant Cell 3:573–582

Khan M S, Maliga P (1999) Fluorescent antibiotic resistance marker to track plastid transformation in higher plants. Nat Biotechnol 17:910–915

Kolb A F, Siddell S G (1996) Genomic targeting with an MBP-Cre fusion protein [published erratum appears in Gene 1997 Apr 11;189(1):149]. gene 183:53–60

Le Y, Gagneten S, Tombaccini D, Bethke B, Sauer B (1999) Nuclear targeting determinants of the phage P1 Cre DNA recombinase. Nucleic Acids Res 27:4703–4709

Lichtenstein C, Barrena E (1993) Prospects for reverse genetics in plants using recombination [news]. Plant Mol Biol 21:v-xii Love J. Scott A C, Thompson W F (2000) Stringent control of transgene expression in *Arabidopsis thaliana* using the Top10 promoter system. Plant J 21:579–588

Lubben T H, Gatenby A A, Ahlquist P, Keegstra K (1989) Chloroplast import characteristics of chimeric proteins. Plant Mol Biol 12:13–18

Lyznik L A, Hirayama L, Rao K V, Abad A, Hodges T K (1995) Heat-inducible expression of FLP gene in maize cells. Plant J 8:177–186

Lyznik L A, Mitchell J C, Hirayama L, Hodges T K (1993) Activity of yeast FLP recombinase in maize and rice protoplasts. Nucleic Acids Res 21:969–975

Lyznik L A, Rao K V, Hodges T K (1996) FLP-mediated recombination of FRT sites in the maize genome. Nucleic Acids Res 24:3784–3789

Maliga P (1993) Towards plastid transformation in higher plants. Trends Biotech 11:101–107

Martinez A, Sparks C, Hart C A, Thompson J, Jepson I (1999) Ecdysone agonist inducible transcription in transgenic tobacco plants. Plant J 19:97–106

Mett V L, Lochhead L P, Reynolds PHS (1993) Copper-controllable gene expression for whole plants. Proc Natl Acad Sci USA 90:4567–4571

Morris A C, Schaub T L, James A A (1991) FLP-mediated recombination in the vector mosquito, Aedes aegypti. Nucleic Acids Res 19:5895–5900

Nussaume L, Vincentz M, Caboche M (1991) Constitutive nitrate reductase: a dominant conditional marker for plant genetics. Plant J 1:267–274

O'Gorman S, Fox D T, Wahl G M (1991) Recombinase-mediated gene activation and site-specific integration in mammalian cells. Science 251:1351–1355

Omer C A, Diehl R E, Kral A M (1995) Bacterial expression and purification of human protein prenyltransferases using epitope-tagged, translationally coupled systems. Meth Enzymol 250:3–12

Perera R J, Linard C G, Signer E R (1993) Cytosine deaminase as a negative selective marker for *Arabidopsis*. Plant Mol Biol 23:793–799

Russell S H, Hoopes J L, Odell J T (1992) Directed excision of a transgene from the plant genome. Mol Gen Genet 234:49–59

Schoner B E, Belagaje R M, Schoner R G (1986) Translatrion of a synthetic two-cidstron mRNA in *Escherichia coli*. Proc Natl Acad Sci USA 83:8506–8510

Serino G, Maliga P (1997) A negative selection scheme based on the expression of cytosine deaminase in plastids. Plant J 12:697–701

Shikanai T, Endo T, Hashimoto T, Yamada Y, Asada K, Yokota A (1998) Directed disruption of the tobacco ndhB gene impairs cyclic electron flow around photosystem I. Proc Natl Acad Sci USA 95:9705–9709

Shinozaki K, Ohme M, Tanaka M, Wakasugi T, Hayashida N, Matsabayashi T, Zaita N, Chungwongse J, Obokata J, Yamaguchi-Shinozaki K, Deno H, Kamogashira T, Yamada K, Kasuda J, Takaiwa F, Kato A, Todoh N, Shimada H, Sugiura M (1986) The complete sequence of the tobacco chloroplast genome: its gene organization and expression. EMBO J 5:2043–2049

Small I, Wintz H, Akashi K, Mireau H (1998) Two birds with one stone: genes that encode products targeted to two or more compartments. Plant Mol Biol 38:265–277

Soll J, Tien R (1998) Protein translocation into and across the chloroplastic envelope membranes. Plant Mol Biol 38:191–207

Sriraman P (2000) Identification and characterization of components of the plastid transcription machinery. Identification and characterization of components of the plastid transcription machinery.Rutgers University, Piscataway, N.J.

Srivastava V, Anderson O D, Ow D W (1999) Single-copy transgenic wheat generated trough the resolution of complex integration patterns. Proceedings of the National Academy of Sciences 96:11117–11121

Staub J M, Maliga P (1992) Long regions of homologous DNA are incorporated into the tobacco plastid genome by transformation. Plant Cell 4:39–45

Staub J M, Maliga P (1995) Expression of a chimeric uida gene indicates that polycistronic mRNAs are efficiently translated in tobacco plastids. Plant J 7:845–848

Stougaard J (1993) Substrate-dependent negative selection in plants using a bacterial cytosine deaminase gene. Plant J 3:755–761

Stricklett P K, Nelson R D, Kohan D E (1998) Site-specific recombination using an epitope tagged bacteriophage P1 Cre recombinase. gene 215:415–423

Sundaresan V, Springer P, Volpe T, Haward S, Jones J D, Dean C, Ma H, Martienssen R (1995) Patterns of gene action in plant development revealed by enhancer trap and gene trap transposable elements. Genes Dev 9:1797–1810

Svab Z, Harper E C, Jones J D, Maliga P (1990) Aminoglycoside-3"-adenyltransferase confers resistance to spectinomycin and streptomycin in Nicotiana tabacum. Plant Mol Biol 14:197–205

Svab Z, Maliga P (1993) High-frequency plastid transformation in tobacco by selection for a chimeric aadA gene. Proc Natl Acad Sci USA 90:913–917

Sylvanen M (1999) In search of horizontal gene transfer. Nat Biotechnol 17:833

Tepfer D (1989) Ri T-DNA from *Agrobacterium rhizogenes*: a source of genes having applications in rhizosphere biology and plant development, ecology and evolution. In: Kosuge T, Nester E W (eds) *Plant-Microbe Interac-* tions. *Molecular and Genetic Perspectives*, Vol. 3, McGraw-Hill, New York, pp 294–342

Timko M P, Kaush A P, Hand J M, Cashmore A R (1985) Structure and expression of nuclear genes encoding polypeptides of the photosynthetic apparatus. In: Steinback K E, Bonitz S, Arntzen C J, Bogorad L (eds) *Molecular biology of the photosynthetic apparatus.*, Cold Spring Harbor Laboratory, Cold Spring Harbor, pp 381–396.

Timmermans M C P, Maliga P, Vieira J, Messing J (1990) The pFF plasmids: cassettes utilizing CaMV sequences for expression of foreign genes in plants. J Biotechnol 14:333–344.

van Haaren M J, Ow D W (1993) Prospects of applying a combination of DNA transposition and site-specific recombination in plants: a strategy for gene identification and cloning. Plant Mol Biol 23:525–533

Velten J, Velten L, Hain R, Schell J (1984) Isolation of a dual plant promoter fragment from the Ti plasmid of *Agrobacterium tumefaciens*. EMBO J 3:2723–2730.

Wasmann C C, Reiss B, Bartlett S G, Bohnert H J (1986) The import of the ransit peptide and the transportrf protein for protein import into chloroplasts. Mol Gen Genet 205:446–453

Wimmer B, Lottspeich F, van der Klei I, Veenhuis M, Gietl C (1997) The glyoxysomal and plastid molecular chaperones (70-kDa heat shock protein) of watermelon cotyledons are encoded by a single gene. Proc Natl Acad Sci USA 94:13624–13629

Xiang C, Guerra D J (1993) The anti-nptII gene. A potential negative selective marker for plants. Plant Physiol 102: 287–293

Zoubenko O V, Allison L A, Svab Z, Maliga P (1994) Efficient targeting of foreign genes into the tobacco plastid genome. Nucleic Acids Res 22:3819–3824

EXAMPLE 5

Production of Mucosal Tetanus Vaccine from Plant Chloroplasts

Toward the end of the nineteenth century, it became evident that certain species of clostridia were agents of human or animal disease. Like other members of the group, the pathogenic clostridia are normal soil inhabitants, with little or no invasive power; the diseases they produce result from the production of a variety of highly toxic proteins (exotoxins). Indeed, botulism (caused by *C. botulinum*) and less serous types of clostridal food poisoning (caused by *C. perfringens*) are pure intoxications, resulting from the ingestion of foods in which these organisms have previously developed and formed exotoxins. The other principal clostridial disease, tetanus, (caused by *C. tetani*) and gas gangrene (caused by several other species) are the results of wound infections; tissue damage leads to the development of an anaerobic environment which permits localized growth and toxin formation by these oganisms. Some clostridial toxins (those responsible for botulism and tetanus) are potent inhibitors of nerve function.

Despite the availability of an injectable vaccine, tetanus is still a common disease in many parts of the world, particularly in neonates where approximately 215,000 deaths occur annually. Current licensed tetanus vaccines are based on chemically inactivated tetanus toxin mixed with an alumbased adjuvant delivered by injection. Problems with the current vaccine include the need for multiple doses and boosters, dependence on a functional cold chain and the potential infection hazards associated with unsafe injections (Jacobs 2001). The types of problems associated with current tetanus vaccines are now recognized by international agencies as a generic global barrier preventing the efficient delivery of all vaccines to the needy in developing countries where the infrastructure is poor (see World Wide Web at vaccinealliance.org).

In response to these problems, there has been increased interest in vaccination regimes that avoid the use of needles and dependence on the cold chain. One possible route is to develop practical mucosal (oral, intranasal) vaccines, as they can potentially generate both local (mucosal) and systemic immunity (Levine and Dougan 1998). Of particular relevance in the developing world is the development of edible vaccines expressed in plants. Antigens expressed as components of experimental plant-based vaccines include the B subunit of *E. coli* heat-labile enterotoxin (LTB) (Haq et al. 1995), Norwalk virus-like particles (Mason et al. 1996; Tacket et al. 2000), hepatitis B virus particles (Mason et al. 1992; Thanavala et al. 1995; Kong et al. 2001) and a rotavirus enterotoxin/enterotoxigenic *E. coli* fimbrial antigen fusion (Yu and Langridge 2001). In addition, induction of go oral tolerance to autoantigens in the treatment of autoimmune diseases has been explored (Ma et al. 1997). These plant-based vaccines would have the advantage of being cheap, easy to produce and more stable to heat (Giddings et al. 2000; Ma 2000; Walmsley and Arntzen 2000). Initial developments in the field of plant-based vaccines have been limited by low level of immunogen expression from nuclear genes. An alternative method is to express vaccine antigen from the chloroplast genome. Chloroplast-based expression systems offer significant advantages over nuclear expression. These advantages include potentially high levels of vaccine antigen expression, restriction of spread in the environment due to maternal inheritance, specific gene targeting technology avoiding 'position effects', the use of operons to express multiple antigens, and the ability to remove undesirable selective markers (Heifetz 2000; Bock 2001; Maliga 2002). Methods for removing selectable marker genes are described in the previous examples.

Several recombinant tetanus vaccines have been tested for efficacy. Most of these are based on the Fragment C domain of the tetanus toxin (TetC), a non-toxic 47 kDa polypeptide fragment shown to induce a protective immune response following parenteral immunization with preparations from *E. coli* (Makoff et al. 1989), yeast (Romanos et al. 1991) and insect cells (Charles et al. 1991). In accordance with the present invention, a plant-plastid based mucosal tetanus vaccine has been developed based on recombinant TetC expression in the plant chloroplast. Subsequently, we show that nasal immunization with transgenic plants expressing TetC can induce significant levels of anti-TetC antibodies in the serum of orally or intranasally immunized mice and protect intranasally immunized mice against tetanus.

TetC was expressed from transgenes in tobacco chloroplasts. Depending on the choice of 5'-untranslated region and base composition of the coding region, TetC accumulated at levels of ~10% or >25% of the total soluble cellular protein. Plants accumulating 10% TetC were normal, whereas expression of TetC at >25% compromised plant growth. Plant derived TetC was tested for mucosal immunogenicity in mice applying a protein extract intranasally and total plant tissue orally. Both immunization regimes were found to induce local and systemic anti-TetC antibodies and levels of anti-TetC antibodies were sufficient to protect mice against a lethal tetanus toxin challenge. Thus, expression of TetC in transplastomic tobacco leaves provides a potential route towards the development of a mucosal tetanus vaccine.

The following materials and methods are provided to facilitate the practice of Example 5.

Construction of transformation vectors. The TetC polypetide was expressed in chloroplasts from two different mRNAs: the C-terminus of the AT-rich bacterial gene (tetC-AT) (Sequence ID No.31) and the synthetic relatively GC-rich sequence optimized for expression in the nucleus (Sequence ID No.32). The tetC coding regions were PCR amplified to introduce an NdeI site including the translation initiation codon (ATG) and an XbaI site downstream of the stop codon. The primers used for PCR amplification of tetC-AT were: 5'-CGGGTACCCATATGAAAAATCTGGATTGTTGGGTCGACAATGAAG-3' (SEQ ID NO:47) and 5'-CGTCTAGAAATTAATCATTTGTCCATC-3' (SEQ ID NO:48). The tetC-GC coding region was PCR amplified by primers 5'-CGGGTACCCATATGAAAAACCTTGATTGTTGG-3' (SEQ ID NO:49) and 5'-GCTCTAGATTAGTCGTTGGTCCAACCT-3' (SEQ ID NO:50). Templates for PCR amplification were plasmid pcDNA3/ntetC (tetC-AT') (Stratford et al. 2001) and pcDNA3/tetC (tetC-GC') (Anderson et al. 1996).

Plasmids pJST10 and pJST11 were obtained by replacing the neo coding region in plasmid pHK40 with the tetC-AT and tetC-GC coding regions as an NdeI-XbaI fragments. Plasmid pHK40 is a plastid transformation vector derived from plasmid pPRV111A (Kuroda and Maliga 2001a) with a spectinomycin resistance (aadA) gene as a selective marker and a neo gene expressed in a cassette consisting of a PrrnLT7g10 cassette and the rbcL 3'-UTR (TrbcL). The tetC genes are divergently oriented relative to the rrn operon (FIG. 21B).

Plasmid pJST12 was obtained by replacing the neo coding region in plasmid pHK73 with the tetC-AT coding region as an NdeI-XbaI fragment (SEQ. ID No:31). Plastid transformation vector pHK73 is a pPRV111B vector derivative in which the neo coding region is expressed in a cassette consisting of a PrrnLatpB cassette (plastid rrn operon promoter fused with atpB leader and an NdeI site including the ATG) and TrbcL. The PrrnLatpB cassette is identical with the cassette in plasmid pHK10 (Kuroda and Maliga 2001b), except that an NdeI site was created by replacing AT with a CA at the -3/-2 position upstream of the ATG. The tetC gene in plasmid pJST12 is in tandem orientation with the rrn operon (FIG. 21B).

Plastid transformation. Plastid transformation was carried out as described (Svab and Maliga 1993). DNA for plastid transformation was prepared using the QIAGEN Plasmid Maxi Kit (QIAGEN Inc., Valencia, Calif.). Transforming DNA was introduced into leaf chloroplasts on the surface of tungsten particles (1 μm) using the Du Pont PDS1000He Biolistic gun. Transplastomic plants were selected on RMOP medium containing 500 mg L-1 spectinomycin dihydrochloride. The transgenic plants were grown on MS (Murashige-Skoog) medium (Murashige and Skoog 1962) containing 3% (w/v) sucrose and 0.6% (w/v) agar in sterile culture condition. A uniform population of transformed plastid genome copies was confirmed by DNA gel blot analysis. Double-stranded DNA probes were prepared by random-primed $^{32}P$-labeling using the Ready-To-Go DNA Labeling Beads (Amershem Pharmacia Biotech, Piscataway, N.J.). The probes were: rrn16-rps12 plastid targeting region, ApaI-EcoRV ptDNA fragment; aadA, NcoI-XbaI coding region; tetC-AT and tetC-GC coding region, NdeI-XbaI fragments.

RNA Gel Blot Analysis. RNA gel blot analysis was carried out as described by loading 3 μg total cellular RNA per lane (Silhavy and Maliga 1998). The templates for probing the tetC genes were NdeI-XbaI coding region fragments. The template for probing the tobacco cytoplasmic 25S rRNA was a PCR fragment amplified from total tobacco cellular DNA with primers 5'-TCACCTGCCGAATCAACTAGC-3' (SEQ ID NO:51) and 5'-GACTTCCCTTGCCTACATTG-3' (SEQ ID NO:52). Probes were prepared by random-primed 32P-labeling (see above). RNA hybridization signals were quantified using a Molecular Dynamics PhosphorImager and normalized to the 25S rRNA signal.

SDS-PAGE and Immunoblotting. Leaves for protein extraction were taken from greenhouse plants. To obtain total soluble leaf protein, about 200 mg leaf was homogenized in 1 ml buffer containing 50 mM Hepes/KOH (pH 7.5), 10 mM potassium acetate, 5 mM magnesium acetate, 1 mM EDTA, 1 mM DTT and 2 mM PMSF. Protein concentrations were determined by the Pierce Bradford's Plus assay (Pierce, Rockford, Ill.). Immunoblot analysis of TetC accumulation was carried out as described (Carrer et al. 1993). The anti-TetC antibody was provided by Dr. C. Turcotte, Imperial College, London. TetC was quantified on the immunoblots by densitometric analysis with the Phoretix 1Dfull program using the Personal Densitometer SI (Molecular Dynamics, Amersham Pharmacia Biotech, Sunnyvale, Calif., USA) by comparison with a recombinant TetC (rTetC) dilution series. Purified His-tagged rTetC was kindly provided by Mr. O. Qazi, Imperial College, London.

Nasal and oral immunization of mice. All mice were obtained from B & K suppliers (Scunthorpe, UK). For nasal immunization, a 15 μl volume of concentrated protein suspension from plants expressing TetC or appropriate controls was applied to BALB-C female mice, 7.5 μl per nare. Protein extracts were prepared as for SDS-PAGE and concentrated using a Centriprep YM-10 (Millipore Ltd., Watford, UK). Mice were tail-bled at day 27, and samples stored at −20° C. until assayed. On day 45, the mice were sacrificed by exsanguination of the heart to collect serum samples. Gut, lung and nasal washes were taken at the same time, in 1 ml, 1 ml and 0.5 ml phosphate buffered saline, pH7.2 (PBS), containing protease inhibitors, Roche Complete protease inhibitor cocktail (Roche Diagnostics Ltd., Mannheim, Germany). For oral immunization either 50 mg or 100 mg of Nt-pJST11 tobacco plant material was finely ground in liquid nitrogen and resuspended in 200 μl of PBS. This was then introduced to BALB-C female mice by oral gavage. Two priming doses were used on day 0 and day 3. A sample tail bleed was taken on day 27. The mice were then boosted at day 28 and day 35. On day 45, the mice were sacrificed by exsanguination of the heart to collect serum samples. Lung and gut washes performed, with 1 ml PBS containing protease inhibitors, Roche Complete protease inhibitor cocktail (Roche Diagnostics Ltd., Mannheim, Germany). All samples were stored at −20° C. until required. Cholera toxin (CT) was added to nasal (lug per dose) and oral (10 μg per dose) vaccines to act as mucosal adjuvant. Control TetC (rTetC) for mucosal immunization was prepared from *E. coli*. For tetanus toxin challenge mice were injected subcutaneously in the right flank with 0.5 ml PBS containing 50 PD50 of tetanus toxin (kindly provided by Dr Thea Sesardic, NIBSC) and sacrificed as soon as they showed symptoms of paralysis.

ELISAs for anti-TetC antibodies. Samples were assayed for anti-TetC IgG in serum and anti-TetC IgA in mucosal surface washes as described (Douce et al. 1997). For IgG measurements samples were serially diluted in PBS containing 0.05% Tween-20 (PBST), for IgA readings, samples were serially diluted in PBST containing protease inhibitors; Roche Complete protease inhibitor cocktail. Microtiter plates were coated with 3 μg/μl TetC. Serum anti-tetC was determined with goat anti mouse IgG (γ chain specific) antisera conjugated with alkaline phophatase (Sigma-Aldrich, Dorset, UK). Mucosal anti tetC IgA was determined with goat antiserum against mouse IgA (α-chain specific) conjugated to streptavidin (Sigma-Aldrich, Dorset, UK), this was then detected with biotinylated alkaline phosphatase (Dako, Ely, UK). Response was measured against the color change of OPD reagent (Sigma-Aldrich, Dorset UK). Antibody titer was defined as the reciprocal of the dilution of antibody that produces an A490 of 0.3 for IgG readings and A490 of 0.2 for IgA readings.

Results

Figure 25:
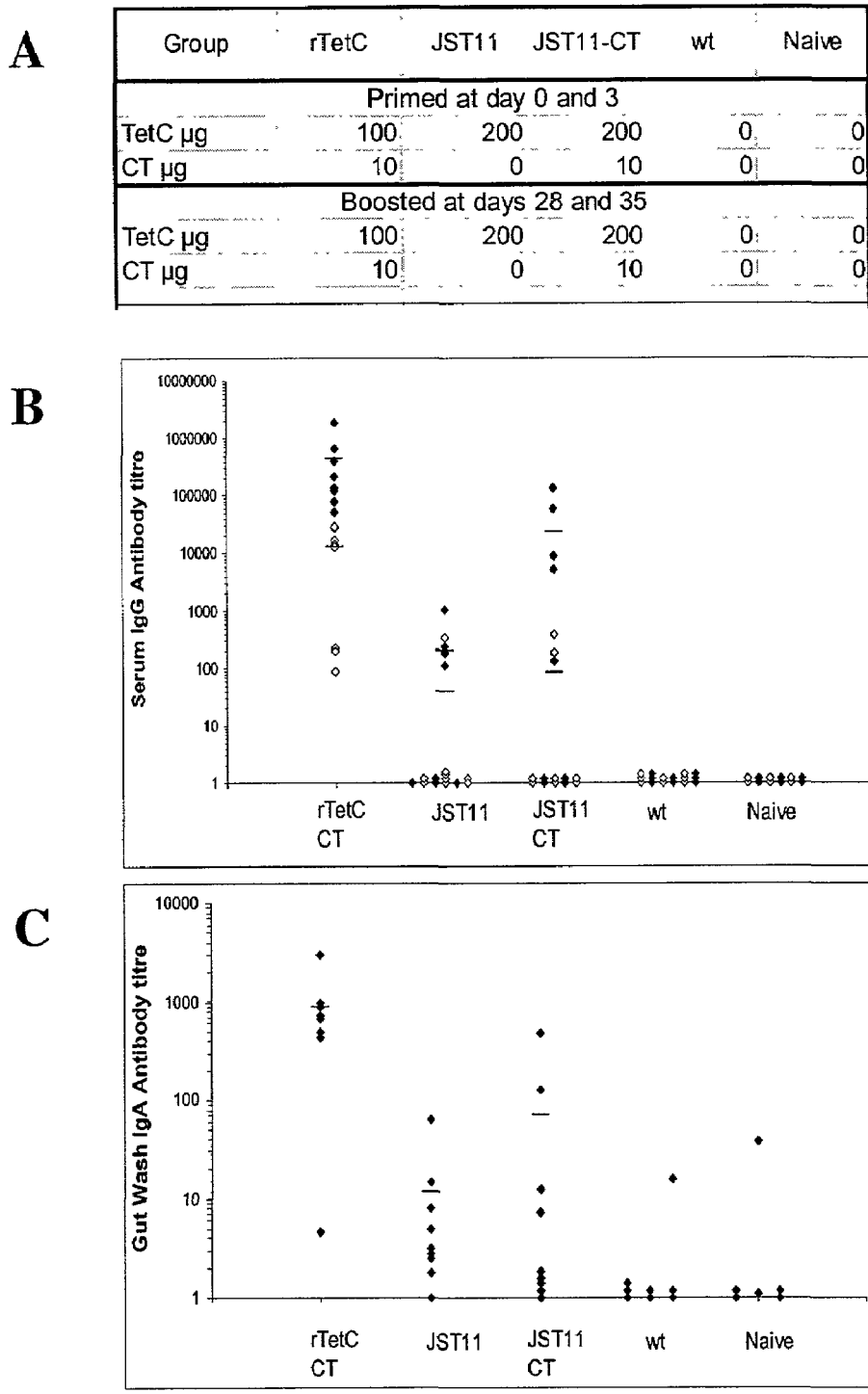
FIG. 25. Response to oral vaccination with plant-produced TetC. (A) Immunization schedule and dosing. (B) Serum anti-TetC IgG antibody titer. (C) Gut anti-TetC IgA titer. Open symbols are values after 27 days; filled symbols are values after 45 days. The bars are average s of five measurements.

Construction of transplastomic tobacco plants with tetC genes. The TetC polypeptide was expressed in tobacco chloroplasts from three different genes (FIG. 21A). Plastid vectors pJST10 and pJST12 encode the AT-rich tetC (72.3% AT; tetC-AT) natural coding region derived from *Clostridium* tetani. Vector pJST11 encodes a more GC-rich synthetic version of the tetC reading frame (52.6% AT; tetC-GC) originally codon-optimized for expression in yeast (Romanos et al. 1991). The tetC coding regions were expressed in cassettes with Prrn, the strong plastid rRNA operon promoter and TrbcL, the 3'-UTR of the plastid rbcL gene to stabilize the mRNAs. The expression cassettes also differ with respect to their 5'-UTR, which either derives from the phage T7 gene 10 (pJST10, pJST11) or the tobacco plastid gene atpB (pJST12). In the plastid transformation vectors the tetC genes are physically linked with a selectable spectinomycin resistance (aadA) gene and are targeted for insertion into the trnV/rps12/7 intergenic region (FIG. 21B). The vectors encoding the tetC genes were introduced into the tobacco plastid genome by standard protocols. Incorporation of the tetC genes in the plastid genome and the absence of untransformed wild-type genome copies was confirmed by DNA gel blot analysis (FIG. 21C). Several, independently transformed lines were obtained with each of the constructs. Since plants transformed with the same construct were similar, data are shown only for one representative transformed clone. Plants transformed with vectors pJST11 and pJST12 (Nt-pJST11, Nt-pJST12) are similar to the wild type, non-transformed plants. In contrast, Nt-pJST10 plants grow slower in the greenhouse and have a chlorotic (pigment deficient) phenotype (FIG. 22).

Expression of the tetC genes in chloroplasts. RNA gel blot analysis confirmed transcript accumulation for each of the three tetC genes (FIG. 23A) The Nt-pJST10 and Nt-pJST11 plants contain monocistronic messages, whereas the Nt-pJST12 plants accumulate both monocistronic and dicistronic transcripts due to read-through transcription through TrbcL (FIG. 21B). Steady-state tetC transcript levels in the Nt-pJST10 and Nt-pJST12 leaves were comparable (FIG. 23A). Relative amounts of tetC-GC transcripts in the Nt-pJST11 plants could not be determined, as the coding region probes did not cross-hybridize.

A prominent, ~43 kDa novel protein was present in each of the tetC-transformed plants when examining plant total soluble protein (TSP) extracts separated in SDS-PAGE gels (FIG. 23B). Other prominent bands on the gels are the Rubisco large-and small subunits (LSU and SSU, respectively in FIG. 23B) that together constitute about 50% of TSP in wild-type plants. The fidelity of TetC protein expression was confirmed by immunoblotting with anti-TetC antiserum. On the blots two predominant polypeptides were recognized by anti-TetC antisera: one corresponded to the novel 43 kDa protein and a second polypeptide, which had a similar apparent molecular mass to purified bacterial control rTetC (predicted size 47 kDa), co-migrated with the Rubisco large subunit (LSU), The novel 43 kDa protein has both the intact TetC N- and C-termini based on micro-sequencing gel-purified protein (ESI-MS/MS, Edman degradation; data not shown), and therefore it is probably a modified, full size TetC protein. Thus, in chloroplasts, two TetC-derived polypeptides are present: a 47 kDA protein and one with the apparent molecular weight of 43 kDA. Examination of western blots using densitometry and purified TetC standards showed TetC protein to be ~25% TSP in the leaves of Nt-pJSTIO plants and ~10% TSP in Nt-pJST11 and Nt-pJST12 leaves (FIG. 23C). TetC levels in different experiments were in the 18%–27% range in Nt-pJST10 leaves and in the 7%–10% range in Nt-pJST11 and Nt-pJST12 leaves.

The Nt-pJST10 plants, but not the Nt-pJST11 or Nt-pJST12 plants have a mutant phenotype (FIG. 22). Since the Nt-pJST10 leaves contain the highest TetC level, ~25% TSP, the mutant phenotype may be directly linked to TetC expression levels, although the exact contributing factors remain unknown.

Intranasal immunization of mice with leaf protein extract harboring TetC. We decided to employ two different routes of mucosal immunization to rigorously investigate the immunogenicity of the plant derived TetC protein. Initially, groups of mice were immunized intranasally with vaccines harboring extracts from transgenic tobacco leaves mixed with small amounts of purified cholera toxin (CT) acting as adjuvant (FIG. 24A). Control mice were immunized with purified TetC protein from *E. coli* (rTetC) mixed with CT, tobacco leaf extract alone (wt) or phosphate buffered saline (PBS; naive mice sample). The mice were primed on day 0 with leaf protein extracts. Sample bleeds were taken on day 27 and the mice were boosted at days 28 and 35. Final mucosal surface wash samples and sera were collected on day 45.

All groups of mice immunized with extract from transgenic plants expressing TetC had a significant systemic anti-TetC IgG response at day 27 (FIG. 24B). Levels of specific anti-TetC IgG were boosted after re-immunization at days 28 and 35. At day 45 average IgG antibody titers in mice inoculated with 2.7 μg TetC+CT (TetC source Nt-pJST10) and 6.0 μg TetC+CT (TetC source Nt-pJST11) were 3.9×105 and 4.1×105 respectively. The anti-TetC immune responses to the TetC-harboring plant extracts were comparable to the response to the purified TetC-CT control (rTetC: 3.7×105). Mice immunized with non-transgenic leaf extract or buffer alone (PBS) failed to mount a detectable TetC-specific antibody response. Anti-TetC IgA antibody responses were seen at the immunized site in nasal washes (FIG. 24C) and at a distal site in gut washes (FIG. 24D). Conventional tetanus vaccines induce anti-toxoid antibodies measured in IU/ml, which can be assessed by in vitro or in vivo tests (Winsnes et al. 1999). Levels of anti-TetC antibodies comparable to those obtained here have consistently been observed to confer solid protection against a toxin challenge (Figueiredo et al. 1995).

Oral immunization of mice with tobacco leaf expressing TetC. To test the efficacy of transgenic plants for oral immunization, groups of mice were orally gavaged with finely ground leaf tissue suspended in PBS. The leaf samples were tested with and without purified CT as adjuvant. The mice were primed twice, at days 0 and 3, and boosted at day 27 (FIG. 25A). As controls, mice were fed purified *E. coli*-derived TetC (rTetC), non-transformed leaf tissue (wt group) and PBS alone (naive mice).

TetC-specific IgG antibody titers are shown in FIG. 25B. Of the mice immunized with 200 μg TetC (50 mg transgenic Nt-pJST11 leaf tissue)+10 μg CT, 5 out of 9 seroconverted with an average titer of 2.3×104. The level of IgG antibody in the responding mice was high, equivalent to protective levels. Anti-TetC IgA responses were also observed in gut washes of a number of individual mice receiving the transgenic TetC leaf material (FIG. 25C). There was no strict correlation between the IgG and IgA data. Some mice exhibited an anti-TetC IgA response in the gut when they had no detectable anti-TetC IgG in their serum (data not shown).

Protection of mice against tetanus toxin challenge. In order to test if the anti-TetC antibody responses raised in the intranasal trial were protective, five mice nasally immunized with a 6.0 μg priming dose and two 10 μg boosts of TetC, with 1 μg CT coadministered (Group JST11+CT in FIG. 24) were challenged with tetanus toxin: 50-times the dose required to cause paralysis in 50% of mice (50PD50). IgG titers of mice selected for toxin challenge were 364183, 489583, 413829, 218493 and 375292. The values for the five animals overlap, thus showing up as three dots on the plot. As a control group, five naive mice were used. All mice immunized with leaf extract harboring the plant-derived TetC survived the challenge and were free of all symptoms whereas all control animals developed symptoms of paralysis.

Discussion

We have shown here that TetC produced in tobacco leaf is effective for the mucosal immunization of animals against tetanus providing the basis for developing a plant-based tetanus vaccine. Protein extracts from transgenic plants expressing TetC induced protective levels of immunity in mice against tetanus challenge. As well as anti-TetC serum IgG, local anti-TetC IgA production was also detected at the mucosal surfaces of immunized mice. The nasal route was found to be more effective than oral immunization. It is well established that significantly more material is normally required for oral compared to nasal immunization (Douce et al. 1999) and modifications of the method to optimize oral delivery are currently under investigation. One option is to co-express a mucosal adjuvant in the chloroplast with the vaccine antigen. The principal of this approach was elegantly demonstrated by fusing the adjuvant cholera toxin subunits (CTA, CTB) with different antigens and expressing them from nuclear genes (Yu and Langridge 2001).

Studies in heterologous expression hosts have shown that codon usage can greatly influence the level of expression of foreign proteins. A good example is TetC that could be expressed in yeast only from a synthetic but not from the bacterial gene due to the instability of the bacterial mRNA in the eukaryotic yeast (Romanos et al. 1991). The importance of codon bias was investigated here by expressing two tetC genes, one AT rich (72.3% AT) and the more GC rich (52.6% AT) in the same cassette. The AT rich gene reproducibly yielded about twice as much TetC in the leaf of the tobacco plants off the same 5' UTR cassette: ~25% compared to ~10%. A similar (1.5-fold) increase in protein level was observed when comparing expression from bacterial and codon optimized synthetic CP4 gene (Ye et al. 2001). TetC levels in pJST12 (72.3% AT) plants were comparable to pJST11 plants (52.6% AT) confirming that upstream translation control signals are more important than codon usage for protein expression in chloroplasts. Indeed, protein levels from the same promoter in chloroplasts may vary from undetectably low to ~20% of TSP, dependent on the choice of translation control signals, indicating the importance of post-transcriptional regulation in plastid gene expression (Kuroda and Maliga 2001b; Kuroda and Maliga 2001a). The 25% TSP TetC obtained is much higher than protein levels that can be readily obtained from nuclear genes (Ma and Vine 1999; Giddings et al. 2000). However, expression of TetC at ~10% TSP is more practical as it does not cause a mutant phenotype. Tobacco as an expression system compares favorably with *E. coli* because of its simplicity, as production in tobacco leaves does not require expensive fermentors, complex purification or sterile conditions. It also compares favorably with yeast because in tobacco chloroplasts proteins are not glycosylated, whereas in yeast most TetC is rendered immunogenically inactive by glycosylation [Romanos, 1991 #3964. The high tetc protein levels obtained in accordance with the methods of the present invention justify the use of a leafy plant that is related to tobacco, but does not contain the alkaloids present in a tobacco leaf for the production of effective anti-tetanus vaccines.

An improved tetanus vaccine could be used as a booster immunization targeted to women of child-bearing age and preferably delivered without a delivery apparatus such as a syringe. There are two obvious routes for the commercialization of TetC as an oral vaccine. The first is to express TetC and an adjuvant in low nicotine tobacco for further testing and clinical trials. The low nicotine (alkaloid) tobacco and related wild species contain 10-times to 100-times less alkaloid than commercial cultivars grown for cigarette production. Using tobacco has the advantages of being a non-food crop thereby avoiding the potential danger of a vaccine-producing plant inadvertently entering the food chain. This is an issue which was raised by the controversy around Starlink corn, containing an insecticidal protein, approved only for livestock but not for human consumption, being mixed with food corn [Netting, 2000 #3854]. Another important advantage is the familiarity of farmers with tobacco worldwide, facilitating acceptance of this new, non-traditional application. The alternative route is engineering TetC vaccine into a food crop. The advantage of this approach is that vaccines are delivered in an accepted food source. Candidate crops for oral delivery include alfalfa and tomato. Encouraging in this regard is the recent success of plastid transformation in tomato (Ruf et al. 2001). Both approaches are scientifically feasible; the ultimate choice will depend on regulatory issues and social acceptance.

EXAMPLE 6

Expression of the *E. Coli* Heat Labile Enterotoxin B Subunit in Chloroplasts for use as Protective Mucosal Immunogen LT-B is the non-toxic B subunit of the *E. coli* Heat-Labile toxin, a toxic product of ETEC (entero-toxigenic *E. coli*). LT-B is a homo-pentameric protein that binds the holotoxin to enterocytes and lacks the toxic A component. There are immunologically distinguishable forms of LT-B (Human, Porcine) and a significant cross reactivity with cholera toxin B subunit (CT-B).

The role of LT (anti-toxin immunity) in protection against enterotoxigenic *E. coli* and/or cholera has been investigated and is reviewed in references (Clemens et al. 1990; Jertborn et al. 2001). Many studies in animals (intestinal loops, whole animals) and humans (volunteers, field studies, epidemiological observations) have considered the role of anti-toxin antibodies in immunity to cholera and ETEC. The general conclusions are: (1) Anti-toxic immunity is considered insufficient to protect against clinical disease at high efficacy; (2) Any immunity involving anti-toxin activity is likely to be short lived (months as against years) due to the non-bactericidal activity of the immunity (IgA blocking activity); and (3) A combination of antibacterial (whole cell) and anti-toxic activity displays synergy and is considered the most appropriate approach to gain efficacious protection.

Most early studies using LT or CT-based vaccines failed. Both parenteral and oral immunization approaches were employed. This lack of efficacy may be because anti-toxic immunity is really non-protective but two factors should be considered. (1) These old vaccination studies employed chemically inactivated LT and CT which where sub-optimal in terms of immunogenicity and ability to target tissues (important mucosally). (2) Not all vaccines were optimized using modern delivery systems or adjuvants. (3) Some studies in pigs using cholerogenoid (inactivated) LT vaccines showed protection in piglets (maternal antibody) and Swiss Serum marketed a vaccine based on this technology. (3) Many in vivo loop models exhibit protection, correlatable with sIgA production.

Very few studies have been performed using optimized delivery of native CT-B or LT-B alone in humans. Evidence from the field indicates that humans do acquire immunity to cholera and ETEC. Further maternal antibody offers protection to the young. Evidence from volunteers immunized with attenuated (non-LT producing) ETEC induces clinical protection against diarrhea, lowering real levels of ETEC in the small intestine of challenged vaccinees but providing no reduction in stool shedding levels. This could be due to the non-bactericidal activity of IgA. However, when individuals are challenged with heterologous ETEC strains protection is either lost or dramatically reduced.

Field Studies using whole cell cholera vaccines led to the following conclusions: (1) Large scale field studies and observations in Finnish travelers have shown that an oral V. cholerae whole cell (C-WC) combined with CT-B can induce protection of up to 85% for up to 6 months and 50% protection for 2–3 years against cholera. CT-B appears to enhance protection (85% verses 55%) for the first six months but thereafter protection is the same for the C-WC and the C-WC+CT-B. This is a licensed vaccine formulation. (2) Significantly, similar studies have shown short term (3 month protection) at 50–60% efficacy against ETEC with this same vaccine. The investigators (Holmgren and Svennerholm) propose that this is due to the CT-B component. Kaper (SAB) pointed out that this protection was even true for non-LT producing E. coli. Although this could cast doubt on Holmgren's conclusions, non-specific mucosal adjuvant effects could partially explain their data. (3) Of note is the fact that C-WC+CT-B immunization reduces the overall rate of diarrhea in a population. (4) Holmgren and Svennerholm have developed an E. coli vaccine based on inactivated whole ETEC+CT-B. Phase I and II studies were promising and early reports from phase III efficacy studies are also reported to be encouraging. (5) The evidence above suggests that CT-B alone will not protect against cholera. It is still possible that if LT-B is efficiently delivered to the mucosal surface protection/efficacy might occur. However, the most we can expect relatively short term immunity for ETEC. (6) However, other LT derivatives harboring the holotoxoid (LT-B+LT-A) e.g., LTK63 are more likely to be efficacious compared to LT-B due to their ability to induce anti-A subunit as well as anti-B subunit antibodies and their inherently greater adjuvant activities.

Vectors for LTB Expression in Chloroplasts

Figure 26:
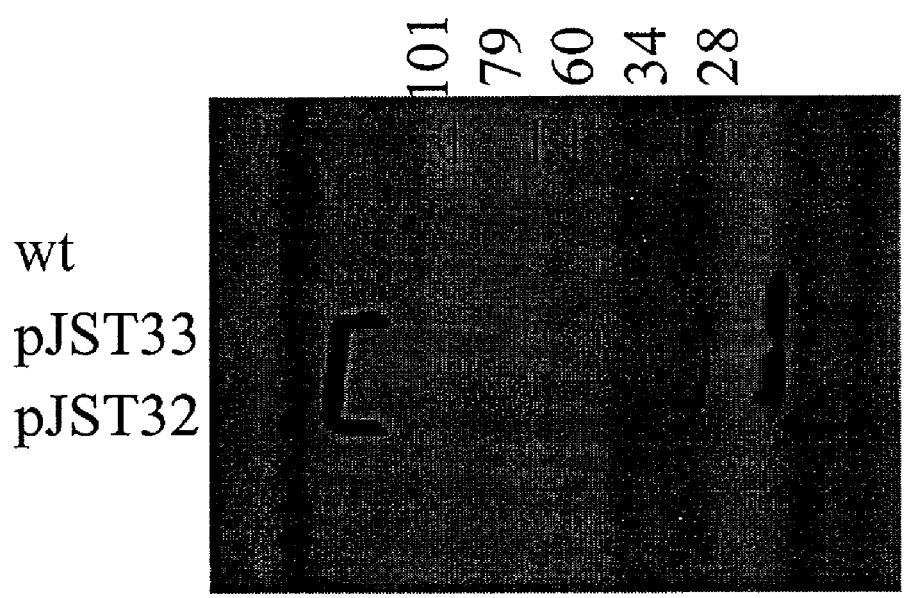
FIG. 26. Immunoblot analysis indicates protein accumulation from plastid genes encoding the pre-protein (pJST32) and mature LTB (pJST33).
Figure 27:
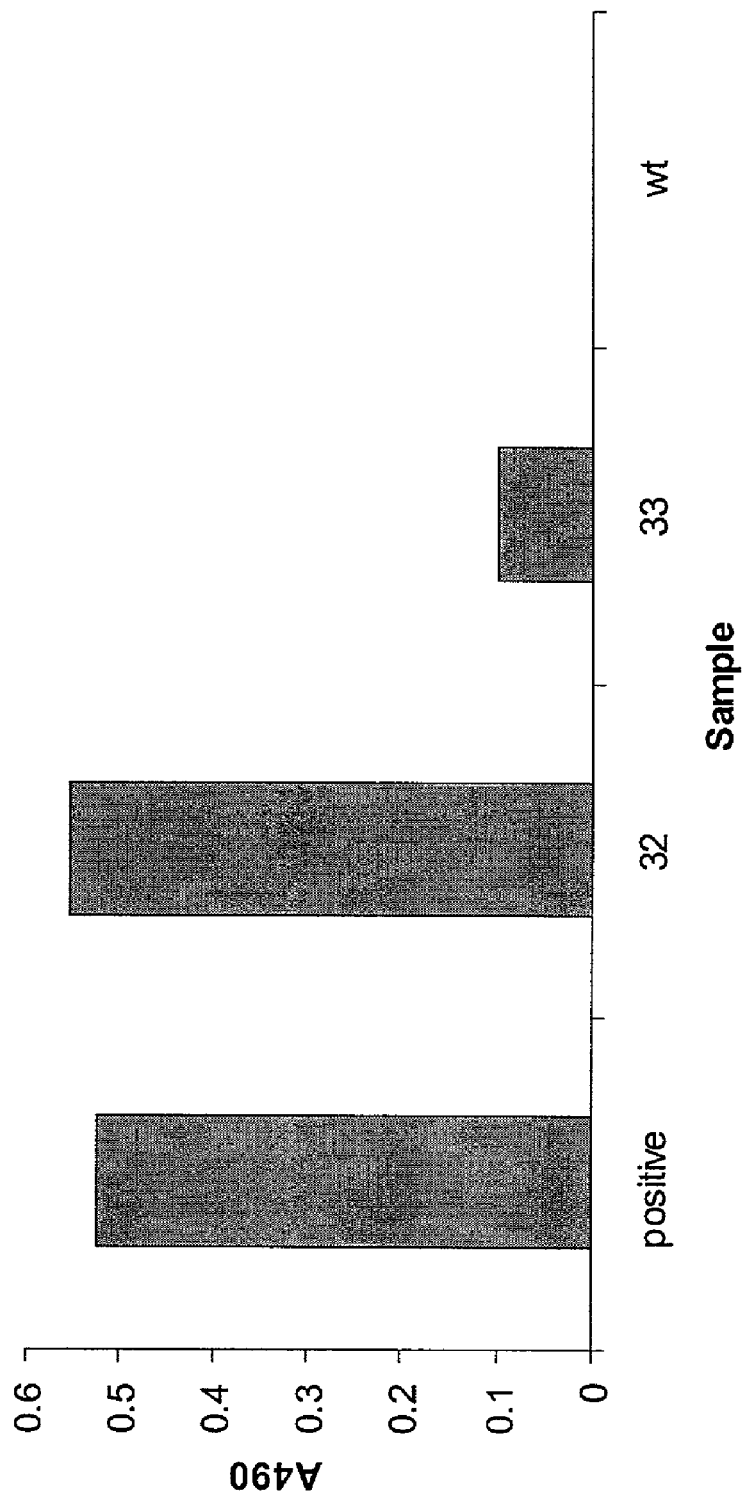
FIG. 27. GM1-ganglioside ELISA binding assay. The data shows that 100 ng of pure Lt-B has the same binding response as the LT-B pentamer in 50 micrograms of total plant soluble extracted proteins.

Two forms of the E. coli heat labile enterotoxin B subunit gene were expressed in chloroplasts. One is the wild-type gene; the coding region includes the signal peptide (LTB-W) (Seq. ID No. 43). The second gene encodes the enterotoxin mature B subunit without signal peptide (LTB-M) (Seq. ID No. 44). The LTB coding regions may be cloned in vectors pHK40 and pHK73, and introduced into chloroplasts as described in Example. Plasmid pJST32 and pJST33 are pHK73 plasmid derivatives. They were obtain by cloning the PCR-generated LTB-W and LTB-M coding regions (NdeI-XbaI fragments) into Nde (-XbaI digested pHK73 vectors. Plasmid pJST32 carries the LTB-W gene encoding pre-LTB, whereas plasmid pJST33 encodes the mature LTB peptide (Seq. ID No. 44). Immunoblot in FIG. 26 shows LTB protein accumulation in the chloroplasts of both pJST32 and pJST33 transformed plants. The GM1 binding assay shown in FIG. 27 shows that the plant formed Lt-B binds GM1 gangliosides which means that it can form pentamers as only the pentamers bind. The data shows that 100 ng of pure Lt-B has the same binding response as the LT-B pentamer in 50 micrograms of total plant soluble extracted proteins. Based on the the assay and the western analysis the LTB pre-protein expressed from plasmid pJST32 folds better than that from plasmid pJST33 encoding the mature LTB. Thus, biologically active LTB in chloroplasts may be produced more efficiently from the bacterial gene encoding the pre-protein than form the gene engineered to express the mature LTB subunit. In the past CTB has been expressed in tobacco chloroplasts without the leader peptide (Daniell et al. 2001). We how here that expression of pre-protein in chloroplasts is desirable as it may yield more biologically active LTB pentamers.

EXAMPLE 7

Expression of the Mutant *Escherichia Coli* Heat-Labile Enterotoxin LTK63 in Cloroplasts to be Used as Mucosal Adjuvant and Immunogen Administration of TetC alone may be insufficient to induce immunoprotective Ig levels. Therefore, adjuvants were produced to potentiate the anti-TetC immune response. The adjuvant may be expressed in the chloroplasts alone, and protein samples or leaf tissue mixed from TetC producing plants and adjuvant producing plants may then be administered. Alternatively, both TetC and the adjuvant may be expressed in the same chloroplast. In the second case, the relative expression levels of TetC and the adjuvant are adjusted to ~10:1 by manipulating the translation control sequences of the plants.

Cholera toxin (CT) and the *Escherichia coli* heat-labile enterotoxins (LT) are the most powerful mucosal immunogens known. CT and LT molecules have high homology (80% identity) in their primary structure and superimposable tertiary structures. Both toxins are composed of a pentameric B (binding) oligomer that binds the receptor(s) on the surface of eukaryotic cells, and an enzymatically active A subunit that is responsible for the toxicity. The A1 (and A2) subunit are generated by proteolytic cleavage of the A subunit subsequent to internalization in eukaryotic cells. The A1 subunit transfers an ADP-ribose group to the α subunit of several GTP-binding proteins involved in signal transduction. Enzymatic activity is enhanced by interaction with 20-kDa GTP-binding proteins, known as ADP-ribosylation factors. CT and LT anti-toxin response is so potent that sometimes a strong immune response is also activated against foreign bystander molecules that are present at the mucosal surface. This immunopotentiating property makes CT and LT useful as mucosal antigens and adjuvants. The non-toxic CTB and LTB subunits are poor adjuvants. The extreme sensitivity of humans to holotoxoids makes them unsuitable for practical use. However, mutations in the A subunit have been identified which render the A subunit enzymatically inactive (or greatly reduce the enzymatic activity) and therefore are non-toxic. Some of the non-toxic LTA mutants maintain both their immunogenicity and their ability to act as adjuvants . Examples are the LTK7, LTK63, LTR72, CTK63 and CTS106 mutations; reviewed in (Douce et al. 1995; Rappuoli et al. 1999; Pizza et al. 2001). In U.S. Pat. No. 6,149,919 immunogenic detoxified proteins comprising the amino acid sequence of subunit A of cholera toxin (CT-A) or subunit A of an *Escherichia coli* heat labile toxin (LT-A) or a fragment thereof wherein one or more amino acids at, or in positions corresponding to Val-53, Ser-63, Val-97, Tyr-104 or Pro-106 were replaced with another amino acid or were deleted. Examples of specific replacements include Val-53-Asp, Val-53-Glu, Val-53-Tyr, Ser-63-Lys, Val-97-Lys, Val-97-Tyr, Tyr-104-Lys, Tyr-104-Asp, Tyr-104-Ser, Pro-106-Ser.

LTK63 is an excellent mucosal adjuvant, although the activity is reproducibly reduced in comparison with LT (Giuliani et al. 1998; Barchfeld et al. 1999). Interestingly, LTK63 is consistently a better immunogen than LTB (Douce et al. 1998; Giuliani et al. 1998), suggesting an important role for the enzymatically inactive A subunit in the induction of an immune response. LTK7 (amino acid change Arg7 to Lys in the LTA subunit) is also a LT derivative lacking ADP-ribosyltransferase activity with utility as a non-toxic mucosal adjuvant (Pizza et al. 1994; Douce et al. 1995). LTR72 (with an alanine to arginine substitution in position 72 of the A subunit), and CTS106 (with a proline to to serine substitution in position 106 of the A subunit) have about 1% of the wild-type ADP-ribosylation activity, and about 1% toxicity in vivo. Both LTR72 and CTS106 are excellent mucosal adjuvants, being as effective as LT and CT, respectively (Douce et al. 1997; Giuliani et al. 1998). The LTK63 is as good an immunogen as the wild-type LTwt protein (Rappuoli et al. 1999). Use of non-toxic LT mutants is exemplified here by the LTK63 mutant, which contains a serine to lysine substitution.

Acute gastroenteritis is second only to acute respiratory disease as a cause of death worldwide in human populations, and it is also a significant problem in farm animals and pets. Cholera, rotavirus and enterotoxigenic *E. coli* (ETEC) are the three causative agents of acute infectious enteric disease. Antigens genetically fused to CTA and CTB subunit were found to stimulate strong immune response in orally immunized animals (Yu and Langridge 2001) (and references therein). Thus, transgenic tobacco plants expressing LTK63 may be utilized for large-scale production of purified LTK63, as an edible vaccine if expressed in an edible plant part or as a transmucosal carrier of peptides to which it is fused, either to induce oral tolerance to these peptides or enhance mucosal immunity.

The plant-produced LTK63 and similar non-toxic (or reduced toxicity) LT and CT derivatives will find broad applications in human healthcare, animal husbandry and veterinary applications. The immunogenic detoxified protein is useful as vaccine for Vibrio cholerae or an enterotoxigenic strain of *Escherichia coli* and is produced by recombinant DNA means by site-directed mutagenesis.

Vectors for LTK63 Expression in Chloroplasts

DNA sequence for several LT and CT isolates have been deposited in GenBank. Examples for LT are Accession Number AB011677, M28523, S60731, J01646, and M17894. Examples for CT are D30052, D30053 and E00132. The LTK63 mutant expressed in chloroplasts derives from a porcine (pig) LT gene. Wild type porcine LTA subunit (M15361, M15362) and LTB subunit (M15363, M17873, J01605) gene sequences have been deposited in GenBank. The LTK63 coding region, including the LTA and LTB coding regions (eltA and eltB genes) (Dallas and Falkow 1980; Spicer and Noble 1982), is included in a KpnI-XbaI fragment. Schematic map of the dicistronic operon with relevant restriction sites is shown in FIG. 26. The DNA sequence is included as SEQ ID No: 33. The wild-type LT operon was modified to: (1) add KpnI cloning site at 5'-end and an NdeI sites to include the translation initiation codon; (2) remove the internal XbaI site by a TCT to TCa silent mutation; (3) introduce the S to K mutation at codon position 63 in the mature LTA subunit by TCT to aaa mutation; GAGAAG to GAGAtc mutation to create a silent BglII site; (5) introduce an XbaI site downstream of the stop codon for linkage with 3' UTR cassettes. Note that the LTA signal sequence is 18 AA long (cleavage occurs between A and N) and the LTB signal sequence is 21 AA long (cleavage occurs between G and A). The heat-labile enterotoxin A subunit (LTA) and B subunit (LTB) coding regions overlap. The ATGA sequence contains the initiation codon of the downstream LTB coding region (c frame in SEQ ID No.33) and the stop codon of the upstream LTA coding region (in the a frame). Thus, translation of the two subunits is probably coupled. Similar overlapping initiation and stop codons have been described for the plastid ATPase beta and epsilon subunit genes in tobacco (Shinozaki et al. 1983). Translational coupling in prokaryotes is observed when the gene products interact in a one to one stoichiometry. In contrast, LT is composed of one A subunit and 5 B subunits. It is likely, that LTB translation is dependent on translation control signals in the LTA C terminus, at least this is the case in the related cholera toxin operon. The CTB subunit is translated 9-times more efficiently from its own translation control signals then from those of CTA (ctxA gene) (Mekalanos et al.).

The bacterial LTK63 operon (SEQ ID NO. 33) encodes the LTA and LTB pre-proteins, with the 18 and 21 amino acid signal sequence. Interestingly, chloroplasts have correctly processed a human cDNA signal peptide and folded the protein that normally requires passing through the ER (Staub et al. 2000). This may not be surprising, since chloroplasts have GTP-dependent signal recognition particle (SRP) systems of the ER and bacteria, and a chloroplast homologue of the mammalian SRP54 subunit. The SRP system in chloroplasts targets proteins to the thylacoid membrane (Keegstra and Cline 1999). Thus, the unmodified bacterial LT operon may be expressed and the encoded LTA and LTB pre-proteins properly processed in chloroplasts. The NdeI-XbaI fragment (SEQ. ID. NO:33) can be cloned directly into NdeI-XbaI digested pHK40 and pHK73 vectors (Example 5) for expression of the LT operon in chloroplasts.

A better control over LTA and LTB expression in chloroplasts may be obtained by expressing the mature proteins rather than the pre-proteins with the signal peptides. The signal sequence at the LTA N-terminus may be conveniently removed using a primer that includes KpnI and NdeI sites, a translation initiation codon (ATG) and the N-terminus of the mature LTA subunit, such as oligonucleotide ggtac-ccatATGAATGGCGACAGATTATACCGTGCTGACTC (SEQ. ID No.34) and a primer downstream of the unique BspEI site so that the KpnI-NdeI fragment in the LTK63 bacterial operon can be replaced with the truncated KpnI-NdeI PCR fragment. Translation of the truncated LTA coding region will yield the mature LTA with the N-terminal amino acid sequence MNGDRLYRAD. Alternatives to using an NdeI site for conveniently linking the 5'-regulatory cassette upstream of LTA are the NcoI and NcoI-NheI restriction sites. To obtain an NcoI site including the translation initiation codon, oligonucleotide ggta ccATGgggAATGGCGACAGATT ATACCGTGCTGACTC (SEQ. ID No.35) may be used (NcoI underlined), so that the N terminus will be MGNGDRLYRAD (G inserted between M and N). If both NcoI and NheI sites (underlined) are included at the N-terminus using oligonucleotide ggta ccATGgctagcAATGGCGACAGATTATACCGTGCTGA CTC (SEQ. ID NO.36), so that the N-terminus will be MASNGDRLYRAD (A and S inserted between M and N). The availability of NcoI and NheI restriction sites would facilitate expression LTA in cassettes described in (Kuroda and Maliga 2001b; Kuroda and Maliga 2001a) and U.S. Pat. No. 5,877,402. If expression of LTA alone is the objective, a stop codon with an XbaI site can be conveniently introduced by using EcoRI-XbaI (underlined) adapter based on the sequence GAATTCGGGATGAATTATGAtctaga (SEQ. ID NO: 37).

Engineering of the LTB subunit for expression in plastids, with and without the signal sequence, is described in Example 7.

To beneficially exploit the translation control signals in the LTA C terminus, it is attractive to express the mature LTA and LTB subunits from a dicistronic mRNA. Truncation of the LTB signal peptide can be conveniently achieved by relying on the unique EcoRI and SacI sites in the LTA C-terminus and LTB N-terminus, respectively (FIG. 26). One solution would be to link the LTA and LTB coding regions via the EcoRI and SacI restriction sites using oligonucleotide gaattcgggatgaattATGAGAGCTC (SEQ ID NO.38) (LTA coding region is in lower case, LTB is in capital) so that the mature LTB N-terminus would be MRAPQTITEL. The R residue may destabilize the LTB protein. Therefore, a better solution will be to separate the overlapping stop and initiation codons using oligonucleotide GAATTCGGGATGAATTATGAtttATGCT (SEQ ID NO:39) or GAATTCGGGATGAATTATGAcatATGCT (SEQ ID NO:40) (this second construct has NdeI site). These oligoinucleotides can be used only if SacI site 3'-overhang is enzymatically removed to leave behind only a C nucleotide. LTB subunits translated from these constructs will have the N-terminus MAPQTITEL) A third solution would be to include a ribosome binding site upstream of the LTB coding region, for example the T7G10 5'-UTR described in (Kuroda and Maliga 2001a) (SEQ ID NO: 41).

Expression of LTK63 in chloroplasts and testing for adjuvanicity and immunogenicity will be carried out as described for the recombinant bacterial CT in Example 5 and for the chloroplast produced LTB in Example 6. The constructs are designed to obtain maximum yield of assembled LT.

EXAMPLE 8

Construction of Marker-free Tobacco Plant Expressing TetC and LTK63

Production of a practical TetC vaccine and mutant LT as adjuvants may be accomplished in a low nicotine tobacco cultivar such as LAMD609, LAFC53, derivatives of the low nicotine Burley 21 which carry two recessive mutations controlling nicotine levels (Saunders and Bush 1979). The alkaloid content of some wild *Nicotiana* species even lower, ~20–40 microgram/g dry weight (Saitoh et al. 1085). Thus, engineering will be carried out in *N. tabacum* cv. Petit Havana, used a model for plastid engineering, a low nicotine cultivar or species such as *N. alata, N. forgetiana, N. longiflora* or *N. umbratica.*

The tetC, LTK63 operon and aadA are introduced into the plastid genome as one operon as depicted in FIG. 29. The TetC (Seg. ID No. 32) is expressed from the Prrn:T7g10 5'-legulatory region as in Nt-pJST12 plants (Fragment 1/3). The atpB RBS (RBS2) is included in an XbaI/NdeI fragment (3/4; Seg. ID No. 46). The LTK63 operon is included in an NdeI-XbaI fragment (Fragment 4/5; Seg. ID No. 33). Sequence 5/6 is and XbaI-NcoI fragment with a lox site and RBS3 (Seg. ID No. 45). The aadA coding (Fragment 6/7) region is included in an lNcoI/XbaI fragment (Svab and Maliga 1993). The lox-T1 terminator sequence (Fragment 7/8) is Seq. ID 5.

Methods for plastid transformation, CRE-mediated excision of aadA and verification of biological activity has been Exemplified in the earlier examples.

Anderson R, Gao X M, Papakonstatinopoulou A, Roberts M, Dougan G (1996) Immune response in mice following immunization with DNA encoding fragment C of tetanus toxin. Infect Immun 64:3168–3173

Barchfeld G L, Hessler A L, Chen M, Pizza M, Rappuoli R, Van_Nest G A (1999) The adjuvants MF59 and LT-K63 enhance the mucosal and systemic immunogenicity of subunit influenza vaccine administered intranasally in mice. Vaccine 17:695–704

Bock R (2001) Transgenic plastids in basic research and plant biotechnology. J Mol Biol 312:425–438

Carrer H, Hockenberry T N, Svab Z, Maliga P (1993) Kanamycin resistance as a selectable marker for plastid transformation in tobacco. Mol Gen Genet 241:49–56

Charles I G, Rodgers B C, Makoff A J, Chatfield S N, Slater D E, Fairweather N F (1991) Synthesis of tetanus toxin fragment C in insect cells by use of a baculovirus expression system. Infect Immun 59:1627–1632

Clemens J D, Sack D A, Harris J R, Van_Loon F, Chakraborty J, Ahmed F, Rao M R, Khan M R, Yunus M, Huda N (1990) Field trial of oral cholera vaccines in Bangladesh: results from three-year follow-up. Lancet 335:270–273

Dallas W S, Falkow S (1980) Amino acid sequence homology between cholera toxin and *Escherichia coli* heat-labile toxin. Nature 288:499–501

Daniell H, Lee S B, Panchal T, Wiebe P O (2001) Expression of the native cholera toxin B subunit gene and assembly of functional oligomers in transgenic tobacco chloroplasts. J Mol Biol 311:1001–1009

Douce G, Fontana M, Pizza M, Rappuoli R, Dougan G (1997) Intranasal immunogenicity and adjuvanticity of site-directed mutant derivatives of cholera toxin. Infect Immun 65:2821–2828

Douce G, Giannella V, Pizza M, Rappuoli R, Dougan G (1999) Genetically detoxified mutants of Heat-Labile toxin of *Excherichia coli* are able to act as oral adjuvants. Infect Immun 67:4400–4406

Douce G, Giuliani M M, Giannelli V, Pizza M G, Rappuoli R.

Dougan G (1998) Mucosal immunogenicity of genetically detoxified derivatives of heat labile toxin from *Escherichia coli*. Vaccine 16:1065–1073

Douce G, Turcotte C, Cropley I, Roberts M, Pizza M, Domenghini M, Rappuoli R, Dougan G (1995) Mutants of *Escherichia coli* heat-labile toxin lacking ADP-ribosyl-transferase activity act as nontoxic, mucosal adjuvants. Proc Natl Acad Sci USA 92:1644–1648

Figueiredo D, Turcotte C, Frankel G, Li Y, Dolly O, Wilkin G, Marriott D, Fairweather N, Dougan G (1995) Characterization of recombinant tetanus toxin derivatives suitable for vaccine development. Infect Immun 63:3218–3221

Giddings G, Allison G, Brooks D, Carter A (2000) Transgenic plants as factories for biopharmaceuticals. Nat Biotechnol 18:1151–1155

Giuliani M M, Del_Giudice G, Giannelli V, Dougan G, Douce G. Rappuoli R. Pizza M (1998) Mucosal adjuvanticity and immunogenicity of LTR72, a novel mutant of *Escherichia coli* heat-labile enterotoxin with partial knockout of ADP-ribosyltransferase activity. J Exp Med 187:1123–1132

Haq T A, Mason H S, Clements J D, Arntzen C J (1995) Oral immunization with a recombinant bacterial antigen produced in transgenic plants. Science 268

Heifetz P B (2000) Genetic engineering of the chloroplast. Biochimie 82:655–666

Jacobs L (2001) First, do no harm. Immunization Focus 2:2–5

Jertborn M, Ahren C, Svennerholm A M (2001) Dose-dependent circulating immunoglobulin A antibody-secreting cell and serum antibody responses in Swedish volunteers to an oral inactivated enterotoxigenic *Escherichia coli* vaccine. Clin Diagn Lab Immunol 8:424–428

Keegstra K, Cline K (1999) Protein import and routing systems of chloroplasts. Plant Cell 11:557–570

Kong Q, Richter L, Yang Y F, Arntzen C J, Mason H S, Thanavala Y (2001) Oral immunization with hepatitis B surface antigen expressed in transgenic plants. Proc Natl Acad Sci USA 98:11539–11544

Kuroda H, Maliga P (2001a) Complementarity of the 16S rRNA penultimate stem with sequences downstream of the AUG destabilizes the plastid mRNAs. Nucleic Acids Res 29:970–975

Kuroda H, Maliga P (2001b) Sequences downstream of the translation initiation codon are important determinants of translation efficiency in chloroplasts. Plant Physiol 125:430–436

Levine M M, Dougan G (1998) Optimism over vaccines administered through mucosal surfaces. Lancet 351:1375–1376

Ma J K (2000) Genes, greens, and vaccines. Nat Biotechnol 18:1141–1142

Ma J K, Vine N D (1999) Plant expression systems for the production of vaccines. Curr Top Microbiol Immunol 236:275–292

Ma S W, Zhao D L, Yin Z Q, Mukherjee R, Singh B, Qin H Y, Stiller C R, Jevnikar A M (1997) Transgenic plants expressing autoantigens fed to mice to induce oral immune tolerance. Nat Med 3

Makoff A J, Oxer M D, Romanos M A, Fairweather N F, Ballantine S (1989) Expression of tetanus toxin fragment C in *E. coli:* high level expression by removing rare codons. Nucleic Acids Res 17:10191–10202

Maliga P (2002) Engineering the plastid genome of higher plants. Curr Opin Plant Biol 5:164–172

Mason H S, Ball J M, Shi J J, Jiang X, Estes M K, Arntzen C J (1996) Expression of Norwalk virus capsid protein in transgenic tobacco and potato and its oral immunogenicity in mice. Proc Natl Acad Sci USA 93:5335–5340

Mason H S, Lam D M, Arntzen C J (1992) Expression of hepatitis B surface antigen in transgenic plants. Proc Natl Acad Sci USA 89:11745–11749

Mekalanos J J, Swartz D J, Pearson G D, Harford N, Groyne F, de_Wilde M Cholera toxin genes: nucleotide sequence, deletion analysis and vaccine development. Nature 306:551–557

Murashige T, Skoog F (1962) A revised medium for the growth and bioassay with tobacco tissue culture. Physiol Plant 15:473–497

Pizza M, Fontana M R, Giuliani M M, Domenighini M, Magagnoli C, Giannelli V, Nucci D, Hol W, Manetti R, Rappuoli R (1994) A genetically detoxified derivative of heat-labile *Escherichia coli* enterotoxin induces neutralizing antibodies against the A subunit. J Exp Med 180:2147–2153

Pizza M, Giuliani M M, Fontana M R, Monaci E, Douce G, Dougan G. Mills K H, Rappuoli R, Del_Giudice G (2001) Mucosal vaccines: non toxic derivatives of LT and CT as mucosal adjuvants. Vaccine 19:2534–2541

Rappuoli R, Pizza M, Douce G, Dougan G (1999) Structure and mucosal adjuvanticity of cholera and *Escherichia coli* heat-labile enterotoxins. Immunol Today 20:493–500

Romanos M A, Makoff A J, Fairweather N F, Beesley K M, Slater D E, Rayment F B, Payne M M, Clare J J (1991) Expression of tetanus toxin fragment C in yeast: gene synthesis is required to eliminate fortuitous polyadenylation sites in AT-rich DNA. Nucleic Acids Res 19:1461–1467

Ruf S, Hermann M, Berger I J, Carrer H, Bock R (2001) Stable genetic transformation of tomato plastids: foreign protein expression in fruit. Nat Biotechnol 19:870–875

Saitoh F, Noma M, Kawashima N (1085) The alkaloid contents of sixty *Nicotiana* species. Phytochemistry 24:477–480

Saunders J W, Bush L P (1979) Nicotine biosynthetic enzyme activities in *Nicotiana tabacum* L. genotypes with diffferent alkaloid levels. Plant Physiol 64:236–240

Shinozaki K, Deno H, Kato A, Sugiura M (1983) Overlap and cotranscription of the genes for the beta and epsilon subunits of tobacco chloroplast ATPase. Gene 24:147–155

Silhavy D, Maliga P (1998) Mapping of the promoters for the nucleus-encoded plastid RNA polymerase (NEP) in the iojap maize mutant. Curr Genet 33:340–344

Spicer E K, Noble J A (1982) *Escherichia coli* heat-labile enterotoxin. Nucleotide sequence of the A subunit gene. J Biol Chem 257:5716–5721

Staub J M, Garcia B, Graves J, Hajdukiewicz P T J, Hunter P, Nehra N, Paradkar V, Schlittler M, Carroll J A, Ward D, Ye G, Russell D A (2000) High-yield production of a human therapeutic protein in tobacco chloroplasts. Nat Biotechnol 18:333–338

Stratford R, Douce G, Zhang-Barber L, Fairweather N, Eskola J. Dougan G (2001) Influence of codon usage on the immunogenicity of a DNA vaccine against tetanus. Vaccine 19:810–815

Svab Z, Maliga P (1993) High-frequency plastid transformation in tobacco by selection for a chimeric aadA gene. Proc Natl Acad Sci USA 90:913–917

Tacket C O, Mason H S, Losonsky G, Estes M K, Levine M M, Arntzen C J (2000) Human immune response to a novel Norwalk virus vaccine delivered in transgenic potatoes. J Infect Dis 182:302–305

Thanavala Y, Yang Y F, Lyons P, Mason H S, Arntzen C (1995) Immunogenicity of transgenic plant-derived hepatitis B surface antigen. Proc Natl Acad Sci USA 92:3358–3361

Walmsley A M, Arntzen C J (2000) Plants for delivery of edible vaccines. Curr Opin Biotechnol 11:126–129

Winsnes R, Hendriksen C, Sesardic D, Akkermans A, Daas A (1999) Serological assays as alternatives to the Ph Eur challenge test for batch release of tetanus vaccines for human use. Dev Biol Stand 101:277–288

Ye G N, Hajdukiewicz P T J, Broyles D, Rodriquez D, Xu C W, Nehra N, Staub J M (2001) Plastid-expressed 5-enolpyruvylshikimate-3-phosphate synthase genes provide high level glyphosate tolerance in tobacco. Plant J 25:261–270

Yu J, Langridge W H R (2001) A plant-based multicomponent vaccine protects mice from enteric disease. Nat Biotechnol 19:548–552

The following sequences were utilized in the methods of Examples 5–8.

```
Sequence ID.
No.31 tetCAT sequence NdeI-XbaI fragment
CATATGAAAA ATCTGGATTG TTGGGTCGAC AATGAAGAAG
ATATAGATGT TATATTAAAA AAGAGTACAA TTTTAAATTT
AGATATTAAT AATGATATTA TATCAGATAT ATCTGGGTTT
AATTCATCTG TAATAACATA TCCAGATGCT CAATTGGTGC
CCGGAATAAA TGGCAAAGCA ATACATTTAG TAAACAATGA
ATCTTCTGAA GTTATAGTGC ATAAAGCTAT GGATATTGAA
TATAATGATA TGTTTAATAA TTTTACCGTT AGCTTTTGGT
TGAGGGTTCC TAAAGTATCT GCTAGTCATT TAGAACAATA
TGGCACAAAT GAGTATTCAA TAATTAGCTC TATGAAAAAA
CATAGTCTAT CAATAGGATC TGGTTGGAGT GTATCACTTA
AAGGTAATAA CTTAATATGG ACTTTAAAAG ATTCCGCGGG
AGAAGTTAGA CAAATAACTT TTAGGGATTT ACCTGATAAA
TTTAATGCTT ATTTAGCAAA TAAATGGGTT TTTATAACTA
TTACTAATGA TAGATTATCT TCTGCTAATT TGTATATAAA
TGGAGTACTT ATGGGAAGTG CAGAAATTAC TGGTTTAGGA
GCTATTAGAG AGGATAATAA TATAACATTA AAACTAGATA
GATGTAATAA TAATAATCAA TACGTTTCTA TTGATAAATT
TAGGATATTT TGCAAAGCAT TAAATCCAAA AGAGATTGAA
AAATTATACA CAAGTTATTT ATCTATAACC TTTTTAAGAG
ACTTCTGGGG AAACCCTTTA CGATATGATA CAGAATATTA
TTTAATACCA GTAGCTTCTA GTTCTAAAGA TGTTCAATTG
AAAAATATAA CAGATTATAT GTATTTGACA AATGCGCCAT
CGTATACTAA CGGAAAATTG AATATATATT ATAGAAGGTT
ATATAATGGA CTAAAATTTA TTATAAAAAG ATATACACCT
AATAATGAAA TAGATTCTTT TGTTAAATCA GGTGATTTTA
TTAAATTATA TGTATCATAT AACAATAATG AGCACATTGT
AGGTTATCCG AAAGATGGAA ATGCCTTTAA TAATCTTGAT
AGAATTCTAA GAGTAGGTTA TAATGCCCCA GGTATCCCTC
TTTATAAAAA AATGGAAGCA GTAAAATTGC GTGATTTAAA
AACCTATTCT GTACAACTTA AATTATATGA TGATAAAAAT
GCATCTTTAG GACTAGTAGG TACCCATAAT GGTCAAATAG
GCAACGATCC AAATAGGGAT ATATTAATTG CAAGCAACTG
GTACTTTAAT CATTTAAAAG ATAAAATTTT AGGATGTGAT
TGGTACTTTG TACCTACAGA TGAAGGATGG ACAAATGATT
AATTTCTAGA No.32 tetCGC sequence NdeI-XbaI fragment
CATATGAAAA ACCTTGATTG TTGGGTCGAC AACGAAGAAG
ACATCGATGT TATCCTGAAA AAGTCTACCA TTCTGAACTT
GGACATCAAC AACGATATTA TCTCCGACAT CTCTGGTTTC
AACTCCTCTG TTATCACATA TCCAGATGCT CAATTGGTGC
CGGGCATCAA CGGCAAAGCT ATCCACCTGG TTAACAACGA
ATCTTCTGAA GTTATCGTGC ACAAGGCCAT GGACATCGAA
TACAACGACA TGTTCAACAA CTTCACCGTT AGCTTCTGGC
TGCGCGTTCC GAAAGTTTCT GCTTCCCACC TGGAACAGTA
CGGCACTAAC GAGTACTCCA TCATCAGCTC TATGAAGAAA
CACTCCCTGT CCATCGGCTC TGGTTGGTCT GTTTCCCTGA
AGGGTAACAA CCTGATCTGG ACTCTGAAAG ACTCCGCGGG
CGAAGTTCGT CAGATCACTT TCCGCGACCT GCCGGACAAG
TTCAACGCGT ACCTGGCTAA CAAATGGGTT TTCATCACTA
TCACTAACGA TCGTCTGTCT TCTGCTAACC TGTACATCAA
CGGCGTTCTG ATGGGCTCCG CTGAAATCAC TGGTCTGGGC
GCTATCCGTG AGGACAACAA CATCACTCTT AAGCTGGACC
GTTGCAACAA CAACAACCAG TACGTATCCA TCGACAAGTT
CCGTATCTTC TGCAAAGCAC TGAACCCGAA AGAGATCGAA
AAACTGTATA CCAGCTACCT GTCTATCACC TTCCTGCGTG
ACTTCTGGGG TAACCCGCTG CGTTACGACA CCGAATATTA
CCTGATCCCG GTAGCTTCTA GCTCTAAAGA CGTTCAGCTG
AAAAACATCA CTGACTACAT GTACCTGACC AACGCGCCGT
CCTACACTAA CGGTAAACTG AACATCTACT ACCGACGTCT
GTACAACGGC CTGAAATTCA TCATCAAACG CTACACTCCG
AACAACGAAA TCGATTCTTT CGTTAAATCT GGTGACTTCA
TCAAACTGTA CGTTTCTTAC AACAACAACG AACACATCGT
TGGTTACCCG AAAGACGGTA ACGCTTTCAA CAACCTGGAC
AGAATTCTGC GTGTTGGTTA CAACGCTCCG GGTATCCCGC
TGTACAAAAA AATGGAAGCT GTTAAACTGC GTGACCTGAA
AACCTACTCT GTTCAGCTGA AACTGTACGA CGACAAAAAC
GCTTCTCTGG GTCTGGTTGG TACCCACAAC GGTCAGATCG
GTAACGACCC GAACCGTGAC ATCCTGATCG CTTCTAACTG
GTACTTCAAC CACCTGAAAG ACAAAATCCT GGGTTGCGAC
TGGTACTTCG TTCCGACCGA TGAAGGTTGG ACCAACGACT
AATCTAGA No.33 bacterial LTK63 operon with pre-LTA and
pre-LTB reading frames
ggtacccatA TGAAAAATAT AACTTTCATT TTTTTTATTT
TATTAGCATC GCCATTATAT GCAAATGGCG ACAGATTATA
CCGTGCTGAC TCaAGACCCC CAGATGAAAT AAAACGTTCC
GGAGGTCTTA TGCCCAGAGG GCATAATGAG TACTTCGATA
GAGGAACTCA AATGAATATT AATCTTTATG ATCACGCGAG
AGGAACACAA ACCGGCTTTG TCAGATATGA TGACGGATAT
GTTTCCACTa aaCTTAGTTT GAGAtcTGCT CACTTAGCAG
GACAGTCTAT ATTATCAGGA TATTCCACTT ACTATATATA
TGTTATAGCG ACAGCACCAA ATATGTTTAA
    TGTTAATGAT GTATTAGGCG TATACAGCCC TCACCCCTAT
GAACAGGAGG
    TTTCTGCGTT AGGCGGAATA CCATATTCTC AGATATATGG
ATGGTATCGT
    GTTAATTTTG GTGTGATTGA TGAACGATTA CATCGTAACA
GGGAGTATAG
    AGACCGGTAT TACAGAAATC TGAATATAGC TCCGGCAGAG
GATGGTTACA
    GATTAGCAGG TTTCCCACCG GATCACCAAG CTTGGAGAGA
AGAACCCTGG
    ATTCATCATG CACCCACAAGG TTGTGGAAAT TCATCAAGAA
CAATCACAGG
    TGATACTTGT AATGAGGAGA CCCAGAATCT GAGCACAATA
TATCTCAGGG
    AATATCAATC AAAAGTTAAG AGGCAGATAT TTTCAGACTA
TCAGTCAGAG
    GTTGACATAT ATAACAGAAT TCGGGATGAA TTATGAATAA
AGTAAAATGT
    TATGTTTTAT TTACGGCGTT ACTATCCTCT CTATATGCAC
ACGGAGCTCC
    CCAGACTATT ACAGAACTAT GTTCGGAATA TCGCAACACA
CAAATATATA
    CGATAAATGA CAAGATACTA TCATATACGG AATCGATGGC
AGGCAAAAGA
    GAAATGGTTA TCATTACATT TAAGAGCGGC GAAACATTTC
AGGTCGAAGT
    CCCGGGCAGT CAACATATAG ACTCCCAGAA AAAAGCCATT
GAAAGGATGA
    AGGACACATT AAGAATCACA TATCTGACCG AGACCAAAAT
TGATAAATTA
    TGTGTATGGA ATAATAAAAC CCCCAATTCA ATTGCGGCAA
TCAGTATGAA
    AAACTAGTct aga No.34 LTA 5' primer to remove signal peptide
and create NdeI site:
ggtacccatATGAATGGCGACAGATTATACCGTGCTGACTC No.35 LTA 5' primer to remove signal peptide and
```

-continued create NcoI site:
ggtaccATGgggAATGGCGACAGATTATACCGTGCTGACTC

No.36 LTA 5' primer to remove signal peptide and
create NcoI and NheI sites:
ggtaccATGgctagcAATGGCGACAGATTATACCGTGCTGACTC No.37 LTA 3' end, to introduce XbaI site
downstream of stop codon:
GAATTCGGGATGAATTATGAtctaga No.38 Dicistronic mRNA, LTB N-terminus is MRAPQ.
LTA 3'-LTB 5' linked via EcoRI and SacI sites;
gaattcgggatgaattATGAGAGCTC.

No.39 Dicistronic mRNA, LTB N-terminus is MAPQ.
LTA 3'-LTB 5' linked via EcoRI and SacI (blunt in
LTB) sites;
GAATTCGGGATGAATTATGAtttATGGCT No.40 Dicistronic mRNA, LTB N-terminus is MAPQ;
with NdeI site. LTA 3'-LTB 5' linked via
EcoRI and SacI (blunt in LTB) sites;
GAATTCGGGATGAATTATGAcatATGGCT No.41 T7g10 5'UTR in LTA/LTB intergenic region;
ExoRI-SacI (blunt in LTB) fragment:
GAATTCGGGATGAATTATGAgggagaccacaacggtttcccActagaaat
aattttgtttaactttaagaaggagatatacatATGGCT No.42 RBS or ribosome binding site based on rbcL
5'UTR, contained in EcoRI-NcoI fragment:
gaattcAGTTGTAGGGAGGGAtccatgg No.43 Pre-LTB with signal sequence; NdeI-XbaI
fragment
CATATGAATA AAGTAAAATG TTATGTTTTA TTTACGGCGT
TACTATCCTC TCTATATGCA CACGGAGCTC CCCAGACTAT
TACAGAACTA TGTTCGGAAT ATCGCAACAC ACAAATATAT
ACGATAAATG ACAAGATACT ATCATATACG GAATCGATGG
CAGGCAAAAG AGAAATGGTT ATCATTACAT TTAAGAGCGG
CGAAACATTT CAGGTCGAAG TCCCGGGCAG TCAACATATA
GACTCCCAGA AAAAAGCCAT TGAAAGGATG AAGGACACAT
TAAGAATCAC ATATCTGACC GAGACCAAAA TTGATAAATT
ATGTGTATGG AATAATAAAA CCCCCAATTC AATTGCGGCA
ATCAGTATGA AAAACTAGTT CTAGA No.44 LTB; NdeI-XbaI fragment—separate sheet
CATATGGCTC CCCAGACTAT TACAGAACTA TGTTCGGAAT
ATCGCAACAC ACAAATATAT ACGATAAATG ACAAGATACT
ATCATATACG GAATCGATGG CAGGCAAAAG AGAAATGGTT
ATCATTACAT TTAAGAGCGG CGAAACATTT CAGGTCGAAG
TCCCGGGCAG TCAACATATA GACTCCCAGA AAAAAGCCAT
TGAAAGGATG AAGGACACAT TAAGAATCAC ATATCTGACC
GAGACCAAAA TTGATAAATT ATGTGTATGG AATAATAAAA
CCCCCAATTC AATTGCGGCA ATCAGTATGA AAAACTAGTC TAGA No.45 XbaI-NcoI lox-RBS sequence
tctagataacttcgtataatgtatgctatacgaagttatGAATtcGAAGC
GCtTGGATACAGTTGTAGGGAGGGAtccatgg No. 46. XbaI-NdeI sequence containg the atpB
5'-UTR of pHK71 and 73 plasmids
tctagaAATTAACCGATCGACGTGCa AGCGGACATT TATTTTaAAT
TCGATAATTT TTGCAAAAAC ATTTCGACAT ATTTATTTAT
TTTATTcaTA TG While certain of the preferred embodiments of the present invention have been described and specifically exemplified above, it is not intended that the invention be limited to such embodiments. Various modifications may be made thereto without departing from the escope and spirit of the present invention, as set forth in the following claims.

What is claimed is:

1. A nucleic acid construct for expression of at least one immunogenic protein in plant plastids, comprising:
   a) a nucleic acid sequence encoding at least one immunogenic protein, wherein said sequence comprises SEQ ID NO: 33, encoding LTK63, and
   b) a nucleic acid sequence encoding a selectable marker; said sequence of a) and said selectable marker encoding nucleic acid being operably linked to 5' and 3' regulatory sequences which function in the plastids of plants, wherein said selectable marker gene allows for the selection of cells comprising plastids transformed with said nucleic acid construct.

2. The nucleic acid construct of claim 1, wherein the nucleic acid sequence of a) also comprises SEQ ID NO:31, encoding TetC.

3. A vector comprising the nucleic acid construct of claim 1.

4. A plant cell comprising the vector of claim 3.

5. The nucleic acid construct of claim 1, wherein expression of said selectable marker encoding nucleic acid confers resistance to a selectable agent selected from the group consisting of kanamycin, gentamycin, spectinomycin, streptomycin and hygromycin, phosphinotricin, basta, glyphosate and bromoxynil.

6. A plant comprising the plant cell of claim 4.

7. The nucleic acid construct of claim 1, wherein said at least one immunogenic protein is selected from the group consisting of a vaccine antigen and a mucosal adjuvant.

8. The nucleic acid construct of claim 1, wherein said selectable marker gene is flanked by site-specific recombinase excision sites.

9. The nucleic acid construct of claim 8, wherein said excision sites are selected from the group consisting of LOX sequences and frt sequences.

10. The nucleic acid construct of claim 1, wherein said sequence encoding at least one immunogenic protein is SEQ ID NO: 33.

* * * * *